US012697134B2

(12) United States Patent
Thai et al.

(10) Patent No.: US 12,697,134 B2
(45) Date of Patent: Aug. 4, 2026

(54) TRANSCATHETER PUNCTURE NEEDLE SYSTEM

(71) Applicant: Edwards Lifesciences Corporation, Irvine, CA (US)

(72) Inventors: Linda Thai, Mission Viejo, CA (US); Lillian Grace Myers, Prairie Village, KS (US)

(73) Assignee: Edwards Lifesciences Corporation, Irvine, CA (US)

( * ) Notice: Subject to any disclaimer, the term of this patent is extended or adjusted under 35 U.S.C. 154(b) by 801 days.

(21) Appl. No.: 17/696,402

(22) Filed: Mar. 16, 2022

(65) Prior Publication Data

US 2022/0202443 A1 Jun. 30, 2022

Related U.S. Application Data

(63) Continuation of application No. PCT/US2020/050623, filed on Sep. 14, 2020.
(Continued)

(51) Int. Cl.
A61B 17/34 (2006.01)
A61M 25/00 (2006.01)
A61M 25/09 (2006.01)

(52) U.S. Cl.
CPC ...... A61B 17/3403 (2013.01); A61B 17/3417 (2013.01); A61M 25/0082 (2013.01);
(Continued)

(58) Field of Classification Search
CPC ............ A61B 17/3403; A61B 17/3417; A61B 17/3478; A61B 2017/00247;
(Continued)

(56) References Cited

U.S. PATENT DOCUMENTS 3,538,917 A 11/1970 Selker
3,675,656 A 7/1972 Hakim
(Continued)

FOREIGN PATENT DOCUMENTS

CN 111317516 A 6/2020
CN 113367839 A 9/2021
(Continued)

OTHER PUBLICATIONS

Bechtold C., et al., "Method for Fabricating Miniaturized NiTi Self-Expandable Thin Film Devices with Increased Radiopacity", Shape Memory and Superelasticity, 2016, vol. 2, pp. 391-398.
(Continued)

*Primary Examiner* — Elizabeth Houston
*Assistant Examiner* — Serenity A Miller
(74) *Attorney, Agent, or Firm* — Klarquist Sparkman LLP

(57) ABSTRACT
A puncture needle can comprise a puncture tip configured to pierce tissue, and a distal portion comprising an anchor portion and a curved puncture portion. The curved puncture portion can comprise a first end associated with the puncture tip and a second end coupled to the anchor portion, where the anchor portion comprises a portion distal of the curved puncture portion. A puncture needle system can comprise the puncture needle and a delivery catheter comprising a lumen, the puncture needle extending through the lumen. The delivery catheter can have a side outlet opening on a distal portion of the delivery catheter configured to allow extension therethrough of at least a portion of the curved puncture portion, where the anchor portion extends through a portion of the lumen distal of the side outlet opening.

29 Claims, 15 Drawing Sheets

Related U.S. Application Data

(60) Provisional application No. 62/902,747, filed on Sep. 19, 2019.

(52) U.S. Cl.
CPC ................. *A61M 25/09041* (2013.01); *A61M 2025/0095* (2013.01); *A61M 2210/125* (2013.01)

(58) Field of Classification Search
CPC ........... A61B 17/34–3498; A61B 17/06–0625; A61M 25/0082; A61M 25/082; A61M 25/0084
USPC ................ 606/185, 223; 604/170.03, 164.01
See application file for complete search history.

(56) References Cited

U.S. PATENT DOCUMENTS

| | | | |
|---|---|---|---|
| 3,730,186 A | 5/1973 | Edmunds et al. | |
| 3,853,126 A | 12/1974 | Schulte | |
| 3,882,862 A | 5/1975 | Berend | |
| 3,882,882 A | 5/1975 | Preisig | |
| 3,903,894 A | 9/1975 | Rosen et al. | |
| 4,256,094 A | 3/1981 | Kapp et al. | |
| 4,428,365 A | 1/1984 | Hakky | |
| 4,556,050 A | 12/1985 | Hodgson et al. | |
| 4,578,061 A | 3/1986 | Lemelson | |
| 4,586,501 A | 5/1986 | Claracq | |
| 4,601,718 A | 7/1986 | Possis et al. | |
| 4,655,777 A | 4/1987 | Dunn et al. | |
| 4,708,140 A | 11/1987 | Baron | |
| 4,712,551 A | 12/1987 | Rayhanabad | |
| 4,739,762 A | 4/1988 | Palmaz | |
| 4,762,128 A | 8/1988 | Rosenbluth | |
| 4,774,949 A | 10/1988 | Fogarty | |
| 4,828,544 A | 5/1989 | Lane et al. | |
| 4,861,336 A | 8/1989 | Helzel | |
| 4,881,939 A | 11/1989 | Newman | |
| 4,946,457 A | 8/1990 | Elliott | |
| 4,950,227 A | 8/1990 | Savin et al. | |
| 4,961,729 A | 10/1990 | Vaillancourt | |
| 4,997,431 A | 3/1991 | Isner et al. | |
| 5,026,377 A | 6/1991 | Burton et al. | |
| 5,041,127 A * | 8/1991 | Troutman ........ | A61B 17/06066 223/102 |
| 5,054,492 A | 10/1991 | Scribner et al. | |
| 5,059,207 A * | 10/1991 | Shah ................ | A61B 17/06066 223/102 |
| 5,108,420 A | 4/1992 | Marks | |
| 5,109,420 A | 4/1992 | Nonaka | |
| 5,114,408 A | 5/1992 | Fleischhaker et al. | |
| 5,167,239 A | 12/1992 | Cohen et al. | |
| 5,190,528 A | 3/1993 | Fonger et al. | |
| 5,193,546 A | 3/1993 | Shaknovich | |
| 5,201,757 A | 4/1993 | Heyn et al. | |
| 5,242,397 A | 9/1993 | Barath et al. | |
| 5,242,410 A | 9/1993 | Melker | |
| 5,258,042 A | 11/1993 | Mehta | |
| 5,267,940 A | 12/1993 | Moulder | |
| 5,287,861 A | 2/1994 | Wilk | |
| 5,320,613 A | 6/1994 | Houge et al. | |
| 5,330,496 A | 7/1994 | Alferness | |
| 5,334,217 A | 8/1994 | Das | |
| 5,345,940 A | 9/1994 | Seward et al. | |
| 5,354,279 A | 10/1994 | Hofling | |
| 5,366,490 A | 11/1994 | Edwards et al. | |
| 5,373,849 A | 12/1994 | Maroney et al. | |
| 5,419,777 A | 5/1995 | Hofling | |
| 5,423,878 A | 6/1995 | Franz | |
| 5,429,634 A | 7/1995 | Narciso, Jr. | |
| 5,431,700 A | 7/1995 | Sloan | |
| 5,443,497 A | 8/1995 | Venbrux | |
| 5,445,600 A | 8/1995 | Abdulla | |
| 5,445,646 A | 8/1995 | Euteneuer et al. | |
| 5,456,284 A | 10/1995 | Ryan et al. | |
| 5,456,712 A | 10/1995 | Maginot | |
| 5,462,523 A | 10/1995 | Samson et al. | |
| 5,464,395 A | 11/1995 | Faxon et al. | |
| 5,491,224 A | 2/1996 | Bittner et al. | |
| 5,492,304 A | 2/1996 | Smith et al. | |
| 5,496,311 A | 3/1996 | Abele et al. | |
| 5,499,630 A | 3/1996 | Hiki et al. | |
| 5,507,724 A | 4/1996 | Hofmann et al. | |
| 5,507,725 A | 4/1996 | Savage et al. | |
| 5,538,504 A * | 7/1996 | Linden .................. | A61M 25/10 604/264 |
| 5,551,954 A | 9/1996 | Buscemi et al. | |
| 5,554,182 A | 9/1996 | Dinh et al. | |
| 5,556,410 A * | 9/1996 | Mittermeir ............. | A61B 90/39 604/264 |
| 5,570,693 A | 11/1996 | Jang et al. | |
| 5,571,086 A | 11/1996 | Kaplan et al. | |
| 5,571,151 A | 11/1996 | Gregory | |
| 5,588,960 A | 12/1996 | Edwards et al. | |
| 5,597,146 A | 1/1997 | Putman | |
| 5,597,378 A | 1/1997 | Jervis | |
| 5,599,300 A | 2/1997 | Weaver et al. | |
| 5,614,204 A | 3/1997 | Cochrum | |
| 5,628,784 A | 5/1997 | Strecker | |
| 5,661,133 A | 8/1997 | Leiden et al. | |
| 5,662,609 A | 9/1997 | Slepian | |
| 5,662,711 A | 9/1997 | Douglas | |
| 5,665,077 A | 9/1997 | Rosen et al. | |
| 5,669,880 A | 9/1997 | Solar | |
| 5,682,906 A | 11/1997 | Sterman et al. | |
| 5,690,670 A | 11/1997 | Davidson | |
| 5,693,029 A | 12/1997 | Leonhardt | |
| 5,704,361 A | 1/1998 | Seward et al. | |
| 5,704,926 A | 1/1998 | Sutton | |
| 5,713,363 A | 2/1998 | Seward et al. | |
| 5,713,853 A | 2/1998 | Clark et al. | |
| 5,718,725 A | 2/1998 | Sterman et al. | |
| 5,724,975 A | 3/1998 | Negus et al. | |
| 5,724,977 A | 3/1998 | Yock et al. | |
| 5,728,123 A | 3/1998 | Lemelson et al. | |
| 5,735,847 A | 4/1998 | Gough et al. | |
| 5,738,658 A | 4/1998 | Maus et al. | |
| 5,743,874 A | 4/1998 | Fischell et al. | |
| 5,755,682 A | 5/1998 | Knudson et al. | |
| 5,756,696 A | 5/1998 | Gray et al. | |
| 5,771,895 A | 6/1998 | Slager | |
| 5,772,629 A | 6/1998 | Kaplan | |
| 5,772,632 A | 6/1998 | Forman | |
| 5,779,719 A | 7/1998 | Klein et al. | |
| 5,807,258 A | 9/1998 | Cimochowski et al. | |
| 5,807,306 A | 9/1998 | Shapland et al. | |
| 5,810,780 A | 9/1998 | Brimhall et al. | |
| 5,814,005 A | 9/1998 | Barra et al. | |
| 5,827,216 A | 10/1998 | Igo et al. | |
| 5,830,222 A | 11/1998 | Makower | |
| 5,830,224 A | 11/1998 | Cohn et al. | |
| 5,836,913 A | 11/1998 | Orth et al. | |
| 5,843,090 A | 12/1998 | Schuetz | |
| 5,843,170 A | 12/1998 | Ahn | |
| 5,944,738 A | 8/1999 | Amplatz et al. | |
| 5,951,569 A | 9/1999 | Tuckey et al. | |
| 5,954,691 A | 9/1999 | Prosl | |
| 5,957,938 A * | 9/1999 | Zhu ..................... | A61B 17/062 606/222 |
| 5,989,280 A | 11/1999 | Euteneuer et al. | |
| 6,019,788 A | 2/2000 | Butters et al. | |
| 6,042,589 A | 3/2000 | Marianne | |
| 6,048,357 A | 4/2000 | Kontos | |
| 6,053,891 A | 4/2000 | DeCampli | |
| 6,081,738 A | 6/2000 | Hinohara et al. | |
| 6,086,553 A | 7/2000 | Akbik | |
| 6,092,526 A | 7/2000 | LaFontaine et al. | |
| 6,095,878 A | 8/2000 | Van Balen | |
| 6,113,612 A | 9/2000 | Swanson et al. | |
| 6,120,494 A | 9/2000 | Jonkman | |
| 6,120,522 A | 9/2000 | Vrba et al. | |
| 6,120,534 A | 9/2000 | Ruiz | |
| 6,152,937 A | 11/2000 | Peterson et al. | |

(56) References Cited

U.S. PATENT DOCUMENTS

| | | | |
|---|---|---|---|
| 6,165,185 A | 12/2000 | Shennib et al. |
| 6,168,620 B1 | 1/2001 | Kerr |
| 6,168,820 B1 | 1/2001 | Garwood et al. |
| 6,174,681 B1 | 1/2001 | Halling et al. |
| 6,190,353 B1 | 2/2001 | Makower et al. |
| 6,193,734 B1 | 2/2001 | Bolduc et al. |
| 6,196,230 B1 | 3/2001 | Hall et al. |
| 6,217,527 B1 * | 4/2001 | Selmon ............. A61B 17/3207 |
| | | 604/164.11 |
| 6,241,743 B1 | 6/2001 | Levin et al. |
| 6,248,117 B1 | 6/2001 | Blatter |
| 6,251,116 B1 | 6/2001 | Shennib et al. |
| 6,254,631 B1 | 7/2001 | Thompson |
| 6,280,412 B1 | 8/2001 | Pederson, Jr. et al. |
| 6,283,951 B1 | 9/2001 | Flaherty et al. |
| 6,287,280 B1 | 9/2001 | Lampropoulos et al. |
| 6,287,332 B1 | 9/2001 | Bolz et al. |
| 6,290,728 B1 | 9/2001 | Phelps et al. |
| 6,302,875 B1 | 10/2001 | Makower et al. |
| 6,302,892 B1 | 10/2001 | Wilk |
| 6,302,905 B1 | 10/2001 | Goldsteen et al. |
| 6,309,415 B1 | 10/2001 | Pulnev et al. |
| 6,315,752 B1 | 11/2001 | DiMatteo |
| 6,325,798 B1 | 12/2001 | Edwards et al. |
| 6,361,545 B1 | 3/2002 | Macoviak et al. |
| 6,375,615 B1 | 4/2002 | Flaherty et al. |
| 6,387,116 B1 | 5/2002 | McKenzie et al. |
| 6,387,119 B2 | 5/2002 | Wolf et al. |
| 6,391,036 B1 | 5/2002 | Berg et al. |
| 6,402,767 B1 | 6/2002 | Nash et al. |
| 6,443,158 B1 | 9/2002 | LaFontaine et al. |
| 6,451,048 B1 | 9/2002 | Berg et al. |
| 6,458,140 B2 | 10/2002 | Akin et al. |
| 6,464,665 B1 | 10/2002 | Heuser |
| 6,468,303 B1 | 10/2002 | Amplatz et al. |
| 6,475,226 B1 | 11/2002 | Belef et al. |
| 6,494,889 B1 | 12/2002 | Fleischman et al. |
| 6,503,247 B2 | 1/2003 | Swartz et al. |
| 6,506,201 B2 | 1/2003 | Di Caprio et al. |
| 6,508,824 B1 | 1/2003 | Flaherty et al. |
| 6,561,998 B1 | 5/2003 | Roth et al. |
| 6,562,066 B1 | 5/2003 | Martin |
| 6,575,168 B2 | 6/2003 | LaFontaine et al. |
| 6,579,311 B1 | 6/2003 | Makower |
| 6,589,251 B2 | 7/2003 | Yee et al. |
| 6,595,941 B1 | 7/2003 | Blatter |
| 6,602,241 B2 | 8/2003 | Makower et al. |
| 6,613,074 B1 | 9/2003 | Mitelberg et al. |
| 6,616,624 B1 | 9/2003 | Kieval |
| 6,616,675 B1 | 9/2003 | Evard et al. |
| 6,620,202 B2 | 9/2003 | Bottcher et al. |
| 6,623,494 B1 | 9/2003 | Blatter |
| 6,626,920 B2 | 9/2003 | Whayne |
| 6,638,293 B1 | 10/2003 | Makower et al. |
| 6,692,482 B2 | 2/2004 | Heller et al. |
| 6,695,878 B2 | 2/2004 | McGuckin, Jr. et al. |
| 6,699,256 B1 | 3/2004 | Logan et al. |
| 6,702,828 B2 | 3/2004 | Whayne |
| 6,709,414 B2 | 3/2004 | Weitzel et al. |
| 6,709,444 B1 | 3/2004 | Makower |
| 6,712,836 B1 | 3/2004 | Berg et al. |
| 6,719,804 B2 | 4/2004 | St. Pierre |
| 6,726,659 B1 | 4/2004 | Stocking et al. |
| 6,726,677 B1 | 4/2004 | Flaherty et al. |
| 6,736,825 B2 | 5/2004 | Blatter et al. |
| 6,740,426 B2 | 5/2004 | Kawachi et al. |
| 6,743,244 B2 | 6/2004 | Blatter et al. |
| 6,743,259 B2 | 6/2004 | Ginn |
| 6,746,426 B1 | 6/2004 | Flaherty et al. |
| 6,748,484 B1 | 6/2004 | Henderson et al. |
| 6,758,854 B1 | 7/2004 | Butler et al. |
| 6,776,785 B1 | 8/2004 | Yencho et al. |
| 6,797,083 B2 | 9/2004 | Peterson |
| 6,802,858 B2 | 10/2004 | Gambale et al. |
| 6,805,706 B2 | 10/2004 | Solovay et al. |
| 6,808,498 B2 | 10/2004 | Laroya et al. |
| 6,827,698 B1 | 12/2004 | Kleinekofort |
| 6,847,348 B2 | 1/2005 | Rojewski |
| 6,854,172 B2 | 2/2005 | Kaese et al. |
| 6,858,035 B2 | 2/2005 | Whayne |
| 6,869,437 B1 | 3/2005 | Hausen et al. |
| 6,893,413 B2 | 5/2005 | Martin |
| 6,913,600 B2 | 7/2005 | Valley et al. |
| 6,913,607 B2 | 7/2005 | Ainsworth et al. |
| 6,915,154 B1 | 7/2005 | Docherty et al. |
| 6,926,690 B2 | 8/2005 | Renati |
| 6,972,023 B2 | 12/2005 | Whayne et al. |
| 6,979,351 B2 | 12/2005 | Forsell et al. |
| 6,985,774 B2 | 1/2006 | Kieval et al. |
| 7,002,491 B2 | 2/2006 | Robbins |
| 7,008,397 B2 | 3/2006 | Tweden et al. |
| 7,011,094 B2 | 3/2006 | Rapacki et al. |
| 7,011,678 B2 | 3/2006 | Tenerz et al. |
| 7,025,741 B2 | 4/2006 | Cull |
| 7,025,746 B2 | 4/2006 | Tal |
| 7,037,329 B2 | 5/2006 | Martin |
| 7,056,294 B2 | 6/2006 | Khairkhahan et al. |
| 7,056,320 B2 | 6/2006 | Utley et al. |
| 7,056,325 B1 | 6/2006 | Makower et al. |
| 7,077,860 B2 | 7/2006 | Yan et al. |
| 7,083,631 B2 | 8/2006 | Houser et al. |
| 7,108,701 B2 | 9/2006 | Evens et al. |
| 7,115,136 B2 | 10/2006 | Park et al. |
| 7,118,546 B2 | 10/2006 | Blatter |
| 7,128,750 B1 | 10/2006 | Stergiopulos |
| 7,175,644 B2 | 2/2007 | Cooper et al. |
| 7,182,771 B1 | 2/2007 | Houser et al. |
| 7,235,095 B2 | 6/2007 | Haverkost et al. |
| 7,294,115 B1 | 11/2007 | Wilk |
| 7,316,706 B2 | 1/2008 | Bloom et al. |
| 7,317,951 B2 | 1/2008 | Schneider et al. |
| 7,318,804 B2 | 1/2008 | Weitzel et al. |
| 7,326,221 B2 | 2/2008 | Sakamoto et al. |
| 7,331,985 B2 | 2/2008 | Thompson et al. |
| 7,335,220 B2 | 2/2008 | Khosravi et al. |
| 7,351,247 B2 | 4/2008 | Kupiecki et al. |
| 7,361,181 B2 | 4/2008 | Hindrichs et al. |
| 7,374,567 B2 | 5/2008 | Heuser |
| D581,054 S | 11/2008 | Moore |
| 7,462,162 B2 | 12/2008 | Phan et al. |
| 7,476,200 B2 | 1/2009 | Tal |
| 7,530,963 B2 | 5/2009 | Albright |
| 7,563,277 B2 | 7/2009 | Case et al. |
| 7,623,926 B2 | 11/2009 | Rossing et al. |
| 7,625,593 B2 | 12/2009 | Mandrusov et al. |
| 7,628,768 B2 | 12/2009 | Faul et al. |
| D612,499 S | 3/2010 | Ondracek et al. |
| 7,699,863 B2 | 4/2010 | Marco et al. |
| 7,722,549 B2 | 5/2010 | Nakao |
| 7,722,665 B2 | 5/2010 | Anwar et al. |
| 7,744,621 B2 | 6/2010 | Paul et al. |
| 7,794,495 B2 | 9/2010 | Gale et al. |
| 7,807,191 B2 | 10/2010 | Iyer et al. |
| 7,815,590 B2 | 10/2010 | Cooper |
| 7,815,656 B2 | 10/2010 | Rust et al. |
| 7,815,852 B2 | 10/2010 | Sternby |
| 7,828,814 B2 | 11/2010 | Brenneman et al. |
| 7,846,179 B2 | 12/2010 | Belef et al. |
| 7,846,194 B2 | 12/2010 | Hartley et al. |
| 7,850,705 B2 | 12/2010 | Bachinski et al. |
| 7,867,547 B2 | 1/2011 | Tochterman et al. |
| 7,879,367 B2 | 2/2011 | Heublein et al. |
| 7,892,246 B2 | 2/2011 | Akin et al. |
| 7,892,247 B2 | 2/2011 | Conston et al. |
| 7,923,022 B2 | 4/2011 | Wang et al. |
| 7,951,194 B2 | 5/2011 | Gueriguian et al. |
| 7,959,603 B2 | 6/2011 | Wahr et al. |
| 7,964,210 B2 | 6/2011 | Wang et al. |
| 7,967,769 B2 | 6/2011 | Faul et al. |
| 7,972,346 B2 | 7/2011 | Bachmann et al. |
| 8,002,821 B2 | 8/2011 | Stinson |
| 8,016,782 B2 | 9/2011 | Brenneman et al. |
| 8,048,150 B2 | 11/2011 | Weber et al. |
| 8,052,661 B2 | 11/2011 | McGuckin, Jr. et al. |

(56)                    References Cited

U.S. PATENT DOCUMENTS

| | | | |
|---|---|---|---|
| 8,052,751 B2 | 11/2011 | Aklog et al. | |
| 8,057,534 B2 | 11/2011 | Boismier et al. | |
| 8,070,708 B2 | 12/2011 | Rottenberg et al. | |
| 8,088,171 B2 | 1/2012 | Brenneman | |
| 8,089,029 B2 | 1/2012 | Flanagan | |
| 8,091,556 B2 | 1/2012 | Keren et al. | |
| 8,128,689 B2 | 3/2012 | Weber et al. | |
| 8,182,527 B2 | 5/2012 | Llanos et al. | |
| 8,214,015 B2 | 7/2012 | Macaulay et al. | |
| 8,221,495 B2 | 7/2012 | Shrivastava et al. | |
| 8,226,592 B2 | 7/2012 | Brenneman et al. | |
| D665,500 S | 8/2012 | Martin et al. | |
| 8,282,591 B2 | 10/2012 | Khan et al. | |
| 8,308,682 B2 | 11/2012 | Kramer et al. | |
| 8,323,248 B2 | 12/2012 | Morris et al. | |
| 8,357,193 B2 | 1/2013 | Phan et al. | |
| 8,376,979 B2 | 2/2013 | Kapadia | |
| 8,382,697 B2 | 2/2013 | Brenneman et al. | |
| D679,015 S | 3/2013 | Nakaji | |
| 8,409,167 B2 | 4/2013 | Roschak | |
| 8,486,023 B2 | 7/2013 | Pyles | |
| 8,506,984 B2 | 8/2013 | Cook et al. | |
| 8,518,062 B2 | 8/2013 | Cole et al. | |
| 8,518,662 B2 | 8/2013 | Ritzen et al. | |
| 8,545,552 B2 | 10/2013 | Garrison et al. | |
| 8,641,724 B2 | 2/2014 | Brenneman et al. | |
| 8,657,790 B2 | 2/2014 | Tal et al. | |
| D705,427 S | 5/2014 | Jagger et al. | |
| 8,768,487 B2 | 7/2014 | Farnan et al. | |
| 8,784,860 B2 | 7/2014 | Falotico et al. | |
| 8,882,830 B2 | 11/2014 | Cartledge et al. | |
| 8,911,464 B2 | 12/2014 | Kawaura et al. | |
| 8,920,449 B2 | 12/2014 | Wilkinson | |
| 8,926,545 B2 | 1/2015 | Brenneman et al. | |
| 8,932,341 B2 | 1/2015 | Brenneman | |
| D723,166 S | 2/2015 | Igaki et al. | |
| 8,951,276 B2 | 2/2015 | Kellerman et al. | |
| 9,005,155 B2 | 4/2015 | Sugimoto | |
| 9,044,588 B2 | 6/2015 | Conn | |
| 9,061,115 B2 | 6/2015 | Ward et al. | |
| 9,067,050 B2 | 6/2015 | Gallagher et al. | |
| 9,198,756 B2 | 12/2015 | Aklog et al. | |
| 9,232,997 B2 | 1/2016 | Sugimoto et al. | |
| 9,277,995 B2 | 3/2016 | Celermajer et al. | |
| 9,345,485 B2 | 5/2016 | Dakin et al. | |
| 9,439,746 B2 | 9/2016 | Bell et al. | |
| 9,456,812 B2 | 10/2016 | Finch et al. | |
| 9,550,022 B2 | 1/2017 | Brenneman et al. | |
| 9,649,480 B2 | 5/2017 | Sugimoto et al. | |
| 9,681,948 B2 | 6/2017 | Levi et al. | |
| 9,693,800 B2 | 7/2017 | Aman et al. | |
| 9,775,636 B2 | 10/2017 | Fazio et al. | |
| 9,789,294 B2 * | 10/2017 | Taft | A61B 17/3468 |
| 9,814,483 B2 | 11/2017 | Vardi | |
| 9,827,404 B2 | 11/2017 | Nance et al. | |
| 9,839,517 B2 | 12/2017 | Centola et al. | |
| 9,872,981 B2 | 1/2018 | Sparks et al. | |
| 9,980,815 B2 | 5/2018 | Nitzan et al. | |
| 10,292,690 B2 | 5/2019 | Celermajer et al. | |
| 10,327,746 B2 | 6/2019 | Glimsdale et al. | |
| 10,426,482 B2 | 10/2019 | Rafiee et al. | |
| 10,426,497 B2 | 10/2019 | Chou et al. | |
| 10,433,851 B2 | 10/2019 | Adams et al. | |
| 10,543,113 B2 | 1/2020 | Vong et al. | |
| 10,561,423 B2 | 2/2020 | Sharma | |
| 10,565,835 B2 | 2/2020 | Harrington et al. | |
| 10,568,751 B2 | 2/2020 | McNamara | |
| 10,595,999 B2 | 3/2020 | Vettukattil et al. | |
| 10,709,451 B2 | 7/2020 | Gronberg et al. | |
| 10,835,394 B2 | 11/2020 | Nae et al. | |
| 10,898,698 B1 | 1/2021 | Eigler et al. | |
| 10,912,585 B2 | 2/2021 | Kleyman | |
| 10,925,756 B2 | 2/2021 | Perszyk | |
| 10,940,296 B2 | 3/2021 | Keren | |
| 11,135,054 B2 | 10/2021 | Nitzan et al. | |
| 11,234,702 B1 | 2/2022 | Eigler et al. | |
| 11,291,807 B2 | 4/2022 | Eigler et al. | |
| 11,298,117 B2 | 4/2022 | Hariton et al. | |
| 11,304,698 B2 | 4/2022 | Sharma | |
| 11,395,644 B2 | 7/2022 | Alanbaei | |
| 2001/0025643 A1 | 10/2001 | Foley | |
| 2001/0035183 A1 | 11/2001 | Sexton et al. | |
| 2001/0045698 A1 | 11/2001 | Lo | |
| 2002/0013616 A1 | 1/2002 | Carter et al. | |
| 2002/0029079 A1 | 3/2002 | Kim et al. | |
| 2002/0062146 A1 | 5/2002 | Makower et al. | |
| 2002/0128546 A1 | 9/2002 | Silver | |
| 2002/0138009 A1 | 9/2002 | Brockway et al. | |
| 2002/0169466 A1 | 11/2002 | Peterson et al. | |
| 2002/0193751 A1 | 12/2002 | Theeuwes et al. | |
| 2002/0198501 A1 | 12/2002 | Kumar et al. | |
| 2003/0017150 A1 | 1/2003 | Torphy | |
| 2003/0060876 A1 | 3/2003 | Loshakove et al. | |
| 2003/0065345 A1 | 4/2003 | Weadock | |
| 2003/0181928 A1 | 9/2003 | Vidlund et al. | |
| 2003/0225425 A1 | 12/2003 | Kupiecki et al. | |
| 2004/0064081 A1 | 4/2004 | Stanish | |
| 2004/0082738 A1 | 4/2004 | Dolle et al. | |
| 2004/0087997 A1 | 5/2004 | Brenneman | |
| 2004/0092879 A1 | 5/2004 | Kraus et al. | |
| 2004/0097974 A1 * | 5/2004 | De Leval | A61B 17/0469 |
| | | | 606/144 |
| 2004/0098105 A1 | 5/2004 | Stinson et al. | |
| 2004/0127941 A1 * | 7/2004 | Cunningham | A61B 17/06066 |
| | | | 606/223 |
| 2004/0158143 A1 | 8/2004 | Flaherty et al. | |
| 2004/0215168 A1 | 10/2004 | Verrier et al. | |
| 2004/0215220 A1 | 10/2004 | Dolan et al. | |
| 2004/0215323 A1 | 10/2004 | Stiger | |
| 2004/0230156 A1 | 11/2004 | Schreck et al. | |
| 2004/0260318 A1 | 12/2004 | Hunter et al. | |
| 2005/0021085 A1 | 1/2005 | Abrams et al. | |
| 2005/0033239 A1 | 2/2005 | Argentine | |
| 2005/0038501 A1 | 2/2005 | Moore et al. | |
| 2005/0043708 A1 | 2/2005 | Gleeson et al. | |
| 2005/0049675 A1 | 3/2005 | Wallace | |
| 2005/0060041 A1 | 3/2005 | Phan et al. | |
| 2005/0065469 A1 | 3/2005 | Tal | |
| 2005/0075655 A1 | 4/2005 | Bumbalough et al. | |
| 2005/0075656 A1 | 4/2005 | Beaupre | |
| 2005/0082226 A1 | 4/2005 | Bene et al. | |
| 2005/0107723 A1 | 5/2005 | Wehman et al. | |
| 2005/0149096 A1 | 7/2005 | Hilal et al. | |
| 2005/0165344 A1 | 7/2005 | Dobak | |
| 2005/0228402 A1 | 10/2005 | Hofmann | |
| 2005/0249770 A1 | 11/2005 | Hunter | |
| 2005/0249776 A1 | 11/2005 | Chen et al. | |
| 2005/0267490 A1 | 12/2005 | Secrest et al. | |
| 2005/0272806 A1 | 12/2005 | Falotico et al. | |
| 2005/0277965 A1 | 12/2005 | Brenneman et al. | |
| 2006/0020324 A1 | 1/2006 | Schmid et al. | |
| 2006/0024359 A1 | 2/2006 | Walker et al. | |
| 2006/0034466 A1 | 2/2006 | Form et al. | |
| 2006/0041270 A1 | 2/2006 | Lenker et al. | |
| 2006/0074398 A1 | 4/2006 | Whiting et al. | |
| 2006/0111704 A1 | 5/2006 | Brenneman et al. | |
| 2006/0130591 A1 | 6/2006 | Perkins | |
| 2006/0130767 A1 | 6/2006 | Herchen | |
| 2006/0182536 A1 | 8/2006 | Rice et al. | |
| 2006/0198869 A1 | 9/2006 | Furst et al. | |
| 2006/0264801 A1 | 11/2006 | Bolling et al. | |
| 2006/0265042 A1 | 11/2006 | Catanese et al. | |
| 2006/0271196 A1 | 11/2006 | Saal et al. | |
| 2006/0293701 A1 | 12/2006 | Ainsworth et al. | |
| 2007/0021730 A1 | 1/2007 | Flaherty et al. | |
| 2007/0083258 A1 | 4/2007 | Falotico et al. | |
| 2007/0173787 A1 | 7/2007 | Huang et al. | |
| 2007/0179426 A1 | 8/2007 | Selden | |
| 2007/0213750 A1 | 9/2007 | Weadock | |
| 2008/0021485 A1 | 1/2008 | Catanese et al. | |
| 2008/0027532 A1 | 1/2008 | Boylan et al. | |
| 2008/0051883 A1 | 2/2008 | Llanos et al. | |
| 2008/0071178 A1 | 3/2008 | Greenland et al. | |
| 2008/0091264 A1 | 4/2008 | Machold et al. | |

(56) References Cited

U.S. PATENT DOCUMENTS

| | | | |
|---|---|---|---|
| 2008/0109069 A1 | 5/2008 | Coleman et al. | |
| 2008/0161904 A1 | 7/2008 | Heuser et al. | |
| 2008/0167595 A1 | 7/2008 | Porter et al. | |
| 2008/0215033 A1* | 9/2008 | Miller | A61B 17/3478 |
| | | | 604/509 |
| 2008/0234842 A1 | 9/2008 | Zhang | |
| 2008/0306359 A1 | 12/2008 | Zdeblick et al. | |
| 2009/0005656 A1 | 1/2009 | Najafi et al. | |
| 2009/0105654 A1 | 4/2009 | Kurth et al. | |
| 2009/0105724 A1 | 4/2009 | Yoshizaki et al. | |
| 2009/0125097 A1 | 5/2009 | Bruszewski et al. | |
| 2009/0143713 A1 | 6/2009 | Van Dam et al. | |
| 2009/0149947 A1 | 6/2009 | Frohwitter | |
| 2009/0187116 A1 | 7/2009 | Noishiki et al. | |
| 2009/0234293 A1 | 9/2009 | Albrecht et al. | |
| 2009/0281379 A1 | 11/2009 | Binmoeller et al. | |
| 2010/0016797 A1 | 1/2010 | Rockrohr | |
| 2010/0030321 A1 | 2/2010 | Mach | |
| 2010/0057048 A1 | 3/2010 | Eldredge | |
| 2010/0106171 A1 | 4/2010 | Arepally et al. | |
| 2010/0198041 A1 | 8/2010 | Christian et al. | |
| 2010/0217382 A1 | 8/2010 | Chau et al. | |
| 2010/0298930 A1 | 11/2010 | Orlov | |
| 2011/0096036 A1 | 4/2011 | McIntosh et al. | |
| 2011/0106118 A1 | 5/2011 | Son et al. | |
| 2011/0251482 A1 | 10/2011 | Kellerman et al. | |
| 2011/0306916 A1 | 12/2011 | Nitzan et al. | |
| 2011/0306988 A1* | 12/2011 | Robertson | A61B 17/06109 |
| | | | 606/139 |
| 2012/0029598 A1 | 2/2012 | Zhao | |
| 2012/0041544 A1 | 2/2012 | Wolf | |
| 2012/0053686 A1 | 3/2012 | McNamara et al. | |
| 2012/0108986 A1 | 5/2012 | Beasley et al. | |
| 2012/0143141 A1 | 6/2012 | Verkaik et al. | |
| 2012/0265229 A1 | 10/2012 | Rottenberg et al. | |
| 2012/0265296 A1 | 10/2012 | McNamara et al. | |
| 2013/0022214 A1 | 1/2013 | Dickins et al. | |
| 2013/0030521 A1 | 1/2013 | Nitzan et al. | |
| 2013/0178784 A1 | 7/2013 | McNamara et al. | |
| 2013/0225997 A1 | 8/2013 | Dillard et al. | |
| 2013/0253342 A1 | 9/2013 | Griswold et al. | |
| 2013/0281988 A1 | 10/2013 | Magnin et al. | |
| 2013/0310804 A1 | 11/2013 | Jabba et al. | |
| 2014/0094836 A1* | 4/2014 | Feng | A61B 17/3403 |
| | | | 606/185 |
| 2014/0183828 A1 | 7/2014 | Xu et al. | |
| 2014/0203939 A1 | 7/2014 | Harrington et al. | |
| 2014/0222040 A1 | 8/2014 | Park et al. | |
| 2014/0276395 A1 | 9/2014 | Wilson et al. | |
| 2014/0277054 A1 | 9/2014 | McNamara et al. | |
| 2014/0278442 A1 | 9/2014 | Hong et al. | |
| 2014/0350523 A1 | 11/2014 | Dehdashtian et al. | |
| 2015/0119796 A1 | 4/2015 | Finch | |
| 2015/0148731 A1 | 5/2015 | McNamara et al. | |
| 2015/0151101 A1 | 6/2015 | Bonnette et al. | |
| 2015/0238729 A1 | 8/2015 | Jenson et al. | |
| 2015/0265311 A1* | 9/2015 | Takahashi | A61B 17/062 |
| | | | 600/30 |
| 2016/0022293 A1 | 1/2016 | Dubrul et al. | |
| 2016/0022970 A1 | 1/2016 | Forcucci et al. | |
| 2016/0045165 A1 | 2/2016 | Braido et al. | |
| 2016/0058452 A1 | 3/2016 | Brenneman et al. | |
| 2016/0120550 A1 | 5/2016 | McNamara et al. | |
| 2016/0151615 A1 | 6/2016 | Overtoom | |
| 2016/0220357 A1 | 8/2016 | Anand et al. | |
| 2016/0270810 A1 | 9/2016 | Vardi et al. | |
| 2016/0296317 A1 | 10/2016 | Timmermans et al. | |
| 2016/0323977 A1 | 11/2016 | Sun et al. | |
| 2016/0331468 A1 | 11/2016 | Lee et al. | |
| 2016/0338823 A1 | 11/2016 | Akingba | |
| 2017/0090865 A1 | 3/2017 | Armstrong-Muntner et al. | |
| 2017/0100141 A1 | 4/2017 | Morero et al. | |
| 2017/0105839 A1 | 4/2017 | Subramanian et al. | |
| 2017/0113026 A1 | 4/2017 | Finch | |
| 2017/0128705 A1 | 5/2017 | Forcucci et al. | |
| 2017/0196565 A1 | 7/2017 | Tuseth et al. | |
| 2017/0258585 A1 | 9/2017 | Marquez et al. | |
| 2017/0303959 A1 | 10/2017 | Feng et al. | |
| 2017/0319823 A1 | 11/2017 | Yacoby et al. | |
| 2017/0340460 A1 | 11/2017 | Rosen et al. | |
| 2018/0035971 A1 | 2/2018 | Brenner et al. | |
| 2018/0140444 A1 | 5/2018 | Neuss et al. | |
| 2018/0177516 A1 | 6/2018 | Vardi et al. | |
| 2018/0185153 A1 | 7/2018 | Bishop et al. | |
| 2018/0207412 A1 | 7/2018 | Malek et al. | |
| 2018/0214269 A1 | 8/2018 | Wilson et al. | |
| 2018/0243071 A1 | 8/2018 | Eigler et al. | |
| 2018/0256865 A1 | 9/2018 | Finch et al. | |
| 2019/0076186 A1* | 3/2019 | Fischell | A61B 18/1492 |
| 2019/0083228 A1 | 3/2019 | Dickinson et al. | |
| 2019/0134349 A1* | 5/2019 | Cohn | A61M 25/0021 |
| 2019/0134350 A1 | 5/2019 | Crisco et al. | |
| 2019/0269392 A1 | 9/2019 | Celermajer et al. | |
| 2019/0298909 A1 | 10/2019 | Cully et al. | |
| 2019/0336339 A1 | 11/2019 | Reo et al. | |
| 2019/0351210 A1 | 11/2019 | Solomon et al. | |
| 2020/0054867 A1 | 2/2020 | Schwartz et al. | |
| 2020/0085600 A1 | 3/2020 | Schwartz et al. | |
| 2020/0101270 A1 | 4/2020 | Sutherland | |
| 2020/0170662 A1 | 6/2020 | Vardi et al. | |
| 2020/0187945 A1 | 6/2020 | Rowe et al. | |
| 2020/0230362 A1 | 7/2020 | Basude | |
| 2020/0254228 A1 | 8/2020 | Taft et al. | |
| 2020/0261704 A1 | 8/2020 | Wang et al. | |
| 2020/0268379 A1* | 8/2020 | Cichocki, Jr. | A61B 17/06066 |
| 2020/0289196 A1 | 9/2020 | Arevalos et al. | |
| 2020/0315599 A1 | 10/2020 | Nae et al. | |
| 2020/0368505 A1 | 11/2020 | Nae et al. | |
| 2020/0391016 A1 | 12/2020 | Passman et al. | |
| 2021/0000581 A9 | 1/2021 | Eigler et al. | |
| 2021/0007790 A1 | 1/2021 | Takahashi et al. | |
| 2021/0007791 A1 | 1/2021 | Takahashi et al. | |
| 2021/0007800 A1 | 1/2021 | Takahashi et al. | |
| 2021/0022855 A1 | 1/2021 | Tegels et al. | |
| 2021/0045691 A1 | 2/2021 | Zou et al. | |
| 2021/0052877 A1 | 2/2021 | Muldoon et al. | |
| 2021/0059650 A1 | 3/2021 | Eidenschink et al. | |
| 2021/0077186 A1 | 3/2021 | Pate et al. | |
| 2021/0085935 A1 | 3/2021 | Fahey et al. | |
| 2021/0092522 A1 | 3/2021 | Draper et al. | |
| 2021/0113824 A1 | 4/2021 | Chng et al. | |
| 2021/0121179 A1 | 4/2021 | Ben-David et al. | |
| 2021/0137635 A1 | 5/2021 | Gomez et al. | |
| 2021/0153776 A1 | 5/2021 | Minar et al. | |
| 2021/0161637 A1 | 6/2021 | Eigler et al. | |
| 2021/0177508 A1 | 6/2021 | Kellerman | |
| 2021/0213269 A1 | 7/2021 | Venskytis et al. | |
| 2021/0236138 A1 | 8/2021 | Perszyk et al. | |
| 2021/0259671 A1 | 8/2021 | DiCicco et al. | |
| 2021/0290214 A1 | 9/2021 | Cole et al. | |
| 2021/0361238 A1 | 11/2021 | Bak-Boychuk et al. | |
| 2021/0369321 A1 | 12/2021 | Yang et al. | |
| 2021/0401494 A1 | 12/2021 | Passman et al. | |
| 2022/0001154 A1 | 1/2022 | Rowe et al. | |
| 2022/0008014 A1 | 1/2022 | Rowe et al. | |
| 2022/0031327 A1 | 2/2022 | Manash et al. | |
| 2022/0039667 A1 | 2/2022 | Schmitt et al. | |
| 2022/0039671 A1 | 2/2022 | Fahey | |
| 2022/0039833 A1 | 2/2022 | Thai et al. | |
| 2022/0088355 A1 | 3/2022 | Rabito et al. | |
| 2022/0096087 A1 | 3/2022 | Valdez | |
| 2022/0110679 A1 | 4/2022 | Wang et al. | |
| 2022/0142652 A1 | 5/2022 | Alexander et al. | |
| 2022/0151784 A1 | 5/2022 | Eigler et al. | |
| 2022/0168015 A1 | 6/2022 | Murray et al. | |
| 2022/0184356 A1 | 6/2022 | Nae et al. | |
| 2022/0203077 A1 | 6/2022 | Folan | |
| 2022/0203078 A1 | 6/2022 | May | |
| 2022/0211380 A1 | 7/2022 | Pate | |
| 2022/0218352 A1 | 7/2022 | O'Halloran et al. | |
| 2022/0218964 A1 | 7/2022 | Fahey et al. | |
| 2022/0241564 A1 | 8/2022 | Shang et al. | |
| 2022/0241565 A1 | 8/2022 | Nae et al. | |
| 2022/0249285 A1 | 8/2022 | Chang et al. | |

(56) References Cited

U.S. PATENT DOCUMENTS

| | | |
|---|---|---|
| 2022/0257904 A1 | 8/2022 | Passman et al. |
| 2022/0273279 A1 | 9/2022 | Valdez et al. |
| 2022/0280160 A1 | 9/2022 | Sharma |
| 2022/0280760 A1 | 9/2022 | Thai et al. |
| 2022/0296865 A1 | 9/2022 | Rafiee et al. |
| 2022/0313234 A1 | 10/2022 | McNamara et al. |
| 2022/0323012 A1 | 10/2022 | Pool et al. |
| 2022/0323196 A1 | 10/2022 | Rafiee et al. |
| 2022/0346936 A1 | 11/2022 | Scutti et al. |
| 2022/0347446 A1 | 11/2022 | Fahey et al. |
| 2022/0370120 A1 | 11/2022 | Yang et al. |
| 2022/0379100 A1 | 12/2022 | Gutierrez et al. |
| 2022/0387009 A1 | 12/2022 | Bukhdruker et al. |
| 2023/0099410 A1 | 3/2023 | Primeaux |
| 2023/0165672 A1 | 6/2023 | Fahey et al. |
| 2023/0181214 A1 | 6/2023 | Vardi et al. |
| 2023/0191093 A1 | 6/2023 | Nae et al. |
| 2023/0233255 A1 | 7/2023 | Takahashi |
| 2023/0263949 A1 | 8/2023 | Passman et al. |
| 2023/0285133 A1 | 9/2023 | Eigler et al. |
| 2023/0330398 A1 | 10/2023 | Nae et al. |
| 2023/0404659 A1 | 12/2023 | Akerele-Ale et al. |
| 2024/0000404 A1 | 1/2024 | Robertson et al. |

FOREIGN PATENT DOCUMENTS

| | | | |
|---|---|---|---|
| CN | 113397762 A | 9/2021 | |
| EP | 2716242 A1 | 4/2014 | |
| EP | 2459077 B1 * | 8/2017 | ......... A61B 17/0482 |
| JP | H02241446 A | 9/1990 | |
| KR | 20200145957 A | 12/2020 | |
| WO | WO-2000018323 A2 | 4/2000 | |
| WO | WO-2004082738 A2 | 9/2004 | |
| WO | WO-2005006963 A2 | 1/2005 | |
| WO | WO-2014150106 A1 | 9/2014 | |
| WO | WO-2015052235 A1 | 4/2015 | |
| WO | WO-2016009337 A2 | 1/2016 | |
| WO | WO-2016059638 A1 | 4/2016 | |
| WO | WO-2017062858 A1 | 4/2017 | |
| WO | WO-2019035993 A1 | 2/2019 | |
| WO | WO-2020215090 A1 | 10/2020 | |
| WO | WO-2020232384 A1 | 11/2020 | |
| WO | WO-2021091566 A1 | 5/2021 | |
| WO | WO-2022031317 A1 | 2/2022 | |
| WO | WO-2022060630 A1 | 3/2022 | |
| WO | WO-2022071179 A1 | 4/2022 | |
| WO | WO-2022133070 A1 | 6/2022 | |
| WO | WO-2022169865 A1 | 8/2022 | |
| WO | WO-2022177737 A1 | 8/2022 | |
| WO | WO-2022197454 A1 | 9/2022 | |
| WO | WO-2022197455 A1 | 9/2022 | |
| WO | WO-2022232133 A1 | 11/2022 | |
| WO | WO-2022246158 A1 | 11/2022 | |
| WO | WO-2022246166 A1 | 11/2022 | |
| WO | WO-2022271473 A1 | 12/2022 | |
| WO | WO-2023022883 A1 | 2/2023 | |
| WO | WO-2023027926 A1 | 3/2023 | |
| WO | WO-2023079498 A1 | 5/2023 | |
| WO | WO-2023081127 A1 | 5/2023 | |
| WO | WO-2023081129 A1 | 5/2023 | |
| WO | WO-2023154235 A1 | 8/2023 | |
| WO | WO-2023154308 A1 | 8/2023 | |
| WO | WO-2023172435 A1 | 9/2023 | |
| WO | WO-2023172436 A1 | 9/2023 | |
| WO | WO-2023196243 A1 | 10/2023 | |
| WO | WO-2023239784 A1 | 12/2023 | |
| WO | WO-2023239785 A1 | 12/2023 | |
| WO | WO-2023239788 A2 | 12/2023 | |
| WO | WO-2024076579 A1 | 4/2024 | |

OTHER PUBLICATIONS

Chao-Chi Y., et al., "Fabrication of a Flexible Wireless Pressure Sensor for Intravascular Blood Pressure Monitoring," Microelectronic Engineering Elsevier Publishers Bv, Amsterdam, NL, Apr. 11, 2019, vol. 213, pp. 55-61, ISSN 0167-9317, XP085679189, Retrieved from URL: http://dx.doi.Org/10.1016/j.mee.2019.04.009.

Kong H., et al., "Creation Of An Intra-atrial Communication With A New Amplatzer Shunt Prosthesis: Preliminary Resultsin a Swinw Model," Catheterization and Cardiovascular Interventions, 2002, vol. 56, pp. 267-271.

Kong P.K., et al., "Unroofed Coronary Sinus and Persistent Left Superior Vena Cava," The European Society of Cardiology, 2006, pp. 398-401.

Mantini E., MD, et al., "Congenital Anomalies Involving the Coronary Sinus," Circulation, Journal of the American Heart Association, Feb. 1966, vol. 33, pp. 317-327.

Ruebben A., etaL, "Arteriovenous Fistulas Induced by Femoral Arterial Catheterization: Percutaneous Treatment," Radiology, Dec. 1998, vol. 209, No. 3, pp. 729-734.

Scheller V., et al., "Coronary Sinus to Left Atrial Communication," Case Report in Medicine, Ohio Heart and Vascular Center, 2009, vol. 2009, Article ID 790715, 4 Pages.

* cited by examiner

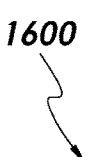

1600

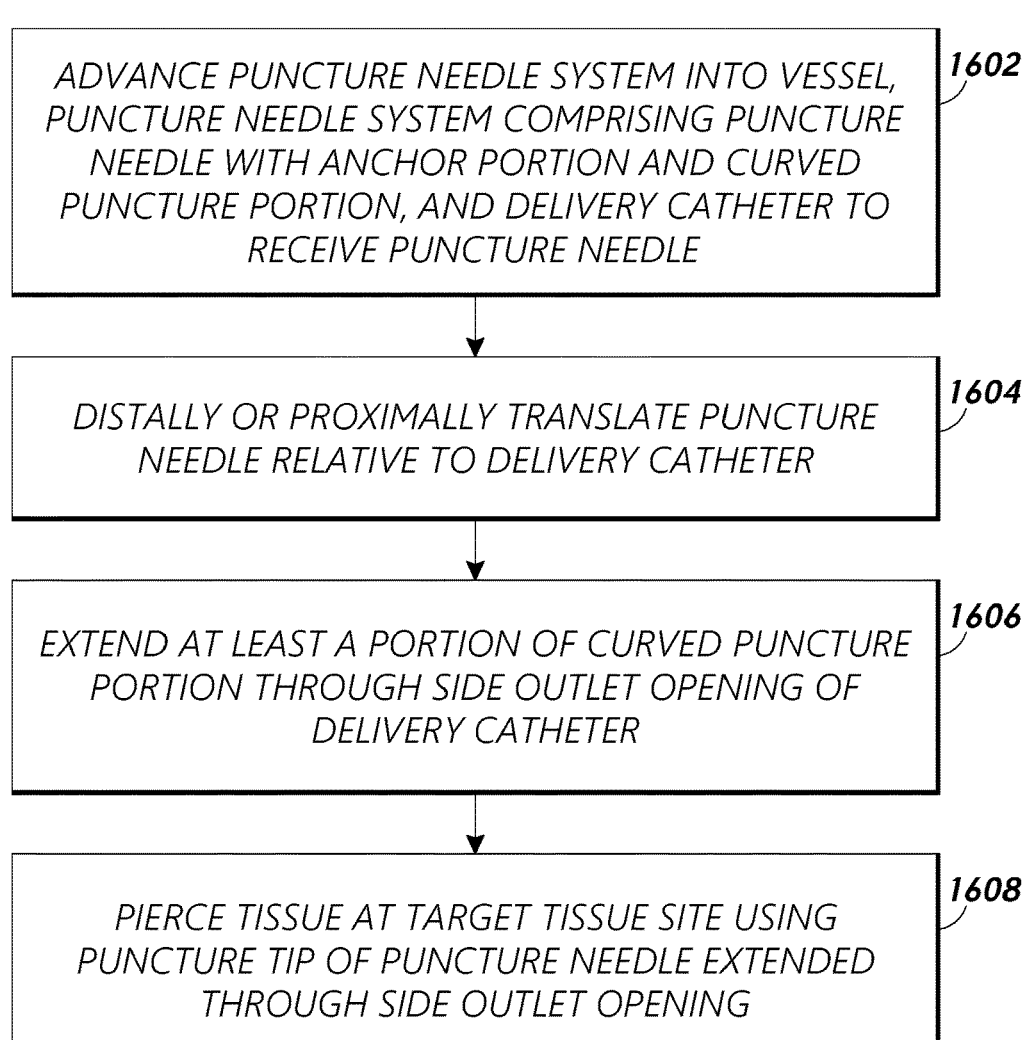

ADVANCE PUNCTURE NEEDLE SYSTEM INTO VESSEL, PUNCTURE NEEDLE SYSTEM COMPRISING PUNCTURE NEEDLE WITH ANCHOR PORTION AND CURVED PUNCTURE PORTION, AND DELIVERY CATHETER TO RECEIVE PUNCTURE NEEDLE

1602

DISTALLY OR PROXIMALLY TRANSLATE PUNCTURE NEEDLE RELATIVE TO DELIVERY CATHETER

1604

EXTEND AT LEAST A PORTION OF CURVED PUNCTURE PORTION THROUGH SIDE OUTLET OPENING OF DELIVERY CATHETER

1606

PIERCE TISSUE AT TARGET TISSUE SITE USING PUNCTURE TIP OF PUNCTURE NEEDLE EXTENDED THROUGH SIDE OUTLET OPENING

TRANSCATHETER PUNCTURE NEEDLE SYSTEM

CROSS REFERENCE TO RELATED APPLICATIONS

This application is a continuation application of PCT International Patent Application Serial No. PCT/US2020/050623, filed Sep. 14, 2020 and entitled TRANSCATHETER PUNCTURE NEEDLE SYSTEM, which claims the priority based on U.S. Provisional Patent Application Ser. No. 62/902,747, filed Sep. 19, 2019 and entitled TRANSCATHETER PUNCTURE NEEDLE SYSTEM, the complete disclosures of both of which are hereby incorporated by reference herein in their entireties.

BACKGROUND

Field

This disclosure generally relates to the field of transcatheter puncture needles used in the delivery of medical implant devices and/or therapies.

Description of Related Art

Transcatheter delivery of a puncture needle to a target vessel, channel, chamber and/or organ can be performed in minimally invasive procedures to form an opening at a target tissue site. The opening can be formed such that medical implant devices and/or therapies can be provided to the target tissue site. For example, delivery of implant devices and/or therapies to the heart can be performed for treatment of elevated pressure in the left atrium.

SUMMARY

Described herein are devices, systems, and methods relating to transcatheter puncture needles. The puncture needles can be used in minimally invasive procedures for forming openings at target tissue sites, including on a left atrial wall within the heart.

In some implementations, a puncture needle can comprise a puncture tip configured to pierce tissue, and an elongate portion. The elongate portion can comprise a distal portion comprising a curved puncture portion having a first end associated with the puncture tip, and extending from the first end to a first bend having a first acute angle oriented distally; a first distal elongate portion, the first distal elongate portion meeting the curved puncture portion at the first bend, and the first distal elongate portion extending from the first bend to a second bend having a second acute angle oriented proximally; and a second distal elongate portion, the first distal elongate portion and the second distal elongate portion meeting at the second bend, and the second distal elongate portion extending proximally from the second bend. The second bend can be distal of the curved puncture portion.

In some embodiments, the first distal elongate portion, the second distal elongate portion and the curved puncture portion are in one plane. In some embodiments, the elongate portion is a single wire.

In some embodiments, the first distal elongate portion comprises a first distal curved portion and the second distal elongate portion comprises a second distal curved portion, the first distal curved portion and the second distal curved portion having a same orientation as the curved puncture portion. In some embodiments, a radius of curvature the curved puncture portion is smaller than that of each of the first distal curved portion and the second distal curved portion.

In some implementations, a puncture needle can comprise a puncture tip configured to pierce tissue, and an elongate portion comprising a distal portion, the distal portion comprising a curved distal elongate portion and a curved puncture portion extending from the curved distal elongate portion to the puncture tip. The curved distal elongate portion and the curved puncture portion can have a same orientation. A distal end of the curved distal elongate portion can be distal of the curved puncture portion.

In some embodiments, a radius of curvature of the curved distal elongate portion is greater than that of the curved puncture portion.

In some implementations, a puncture needle can comprise a puncture tip configured to pierce tissue, and a distal portion. The distal portion can comprise an anchor portion, and a curved puncture portion comprising a first end associated with the puncture tip and a second end coupled to the anchor portion. The anchor portion can comprise a portion distal of the curved puncture portion.

In some embodiments, the curved puncture portion is proximally oriented, and wherein the puncture tip points proximally. In some embodiments, the curved puncture portion is distally oriented, and wherein the puncture tip points distally.

In some embodiments, the curved puncture portion comprises a segment of a circle. In some embodiments, the curved puncture portion comprises a semi-circle.

In some embodiments, the distal portion comprises a lateral cross-section having a rectangular shape, the lateral cross-section being taken along a plane perpendicular to a longitudinal axis of the puncture needle.

In some embodiments, the anchor portion is a curved anchor portion, the curved anchor portion comprising the portion distal of the curved puncture portion, and a proximal portion coupled to the second end of the curved puncture portion. In some embodiments, the curved anchor portion and the curved puncture portion comprise a same orientation. In some embodiments, a radius of curvature of the curved puncture portion is smaller than that of the curved anchor portion. In some embodiments, the curved anchor portion comprises a shape configured to conform to a curvature along a length of a coronary sinus.

In some embodiments, the anchor portion can comprise a first anchor portion comprising a first end and a second end, wherein the first end of the first anchor portion is coupled to the curved puncture portion; and a second anchor portion comprising a first end coupled to the second end of the first anchor portion, and wherein the second anchor portion extends proximally from the first end of the second anchor portion. The first anchor portion and the second anchor portion can meet at a bend, where the bend can be proximally oriented and the bend can be distal of the curved puncture portion. In some embodiments, the bend comprises an acute angle.

In some embodiments, the curved puncture portion, the first anchor portion, and the second anchor portion are in one plane. In some embodiments, the first anchor portion is a first curved anchor portion and the second anchor portion is a second curved anchor portion. In some embodiments, the curved puncture portion, the first curved anchor portion, and the second curved anchor portion comprise a same orientation. In some embodiments, a radius of curvature of the curved puncture portion is smaller than that of each of the first curved anchor portion and the second curved anchor portion. In some embodiments, the first curved anchor portion and second curved anchor portion each comprise a shape configured to conform to a curvature along a length of a coronary sinus.

In some embodiments, the first anchor portion and the second anchor portion are each linear portions. In some embodiments, the curved puncture portion is proximally oriented, wherein the curved puncture portion and the first end of the first anchor portion meet at a distally oriented first bend, wherein the first anchor portion and the second anchor portion meet at a proximally oriented second bend.

In some implementations, a puncture needle system can comprise a puncture needle and a delivery catheter. The puncture needle can comprise a puncture tip and a distal portion. The distal portion can comprise an anchor portion, and a curved puncture portion comprising a first end associated with the puncture tip and a second end coupled to the anchor portion, the anchor portion comprising a portion distal of the curved puncture portion. The delivery catheter can comprise a lumen, the puncture needle extending through the lumen, and a side outlet opening on a distal portion of the delivery catheter configured to allow extension therethrough of at least a portion of the curved puncture portion, wherein the anchor portion extends through a distal portion of the lumen distal of the side outlet opening.

In some embodiments, the distal portion of the lumen distal of the side outlet opening comprises a lateral cross section comprising a non-circular shape, the lateral cross section being taken along a plane perpendicular to a longitudinal axis of the delivery catheter. In some embodiments, the lateral cross-section of the distal portion of the lumen comprises a same shape as a lateral cross section of the anchor portion.

In some embodiments, the system comprises a medical implant guide wire sheath configured to slidably receive a medical implant guide wire, the medical implant guide wire sheath comprising a distal portion coupled to at least a portion of the curved puncture portion.

In some embodiments, the anchor portion is a curved anchor portion, the curved anchor portion comprising the portion distal of the curved puncture portion, and a proximal portion coupled to the second end of the curved puncture portion.

In some embodiments, the anchor portion comprises a first anchor portion comprising a first end and a second end, wherein the first end of the first anchor portion is coupled to the curved puncture portion; and a second anchor portion comprising a first end coupled to the second end of the first anchor portion, and wherein the second anchor portion extends proximally from the first end of the second anchor portion. The first anchor portion and the second anchor portion can meet at a bend, and wherein the bend is proximally oriented and the bend is distal of the curved puncture portion.

In some embodiments, the curved puncture portion, the first anchor portion, and the second anchor portion are in one plane.

In some embodiments, the first anchor portion is a first curved anchor portion and the second anchor portion is a second curved anchor portion, wherein the curved puncture portion, the first curved anchor portion, and the second curved anchor portion comprise a same orientation.

In some embodiments, the first anchor portion and the second anchor portion are each linear portions.

In some embodiments, while the puncture needle is in a retracted state, the puncture tip is configured to be proximal of the side outlet opening and the anchor portion comprises a portion extending along the lumen past the side outlet opening and through the portion of the lumen distal of the side outlet opening.

In some embodiments, while the puncture needle is in a retracted state, the puncture tip is configured to be distal of the side outlet opening and the anchor portion extends distally through the portion of the lumen distal of the side outlet opening.

In some implementations, a method for delivering a puncture needle can comprise advancing a puncture needle system into a vessel. The puncture needle system can comprise a puncture needle and a delivery catheter. The puncture needle can comprise a distal portion, the distal portion comprising an anchor portion and a curved puncture portion comprising a first end associated with a puncture tip and a second end coupled to the anchor portion, the anchor portion comprising a portion distal of the curved puncture portion. The delivery catheter can comprise a puncture needle lumen, the puncture needle extending slidably through the puncture needle lumen, and a side outlet opening on a portion of the delivery catheter configured to allow extension therethrough of at least a portion of the curved puncture portion. The method can comprise one of distally or proximally translating the puncture needle relative to the delivery catheter to release at least a portion of the curved puncture portion through the side outlet opening; and piercing tissue at a target tissue site to form an opening at the target tissue site using the puncture tip extended through the side outlet opening.

In some embodiments, the system further comprises a medical implant guide wire sheath configured to slidably receive a medical implant guide wire, the medical implant guide wire sheath comprising a distal portion coupled to at least a portion of the curved puncture portion, the method further comprising advancing the medical implant guide wire within the medical implant guide wire sheath and through an opening associated with a distal end of the medical implant guide wire sheath into the opening formed at the target tissue site.

In some embodiments, advancing the puncture needle system into the vessel comprises advancing the puncture needle system into a coronary sinus. In some embodiments, piercing tissue at the target tissue site comprises piercing tissue on a left atrial wall.

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. However, it should be understood that the use of similar reference numbers in connection with multiple drawings does not necessarily imply similarity between respective embodiments associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some embodiments or configurations.

FIG. 15 is a flow diagram of an example of a process to deploy a puncture needle system for piercing tissue at a target tissue site, in accordance with one or more embodiments.

DETAILED DESCRIPTION

Figure 1:
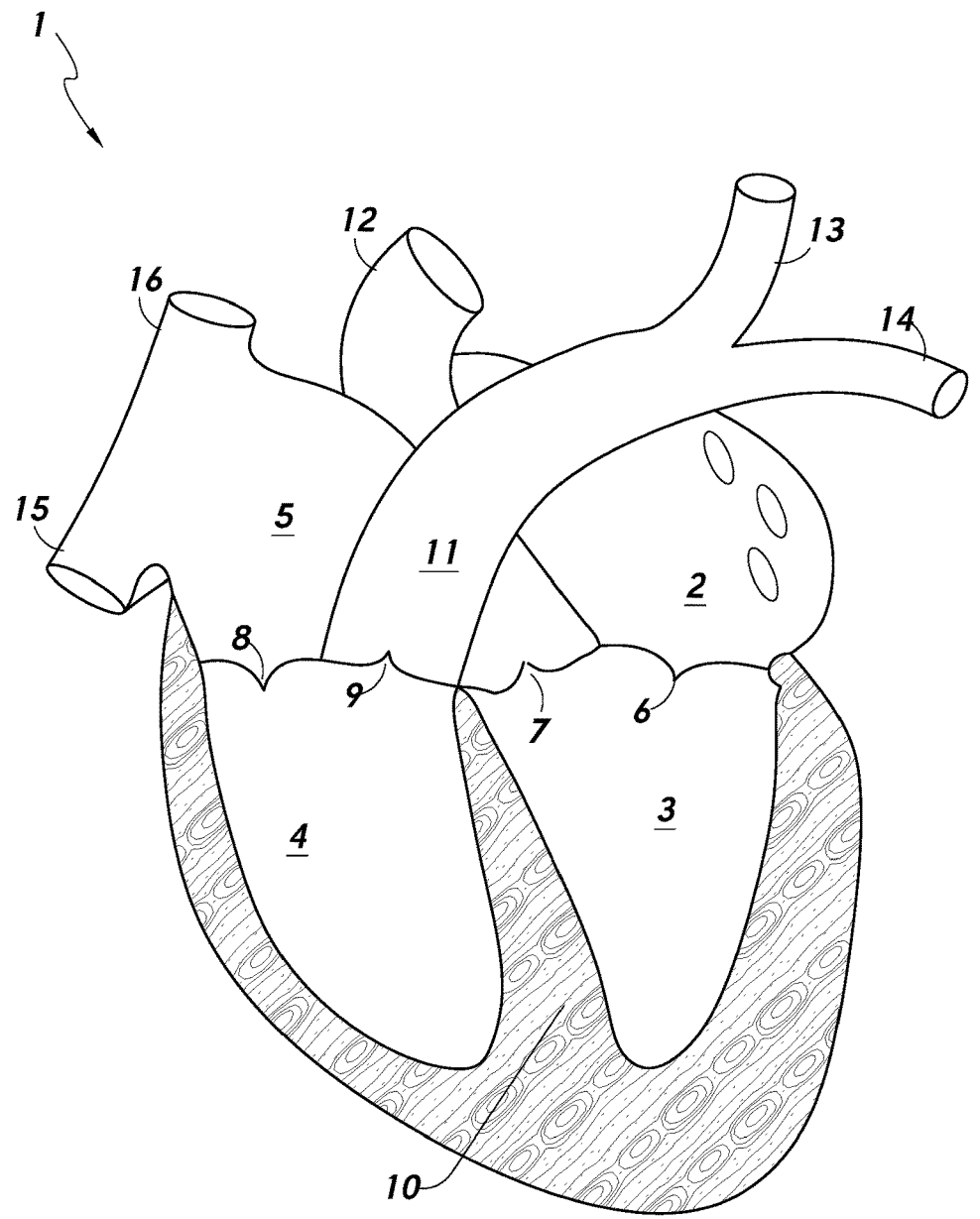
FIG. 1 is a cross-sectional view of a human heart.

The headings provided herein are for convenience only and do not necessarily affect the scope or meaning of the claimed invention.

The present disclosure relates to devices, systems and methods for providing minimally invasive transcatheter delivery of a puncture needle to a target tissue site on a vessel, channel, chamber and/or organ. A puncture needle as described herein can have a configuration which reduces or eliminates axial rotation of the puncture needle relative to a delivery catheter receiving the puncture needle, while the delivery catheter and puncture needle are advanced through a tortuous anatomical pathway to the target tissue site.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/ element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

In minimally invasive procedures, transcatheter delivery of a typical puncture needle into a vessel, channel, chamber and/or organ can be challenging due to difficulty in reliably controlling the axial orientation of the puncture needle. The puncture needle may undesirably rotate around its longitudinal axis when inserted through one or more bends in the anatomical pathway to reach a target site accessible from within the vessel, channel, chamber and/or organ. The puncture needle can be received within a delivery catheter. The typical puncture needle can rotate axially relative to the delivery catheter while the delivery catheter and/or the puncture needle is advanced to the target tissue site, thereby resulting in the puncture needle becoming misaligned relative to the delivery catheter. Misalignment of the puncture needle can prevent deployment of the puncture needle from the delivery catheter and/or can shift the exit trajectory of the puncture needle as it is extended from the delivery catheter, thereby impeding effective puncturing of the tissue at the target tissue site.

Transcatheter delivery of a puncture needle into the coronary sinus can be performed in procedures for forming an opening in the left atrial wall separating the coronary sinus from the left atrium. The opening in the left atrial wall can be formed for the delivery of medical device implants and/or therapies to the left atrial wall. For example, a shunt device can be delivered into the opening in the left atrial wall to provide a blood flow conduit from the left atrium into the coronary sinus for treating elevated left atrial pressure. Transcatheter delivery of a typical puncture needle into the coronary sinus can result in undesired axial rotation of the puncture needle within the delivery catheter lumen, thereby leading to significant offset in the orientation of the puncture needle. Incorrect orientation of the puncture needle within the lumen can interfere with or prevent desired opening formation on the left atrial wall, which can contribute to improper placement of the medical device implant and/or inadequate therapy delivery.

The present disclosure provides devices, systems and methods relating to minimally invasive transcatheter delivery of a puncture needle to a target tissue site. Described herein are puncture needles configured to maintain a desired axial orientation as the puncture needles are inserted through one or more bends in the anatomical pathways to the target sites. In some embodiments, a puncture needle system can comprise a puncture needle and a delivery catheter configured to receive the puncture needle. The delivery catheter can comprise a puncture needle lumen configured to receive the puncture needle, and a side outlet opening on a distal portion configured to allow extension therethrough of the puncture needle for piercing the tissue. The puncture needle can comprise one or more features configured to engage with a delivery catheter lumen wall to prevent or reduce axial rotation of a distal portion of the puncture needle relative to the delivery catheter. In some embodiments, the distal portion of the puncture needle can comprise an anchor portion and a curved puncture portion. The curved puncture portion can have a first end associated with a puncture tip configured to pierce tissue and a second end coupled to the anchor portion. The anchor portion can be configured to interact with the delivery catheter lumen wall to prevent or reduce axial rotation of the curved puncture portion. The anchor portion can comprise a portion which extends distally of the curved puncture portion. In some embodiments, the portion of the anchor portion extending distally of the curved puncture portion can engage with a portion of the delivery catheter lumen wall distal of the side outlet opening to prevent or reduce axial rotation of the curved puncture portion.

In some embodiments, the anchor portion can comprise a plurality of portions which meet at one or more bends such that the curved puncture portion and the anchor portion can comprise a zig-zag shape. In some embodiments, the plurality of portions of the anchor portion can each be linear or substantially linear. For example, the plurality of portions of the anchor portion can be linear or substantially linear in a relaxed state. The linear or substantially linear portions can be flexible such that the portions of the anchor portion can assume a curved configuration within the delivery catheter lumen when the delivery catheter bends while being advanced through a tortuous anatomical pathway. In some embodiments, the anchor portion can be one flexible portion configured to assume a curved shape when positioned at or proximate to the target tissue site. In some embodiments, the plurality of portions of the anchor portion can each be curved, for example comprising a pre-formed curvature. In some embodiments, the anchor portion can be one curved portion. For example, the anchor portion can be a pre-formed curved portion. The one or more pre-formed curved anchor portions can be flexible to facilitate advancement of the puncture needle through tortuous anatomical pathways and/or at or proximate to the target tissue site.

In some embodiments, one or more of the puncture needles described herein can comprise a curved puncture portion and/or anchor portion which has a lateral cross section which has a non-circular shape, such as to provide a reduced profile for the puncture needles. In some embodiments, the lateral cross section can have a rectangular or substantially rectangular shape. Alternatively, in some embodiments, the lateral cross section can have a rounded shape, including a circular or substantially circular shape. The lateral cross section can be taken along a plane perpendicular or substantially perpendicular to a longitudinal axis of the puncture needle.

In some embodiments, the puncture needles and/or puncture needle systems described herein can be configured for positioning into the coronary sinus to access a target site on the left atrial wall. A puncture needle as described herein can be used to form an opening on the left atrial wall such that a medical implant device, including a shunt device, such as an expandable shunt device, can be positioned on the left atrial wall. The shunt device can provide a blood flow pathway from the left atrium into the coronary sinus for relieving elevated left atrial pressure.

A puncture needle system can be advanced into the coronary sinus from the right atrium via the coronary sinus ostium. The right atrium can be accessed via the superior vena cava (SVC) or via the inferior vena cava (IVC). A transjugular or trans-subclavian approach can be used to access the right atrium via the superior vena cava. Alternatively, a transfemoral approach can be used to position the puncture needle system into the inferior vena cava, and from the inferior vena cava into the right atrium. To access the coronary sinus, the puncture needle system may traverse one or more bends in the anatomical pathway. The one or more bends can tend to axially rotate the puncture needle. For example, advancing the puncture needle system into the coronary sinus via the coronary sinus ostium from the right atrium can involve one or more bends which can result in exertion of torsional force upon the puncture needle, tending to rotate the puncture needle. The anchor portion can engage with one or more portions of the delivery catheter lumen wall to reduce or eliminate axial rotation of the curved puncture portion, effectively decoupling the axial orientation of the curved puncture portion from any axial rotations of portions of the puncture needle proximal of the curved puncture portion. The anchor portion can engage with the portion of the delivery catheter lumen wall distal of the side outlet opening such that the axial orientation of the curved puncture portion is unaffected or substantially unaffected by axial rotation of more proximal portions of the puncture needle.

In some embodiments, one or more of the puncture needles described herein can comprise an anchor portion and a curved puncture portion which are integrally formed. In some embodiments, the anchor portion and the curved puncture portion can be integrally formed using one single elongate portion. For example, the single elongate portion can be shaped from a single piece of material (e.g., a single piece of metallic material, a single piece of polymeric material). In some embodiments, a single piece of material can be split to provide the anchor portion and the curved puncture portion. For example, the curved puncture portion can be carved and/or cut from the piece of material to separate the curved puncture portion from a remaining portion of the piece of material, the remaining portion comprising the anchor portion. In some embodiments, forming the anchor portion and the curved puncture portion from a single piece of material can reduce or eliminate locations more susceptible to failure, such as locations at which two pieces of material are joined together. In some embodiments, the anchor portion and the curved puncture portion can be formed using a plurality of distinct pieces of material which are joined together (e.g., bonding, welding, gluing).

Although the puncture needles and/or puncture needle systems are primarily described herein as being used to access the heart, it will be understood that the use of the puncture needles and/or puncture needle systems are not so limited. The puncture needles and/or puncture needle systems can be used to access any number of vessels, channels, chambers and/or organs which involve advancing the puncture needles and/or puncture needle systems through anatomic pathways having one or more bends that can tend to axially rotate the puncture needles.

The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

Reference herein to "catheters" and/or "delivery catheters" can refer or apply generally to any type of elongate tubular delivery device comprising an inner lumen configured to slidably receive instrumentation, such as for positioning within an atrium or coronary sinus, including for example delivery sheaths and/or cannulas.

Various features of a heart 1 are described with reference to FIG. 1 to assist in understanding the present disclosure. The heart 1 includes four chambers, namely the left atrium 2, the left ventricle 3, the right ventricle 4, and the right atrium 5. A wall of muscle, referred to as the septum 10, separates the left atrium 2 and right atrium 5, and the left ventricle 3 and right ventricle 4. Blood flow through the heart 1 is at least partially controlled by four valves, the mitral valve 6, aortic valve 7, tricuspid valve 8, and pulmonary valve 9. The mitral valve 6 separates the left atrium 2 and the left ventricle 3 and controls blood flow therebetween. The aortic valve 7 separates and controls blood flow between the left ventricle 3 and the aorta 12. The tricuspid valve 8 separates the right atrium 5 and the right ventricle 4 and controls blood flow therebetween. The pulmonary valve 9 separates the right ventricle 4 and the pulmonary artery 11, controlling blood flow therebetween.

In a healthy heart, the heart valves can properly open and close in response to a pressure gradient present during various stages of the cardiac cycle (e.g., relaxation and contraction) to at least partially control the flow of blood to a respective region of the heart and/or to blood vessels. Deoxygenated blood arriving from the rest of the body generally flows into the right side of the heart for transport to the lungs, and oxygenated blood from the lungs generally flows into the left side of the heart for transport to the rest of the body. During ventricular diastole, deoxygenated blood arrive in the right atrium 5 from the inferior vena cava 15 and superior vena cava 16 to flow into the right ventricle 4, and oxygenated blood arrive in the left atrium 2 from the pulmonary veins to flow into the left ventricle 3. During ventricular systole, deoxygenated blood from the right ventricle 4 can flow into the pulmonary artery 11 for transport to the lungs (e.g., via the left 14 and right 13 pulmonary arteries), and oxygenated blood can flow from the left ventricle 3 to the aorta 12 for transport to the rest of the body.

A number of conditions can contribute to a higher than normal pressure in the left atrium. Dysfunction of the mitral valve can contribute to elevated left atrial pressure. Conditions such as mitral valve regurgitation and/or stenosis may result in difficulty in pumping blood from the left atrium to the left ventricle, contributing to elevated pressure in the left atrium. Valve stenosis can cause a valve to become narrowed or obstructed. Mitral valve stenosis can restrict blood flow from the left atrium to the left ventricle. Valve regurgitation occurs when a valve does not close properly. For example, regurgitation can occur due to improper coaptation of the valve leaflets. Mitral valve regurgitation can result in blood flow leakage back into the left atrium 2 from the left ventricle 3 when the left ventricle 3 contracts. Restricted flow of blood from the left atrium 2 into the left ventricle 3, and blood flow leakage from the left ventricle 3 back into the left atrium 2 can both contribute to elevated atrial pressure. Dysfunction in the left ventricle 3 can also contribute to elevated left atrial pressure. Elevated left atrial pressure may lead to left atrial enlargement, producing symptoms such as shortness of breath during exertion, fatigue, chest pain, fainting, abnormal heartbeat, and swelling of the legs and feet.

Figure 2:
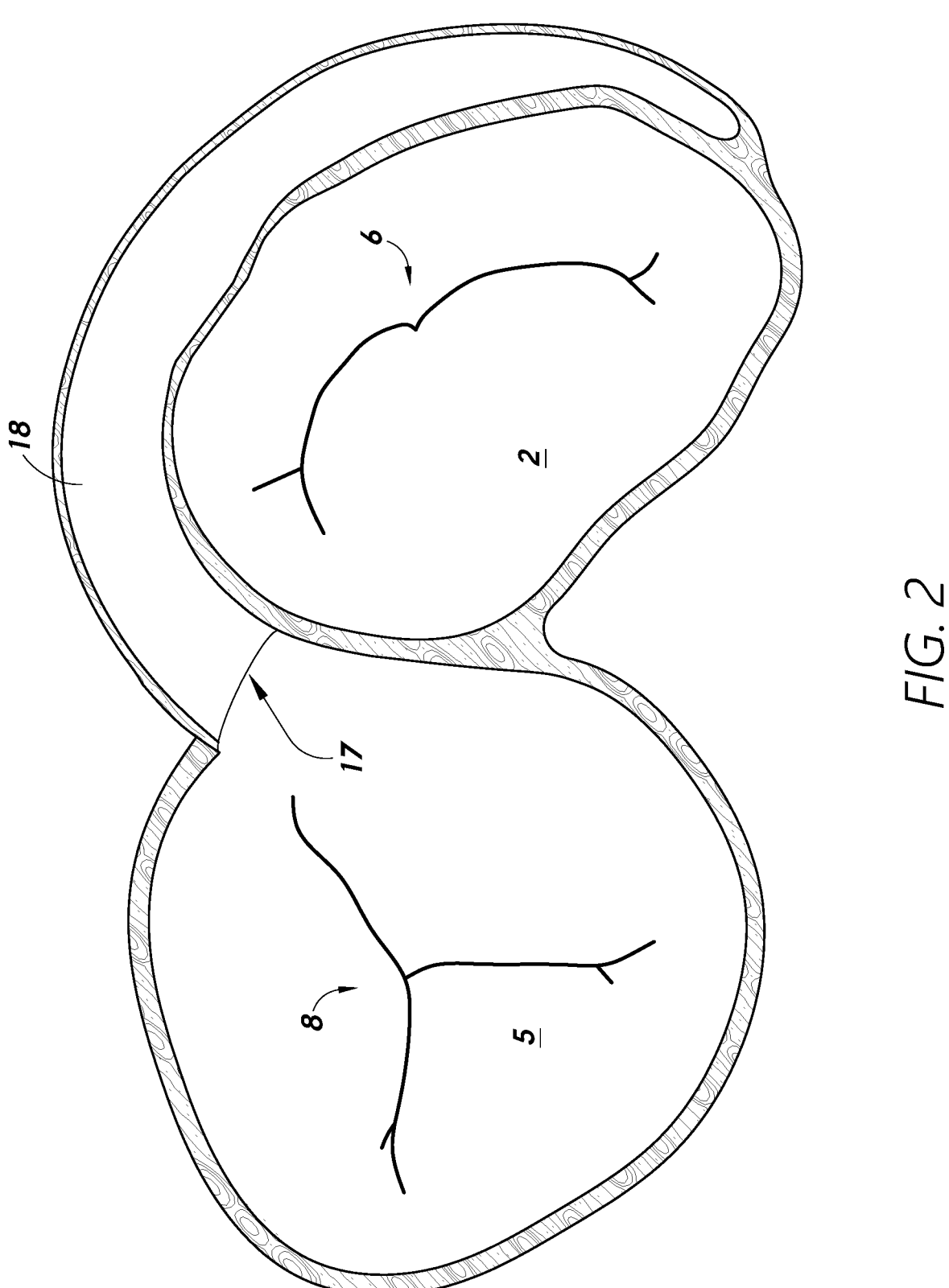
FIG. 2 is another cross-sectional view of the human heart.

FIG. 2 is another view of the heart 1 and shows the coronary sinus 18 around the left atrium 2. To alleviate elevated left atrial pressure, a conduit can be provided to allow blood flow from the left atrium 2 into a portion of the heart with lower pressure, such as the coronary sinus 18. A conduit can be formed on the wall of the left atrium 2 adjacent to the coronary sinus 18 to allow blood flow from the left atrium 2 into the coronary sinus 18. The coronary sinus 18 receives blood from coronary veins and empties into the right atrium 5. Blood diverted into the coronary sinus 18 from the left atrium 2 can then be delivered into the right atrium 5. A shunt device can be positioned at a location on the left atrial wall, such as a location which is accessible from the coronary sinus 18, to form a blood flow pathway from the left atrium 2 into the coronary sinus 18. Access into the coronary sinus 18 can comprise navigating into the right atrium 5 and entering through the coronary sinus ostium 17.

Figure 3:
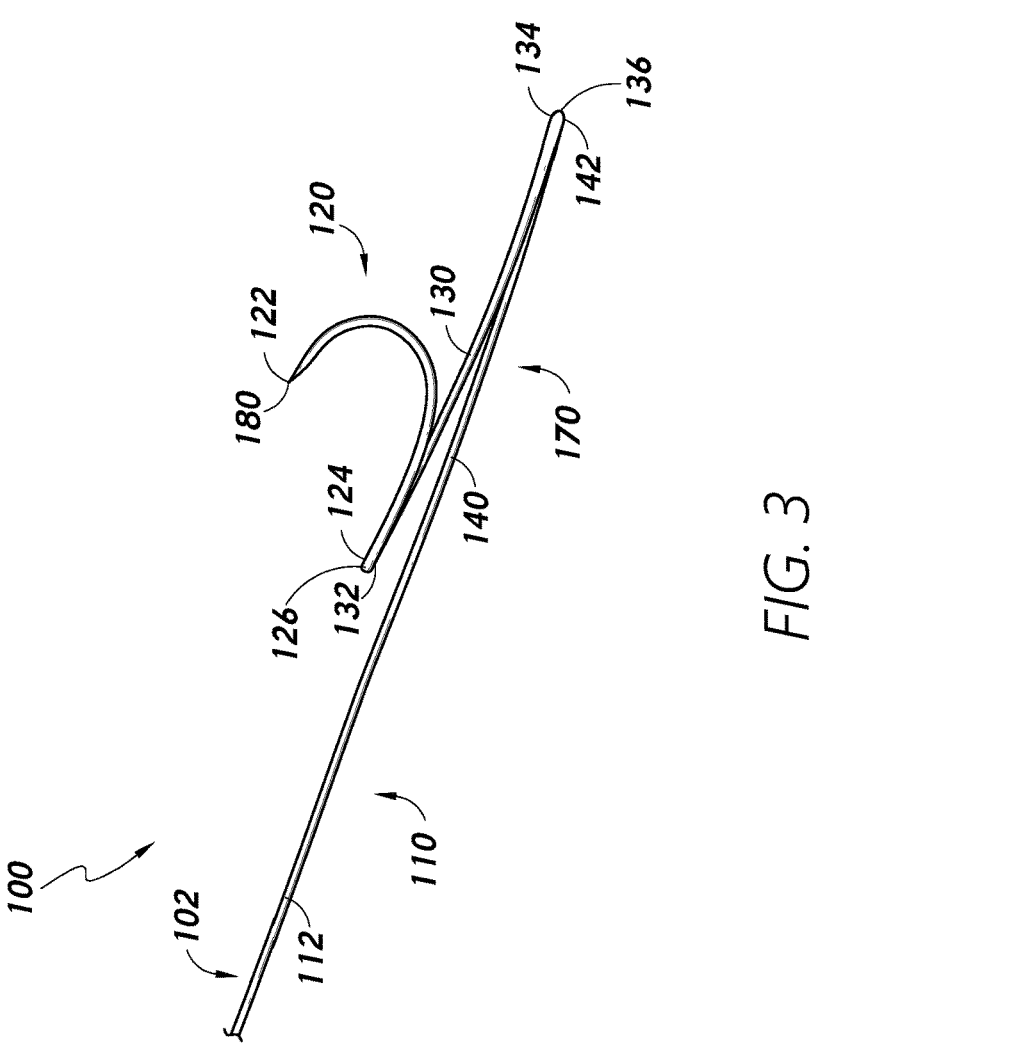
FIG. 3 shows an example of a puncture needle in accordance with one or more embodiments.

FIG. 3 is a perspective view of an example of a puncture needle 100. The puncture needle 100 can be received within a delivery catheter while the delivery catheter is advanced to a target tissue site. A distal portion 102 of the puncture needle 100 can comprise a curved puncture portion 120 and an anchor portion 170. For example, the puncture needle 100 can comprise an elongate portion 110 and a distal portion 112 of the elongate portion 110 can comprise the curved puncture portion 120 and the anchor portion 170. The puncture needle 100 can have a configuration which eliminates or reduces axial rotation of the curved puncture portion 120 within the delivery catheter as the delivery catheter is advanced through a tortuous anatomical pathway. The anchor portion 170 can be configured to engage with one or more portions of a lumen wall of the delivery catheter to reduce or eliminate rotation of the curved puncture portion 120 relative to the delivery catheter. The anchor portion 170 can comprise a portion which extends distally of the curved puncture portion 120. In some embodiments, the portion of the anchor portion 170 extending distally of the curved puncture portion 120 can engage with a corresponding portion of the wall of the delivery catheter lumen to facilitate maintaining a desired axial orientation for the curved puncture portion 120. In some embodiments, both the anchor portion 170 and the curved puncture portion 120 can be configured to engage with one or more portions of the delivery catheter lumen wall to reduce or eliminate rotation of the curved puncture portion 120. As described in further detail herein, while the puncture needle 100 is positioned within or substantially within the delivery catheter, such as while the puncture needle 100 is in a retracted state, the curved puncture portion 120 and the anchor portion 170 can engage with corresponding portions of the delivery catheter lumen wall to prevent or reduce axial rotation of the curved puncture portion 120.

The curved puncture portion 120 can comprise a first end 122 associated with a puncture tip 180. The puncture tip 180 can be configured to pierce tissue at the target tissue site. The curved puncture portion 120 can comprise a second end 124 coupled to the anchor portion 170. A radius of curvature of the curved puncture portion 120 can be selected to facilitate tissue puncture and/or formation of a desired opening at the target tissue site. The curvature can facilitate insertion of the puncture needle 100 into the tissue at the target tissue site as the curved puncture portion 120 is extended from the delivery catheter. The curved puncture portion 120 can comprise a pre-formed curvature configured to facilitate accessing the target tissue site while the puncture needle 100 is positioned in a vessel, channel, chamber and/or organ to facilitate effective puncture of the target tissue site. For example, in a relaxed state, the radius of curvature of the pre-formed curvature of the curved puncture portion 120 can facilitate accessing and/or puncturing a target tissue site on a left atrial wall while the curved puncture portion 120 is extended from a side outlet opening of a delivery catheter positioned in a coronary sinus. The curved puncture portion 120 can comprise a shape memory material such that the curved puncture portion 120 can assumed the curved configuration after it is released from the delivery catheter lumen. In some embodiments, the curved puncture portion 120 can comprise a segment of a circle. For example, the curved puncture portion 120 can comprise a semi-circle. Referring to FIG. 3, the curved puncture portion 120 can be oriented proximally. For example, an inner edge of the curved puncture portion 120 can comprise at least a portion which is oriented proximally, such that at least a portion of the concave portion of the curved puncture portion 120 is proximally oriented. In some embodiments, the puncture tip 180 can point proximally. In some embodiments, the puncture tip 180 can point laterally.

Referring to FIG. 3, the anchor portion 170 can comprise a first anchor portion 130 and a second anchor portion 140. The first anchor portion 130 can comprise a first end 132 and a second end 134. The first end 132 of the first anchor portion 130 can be coupled to the second end 124 of the curved puncture portion 120. For example, the first end 132 of the first anchor portion 130 can meet the second end 124 of the curved puncture portion 120 at a first bend 126. The first bend 126 can be oriented distally or substantially distally. In some embodiments, at least a portion of the concave portion of the first bend 126 is distally oriented. For example, the first bend 126 can comprise an acute angle, where the acute angle is oriented distally or substantially distally.

The first anchor portion 130 and the second anchor portion 140 can meet at a second bend 136. The second anchor portion 140 can comprise a first end 142 and the first end 142 of the second anchor portion 140 can be coupled to the second end 134 of the first anchor portion 130. The first end 142 of the second anchor portion 140 and the second end 134 of the first anchor portion 130 can meet at the second bend 136. The second bend 136 can be oriented proximally or substantially proximally. In some embodiments, at least a portion of the concave portion of the second bend 136 is proximally oriented. For example, the second bend 136 can comprise an acute angle, and the acute angle can be oriented proximally or substantially proximally. In some embodiments, the first bend 126 and the second bend 136 can comprise opposing or substantially opposing orientations. In some embodiments, the first bend 126 and the second bend 136 can each comprise an acute angle, and the acute angles can comprise opposing or substantially opposing orientations. The second anchor portion 140 can extend proximally from the first end 142.

In some embodiments, the first anchor portion 130 and the second anchor portion 140 can each comprise a linear or substantially linear portion. As described herein, the first bend 126 and the second bend 136 can each comprise an acute angle and have opposing or substantially opposing orientations. The curved puncture portion 120 and the anchor portion 170 together can comprise a zig-zag shape. In some embodiments, the first anchor portion 130 and the second anchor portion 140 can each be a linear or substantially linear portion, such that the curved puncture portion 120 and the anchor portion 170 together can comprise a "z" shape. In some embodiments, the first anchor portion 130 and the second anchor portion 140 can be flexible such that the first anchor portion 130 and the second anchor portion 140 can assume a curved configuration to conform to a curvature of a vessel, channel, chamber and/or organ into which the anchor portion 170 is positioned. In some embodiments, flexibility of the first anchor portion 130 and the second anchor portion 140 can facilitate advancement of the puncture needle 100 through tortuous anatomical pathways.

In some embodiments, the curved puncture portion 120 and the anchor portion 170 can be in the same plane and/or parallel planes. The curved puncture portion 120 and the anchor portion 170 can lay flat or substantially flat when laid on a side. For example, the curved puncture portion 120, the first anchor portion 130 and the second anchor portion 140 can all extend along lines contained in the same plane. In some embodiments, the curved puncture portion 120, the first anchor portion 130 and the second anchor portion 140, and the puncture tip 180 can all be in the same plane. In some embodiments, the curved puncture portion 120 and the anchor portion 170 can comprise corresponding portions in the same plane. For example, respective portions of the curved puncture portion 120, the first anchor portion 130 and the second anchor portion 140 can extend along lines contained in the same plane, such that the curved puncture portion 120, the first anchor portion 130 and the second anchor portion 140 each comprise portions which extend along lines contained in parallel planes.

In some embodiments, the curved puncture portion 120 can comprise a lateral cross section comprising a rounded shape, including a circular or substantially circular shape. Alternatively, the lateral cross section can comprise a non-circular shape, including a polygonal shape, such as a rectangular or substantially rectangular shape. The non-circular cross-sectional shape can provide a reduced profile for the puncture needle 100. The lateral cross section of the curved puncture portion 120 can be taken along a plane perpendicular or substantially perpendicular to a concavity of the curvature. In some embodiments, the anchor portion 170 can comprise a lateral cross section comprising a rounded shape, including a circular shape. Alternatively, the lateral cross section can comprise a non-circular shape, including a polygonal shape, such as a rectangular or substantially rectangular shape, for example to provide a reduced profile for the puncture needle 100. In some embodiments, a lateral cross section of a portion of the anchor portion 170 can be taken along a plane perpendicular or substantially perpendicular to a longitudinal axis of the puncture needle 100 and/or a longitudinal axis of the portion of the anchor portion 170.

In some embodiments, the curved puncture portion 120 and the anchor portion 170 can be integrally formed. In some embodiments, the curved puncture portion 120 and the anchor portion 170 can be a part of a single elongate portion. For example, a distal portion 112 of the elongate portion 110 can comprise the curved puncture portion 120, the first anchor portion 130 and the second anchor portion 140. The first anchor portion 130 can be a first distal elongate portion. The second anchor portion 140 can be a second distal elongate portion. As described herein, the curved puncture portion 120 can have the puncture tip 180 associated with the first end 122. The curved puncture portion 120 can extend from the first end 122 to the first bend 126. The first bend 126 can have a first acute angle oriented distally. The first distal elongate portion, or the first anchor portion 130, can meet the curved puncture portion 120 at the first bend 126. The first distal elongate portion can extend from the first bend 126 to the second bend 136. The second bend 136 can have a second acute angle oriented proximally. The first distal elongate portion can meet the second distal elongate portion, or the second anchor portion 140, at the second bend 136. The second distal elongate portion can extend proximally from the second bend 136. The second bend 136 can be distal of the curved puncture portion 120.

In some embodiments, the first bend 126 and the second bend 136 can each comprise a sharp and/or pointed bend. In some embodiments, the sharp and/or pointed bends can facilitate a reduced profile for the distal portion 102 of the puncture needle 100.

As described herein, the anchor portion 170 can comprise at least a portion which is distal of the curved puncture portion 120. A portion of the first anchor portion 130 and a portion of the second anchor portion 140 can be distal of the curved puncture portion 120. For example, the second bend 136 can be distal of the curved puncture portion 120. In some embodiments, the portion of the anchor portion 170 distal of the curved puncture portion 120 can engage with one or more portions of the delivery catheter lumen wall to facilitate maintaining a desired orientation of the curved puncture portion 120. The puncture needle 100 can be pre-loaded within the delivery catheter lumen, for example the curved puncture portion 120 and the anchor portion 170 being positioned proximate or adjacent to a side outlet opening configured to allow extension therethrough of the puncture needle 100.

As described in further detail herein, the anchor portion 170 can comprise a portion configured to be received in the portion of the delivery catheter lumen distal of the side outlet opening, both while the puncture needle 100 is in a retracted state and a deployed state. Having the anchor portion 170 engage and/or interact with the portion of the lumen wall distal of the side outlet opening, for example rather than with any portion of the lumen wall proximal of the side outlet opening, can facilitate stabilization of the axial orientation of the anchor portion 170, thereby facilitating stabilization of the axial orientation of the curved puncture portion 120. The desired axial orientation of the curved puncture portion 120 can be maintained or substantially maintained regardless of torsional forces exerted upon the puncture needle 100 and/or any rotations of the proximal portion of the puncture needle 100 while the delivery catheter is advanced through tortuous anatomical pathways. Engaging the anchor portion 170 with the portion of the delivery catheter lumen wall distal of the side outlet opening can decouple any axial rotation of the proximal portion of the puncture needle 100 from the curved puncture portion 120, allowing the curved puncture portion 120 to remain aligned relative to the delivery catheter. In some embodiments, the curved puncture portion 120 can exhibit no or reduced rotation around a longitudinal axis of the puncture needle 100 while the puncture needle 100 is positioned within the delivery catheter lumen and while the delivery catheter is advanced through a tortuous anatomical pathway to the target tissue site.

In some embodiments, both the curved puncture portion 120 and the anchor portion 170 can engage with corresponding portions of the delivery catheter lumen wall to prevent or reduce axial rotation of the curved puncture portion 120. For example, the bends 126, 136 in the distal portion 102 can render the curved puncture portion 120 and the anchor portion 170 to have a tendency to extend radially. For example, the curved puncture portion 120 and the anchor portion 170 can be spring-loaded. The tendency to extend radially can increase contact between the puncture needle 100 and the lumen wall of the delivery catheter. Increased contact between the puncture needle 100 and the lumen wall can facilitate fixation of the position and/or orientation of the curved puncture portion 120, reducing or preventing rotation of the curved puncture portion 120. In some embodiments, the tendency of the anchor portion 170 and curved puncture portion 120 to extend radially can facilitate extension of the curved puncture portion 120 through the side outlet opening when deploying the puncture needle 100.

Figure 4:
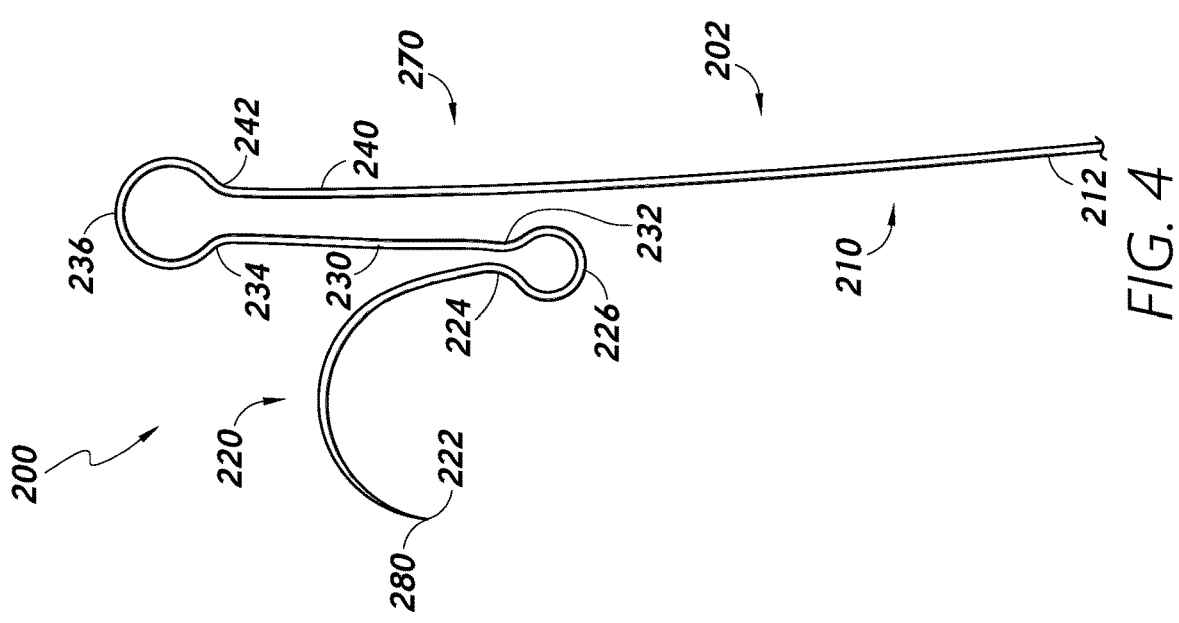
FIG. 4 shows an example of a puncture needle comprising a plurality of rounded bends on a distal portion of the puncture needle, in accordance with one or more embodiments.

FIG. 4 shows an example of a puncture needle 200. A distal portion 202 of the puncture needle 200 can comprise a plurality of bends each of which can have a rounded configuration. The distal portion 202 of the puncture needle 200 can comprise a curved puncture portion 220 and an anchor portion 270. The anchor portion 270 can comprise at least a portion which extends distally of the curved puncture portion 220. In some embodiments, the puncture needle 200 can comprise an elongate portion 210 and a distal portion 212 of the elongate portion 210 can comprise the curved puncture portion 220 and the anchor portion 270.

Referring to FIG. 4, the curved puncture portion 220 can comprise a first end 222 associated with a puncture tip 280 and a second end 224 coupled to the anchor portion 270. The curved puncture portion 220 can comprise one or more features of the curved puncture portion 120 described with reference to FIG. 3. For example, the curved puncture portion 220 can comprise a segment of a circle, such as a semi-circle. In some embodiments, the curved puncture portion 220 can be oriented proximally. In some embodiments, the puncture tip 280 can point proximally. In some embodiments, the puncture tip 280 can point laterally.

The anchor portion 270 can comprise a first anchor portion 230 comprising a first end 232 and a second end 234, and a second anchor portion 240 comprising a first end 242. The first end 232 of the first anchor portion 230 can be coupled to the second end 224 of the curved puncture portion 220. For example, the first end 232 of the first anchor portion 230 can meet the second end 224 of the curved puncture portion 220 at a first bend 226. As shown in FIG. 4, the first bend 226 can be oriented distally or substantially distally. For example, the concave portion of the first bend 226 can comprise at last a portion which is oriented distally or substantially distally. The first anchor portion 230 and the second anchor portion 240 can meet at a second bend 236. The first end 242 of the second anchor portion 240 can be coupled to the second end 234 of the first anchor portion 230. The first end 242 of the second anchor portion 240 and the second end 234 of the first anchor portion 230 can meet at the second bend 236. In some embodiments, the first bend 226 and the second bend 236 can comprise opposing or substantially opposing orientations. The second bend 236 can be oriented proximally or substantially proximally. For example, the concave portion of the second bend 236 can comprise at last a portion which is oriented proximally or substantially proximally. The second anchor portion 240 can extend proximally from the second bend 236.

In some embodiments, one or both of the first bend 226 and the second bend 236 can be rounded, for example comprising an arcuate shape. One or both of the first bend 226 and the second bend 236 can comprise a segment of a circle or an oval. In some embodiments, both the first bend 226 and the second bend 236 can be rounded, for example comprising a segment of a circle. In some embodiments, while in a relaxed state, such as when the puncture needle 200 is not within delivery catheter lumen, the first anchor portion 230 and the second anchor portion 240 can be parallel or substantially parallel to one another. In some embodiments, the second bend 236 can comprise a semi-circle. In some embodiments, the first bend 226 can comprise a semi-circle. In some embodiments, the first anchor portion 230 and the second anchor portion 240 are not parallel to one another. In some embodiments, the second bend 236 can comprise an acute angle. The acute angle can be oriented proximally or substantially proximally, for example a concave portion of the second bend 236 can be oriented proximally or substantially proximally.

The first bend 226 and the second bend 236 can each be sized such that opposing portions of each of the first bend 226 and the second bend 236 can contact opposing portions of the delivery catheter lumen wall. In some embodiments, contact between the bends 226, 236 and the delivery catheter lumen wall can reduce or prevent axial rotation of the distal portion 202 of the puncture needle 200, thereby maintaining the desired orientation of the curved puncture portion 220.

In some embodiments, engagement of the anchor portion 270 and the delivery catheter lumen wall can prevent or reduce axial rotation of the curved puncture portion 220. A portion of the anchor portion 270 distal of the curved puncture portion 220 can be received in the portion of the delivery catheter lumen distal of a side outlet opening of the delivery catheter both while the puncture needle 200 is in a retracted state and a deployed state. A portion of the first anchor portion 230 and a portion of the second anchor portion 240 can be distal of the curved puncture portion 220. For example, the second bend 236 can be distal of the curved puncture portion 220. In some embodiments, the portion of the anchor portion 270 distal of the curved puncture portion 220 can engage with one or more portions of the delivery catheter lumen wall distal of the side outlet opening to facilitate maintaining a desired orientation of the curved puncture portion 220. In some embodiments, both the curved puncture portion 220 and the anchor portion 270 can engage with corresponding portions of the delivery catheter lumen wall to prevent or reduce axial rotation of the curved puncture portion 220.

The puncture needle 200 can one or more other features of the puncture needle 100 described with reference to FIG. 3. For example, the first anchor portion 230 and the second anchor portion 240 can each comprise a linear or substantially linear portion. The first anchor portion 230 and the second anchor portion 240 can each be a linear or substantially linear portion. In some embodiments, the curved puncture portion 220 and the anchor portion 270 together can form a zig-zag shape, including for example a "z" shape. In some embodiments, the first anchor portion 230 and the second anchor portion 240 can be flexible such that anchor portions 230, 240 can assume a curved configuration to conform to a curvature of a vessel, channel, chamber and/or organ into which the anchor portion 270 is positioned. Flexibility of the first anchor portion 230 and the second anchor portion 240 can facilitate advancement of the puncture needle 200 through tortuous anatomical pathways.

In some embodiments, the curved puncture portion 220 and the anchor portion 270 can be in the same plane and/or parallel planes, for example extending along lines which are in the same plane and/or parallel planes. In some embodiments, the curved puncture portion 220, the first anchor portion 230, the second anchor portion 240, the first bend 226, the second bend 236, and the puncture tip 280 can all be in the same plane. The curved puncture portion 220 and the anchor portion 270 can lay flat or substantially flat when laid on a side. In some embodiments, the curved puncture portion 220 and the anchor portion 270 can comprise corresponding portions in the same plane. For example, respective portions of the puncture tip 280, the curved puncture portion 220, the first anchor portion 230, the first bend 226, the second anchor portion 240, and the second bend 236 can extend along lines contained in the same plane, such that the puncture tip 280, the curved puncture portion 220, the first anchor portion 230, the first bend 226, the second anchor portion 240, and the second bend 236 each comprise portions which extend along lines contained in parallel planes.

In some embodiments, the curved puncture portion 220 and the anchor portion 270 can be integrally formed. In some embodiments, the curved puncture portion 220 and the anchor portion 270 can be a part of a single elongate portion. For example, a distal portion 212 of the elongate portion 210 can comprise the curved puncture portion 220, the first bend 226, the first anchor portion 230, the second bend 236, and the second anchor portion 240. A lateral cross section of the curved puncture portion 220, the first bend 226, the first anchor portion 230, the second bend 236 and the second anchor portion 240 can comprise a lateral cross section comprising a rounded shape, including a circular shape. Alternatively, the lateral cross section can comprise a non-circular shape, including a polygonal shape, such as a rectangular shape. In some embodiments, a lateral cross section of the curved puncture portion 220, the first bend 226, and the second bend 236 can be taken along a plane perpendicular or substantially perpendicular to a concavity of the respective concavity. In some embodiments, a lateral cross section of the first anchor portion 230 and the second anchor portion 240 can be taken along a plane perpendicular or substantially perpendicular to a longitudinal axis of the respective portion of the anchor portion 270 and/or the puncture needle 200.

Figure 5:
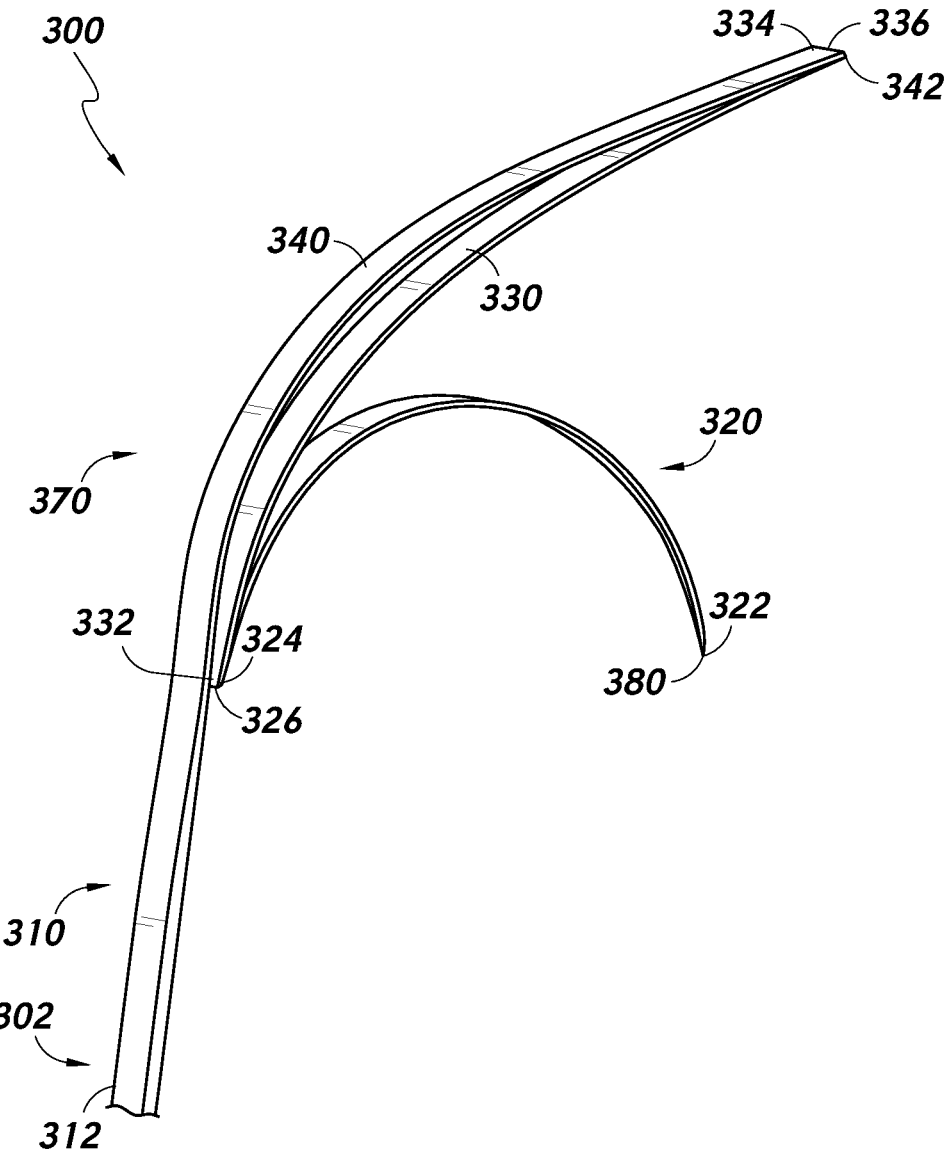
FIG. 5 shows an example of a puncture needle comprising an anchor portion which includes a first curved anchor portion and a second curved anchor portion, in accordance with one or more embodiments.

FIG. 5 shows an example of a puncture needle 300 comprising an anchor portion 370 which includes a first curved anchor portion 330 and a second curved anchor portion 340. The first curved anchor portion 330 and the second curved anchor portion 340 can each comprise a pre-formed curvature. A distal portion 302 of the puncture needle 300 can comprise a curved puncture portion 320 and the anchor portion 370. For example, an elongate portion 310 of the puncture needle 300 can comprise a distal portion 312 which can include the curved puncture portion 320 and the anchor portion 370.

The curved puncture portion 320 can comprise one or more features of the curved puncture portion 120 described with reference to FIG. 3. The curved puncture portion 320 can comprise a first end 322 associated with a puncture tip 380 and a second end 324 coupled to the anchor portion 370. The curved puncture portion 320 can comprise a segment of a circle, such as a semi-circle. In some embodiments, the curved puncture portion 320 can be oriented proximally. In some embodiments, the puncture tip 380 can point proximally. In some embodiments, the puncture tip 380 can point laterally.

The first curved anchor portion 330 and the second curved anchor portion 340 can comprise the same orientation. In some embodiments, the first curved anchor portion 330 and the second curved anchor portion 340 can comprise the same orientation as the curved puncture portion 320. For example, a corresponding concave portion of the first curved anchor portion 330 and the second curved anchor portion 340 can comprise at least a portion which is oriented proximally or substantially proximally. A radius of curvature of each of the first curved anchor portion 330 and the second curved anchor portion 340 can be selected based at least on a shape of the desired vessel, channel, chamber and/or organ into which the puncture needle 300 is advanced for accessing the target tissue site. For example, the radius of curvature of the first curved anchor portion 330 and the second curved anchor portion 340 can be selected based on a radius of curvature of the portion of the coronary sinus into which the anchor portion 370 is advanced. The anchor portion 370 can be shaped to follow a length of the curvature of the coronary sinus. In some embodiments, the radius of curvature for each of the first curved anchor portion 330 and the second curved anchor portion 340 can be greater than that of the curved puncture portion 320. For example, the degree of curvature of the curved puncture portion 320 can each be greater than that of the curved anchor portions 330, 340.

The curved puncture portion 320 can be coupled to the first curved anchor portion 330 at a first bend 326. A first end 332 of the first anchor portion 330 can meet the second end 324 of the curved puncture portion 320 at the first bend 326. The first bend 326 can be oriented distally or substantially distally. The first curved anchor portion 330 can be coupled to the second curved anchor portion 340 at a second bend 336. A first end 342 of the second anchor portion 340 can meet a second end 334 of the first anchor portion 330 at the second bend 336. In some embodiments, the first bend 326 and the second bend 336 can comprise opposing or substantially opposing orientations. The second bend 336 can be oriented proximally or substantially proximally. In some embodiments, the first bend 326 can comprise an acute angle, where the acute angle is oriented distally or substantially distally. In some embodiments, the second bend 336 can comprise an acute angle, and the acute angle can be oriented proximally or substantially proximally. The second anchor portion 340 can extend proximally from the second bend 336. In some embodiments, the first bend 326 and the second bend 336 can each comprise an acute angle such that the curved puncture portion 320 and the anchor portion 370 can comprise a zig-zag shape.

A portion of the anchor portion 370 can be distal of the curved puncture portion 320. For example, a portion of the first anchor portion 330 and a portion of the second anchor portion 340 can be distal of the curved puncture portion 320. The second bend 336 can be distal of the curved puncture portion 320. In some embodiments, the portion of the anchor portion 370 distal of the curved puncture portion 320 can engage with the delivery catheter lumen wall distal of a side outlet opening to prevent or reduce axial rotation of the curved puncture portion 320. In some embodiments, both the curved puncture portion 320 and the anchor portion 370 can engage with corresponding portions of the delivery catheter lumen wall to prevent or reduce axial rotation of the curved puncture portion 320.

In some embodiments, a lateral cross section of the curved puncture portion 320 and/or the anchor portion 370 can be non-circular. The lateral cross section can be taken along a plane perpendicular or substantially perpendicular to the concavity of the curved puncture portion 320 and/or respective portion of the anchor portion 370. The lateral cross section can be selected to reduce a profile of the puncture needle 300. In some embodiments, the lateral cross section can comprise a polygonal shape, such as a rectangular or substantially rectangular shape. In some embodiments, as described in further detail herein, the lateral cross section of the anchor portion 370 can be selected to correspond to a lateral cross section of the portion of the delivery catheter lumen distal of the side outlet opening to facilitate engagement of the anchor portion 370 with the lumen wall. Improved engagement between the anchor portion 370 and the lumen wall can facilitate maintaining the desired orientation of the curved puncture portion 320. The concavity of the curved puncture portion 320 and/or the anchor portion 370 can generally be normal to the long flat surface of the rectangular-cross-sectional form thereof, as in the diagram of FIG. 5. Alternatively, a lateral cross section of the curved puncture portion 320 and/or the anchor portion 370 can comprise a rounded shape, such as a circular shape.

In some embodiments, the curved puncture portion 320 and the anchor portion 370 can be in the same plane and/or parallel planes, for example extending along lines which are in the same plane and/or parallel planes. In some embodiments, the curved puncture portion 320, the first anchor portion 330, the second anchor portion 340 and the puncture tip 380 can all be in the same plane. The curved puncture portion 320 and the anchor portion 370 can lay flat or substantially flat when laid on a side. In some embodiments, the curved puncture portion 320 and the anchor portion 370 can comprise corresponding portions in the same plane. For example, respective portions of the curved puncture portion 320, the first anchor portion 330, the second anchor portion 340 and the puncture tip 380 can extend along lines contained in the same plane, such that the curved puncture portion 320, the first anchor portion 330, the second anchor portion 340 and the puncture tip 380 each comprise portions which extend along lines contained in parallel planes. In some embodiments, the curved puncture portion 320 and the anchor portion 370 can be integrally formed, for example being a part of a single elongate portion. For example, a distal portion 312 of the elongate portion 310 can comprise the curved puncture portion 320, the first anchor portion 330 and the second anchor portion 340. The first anchor portion 330 can be a first distal curved portion and the second anchor portion 340 can be a second distal curved portion.

Figure 6:
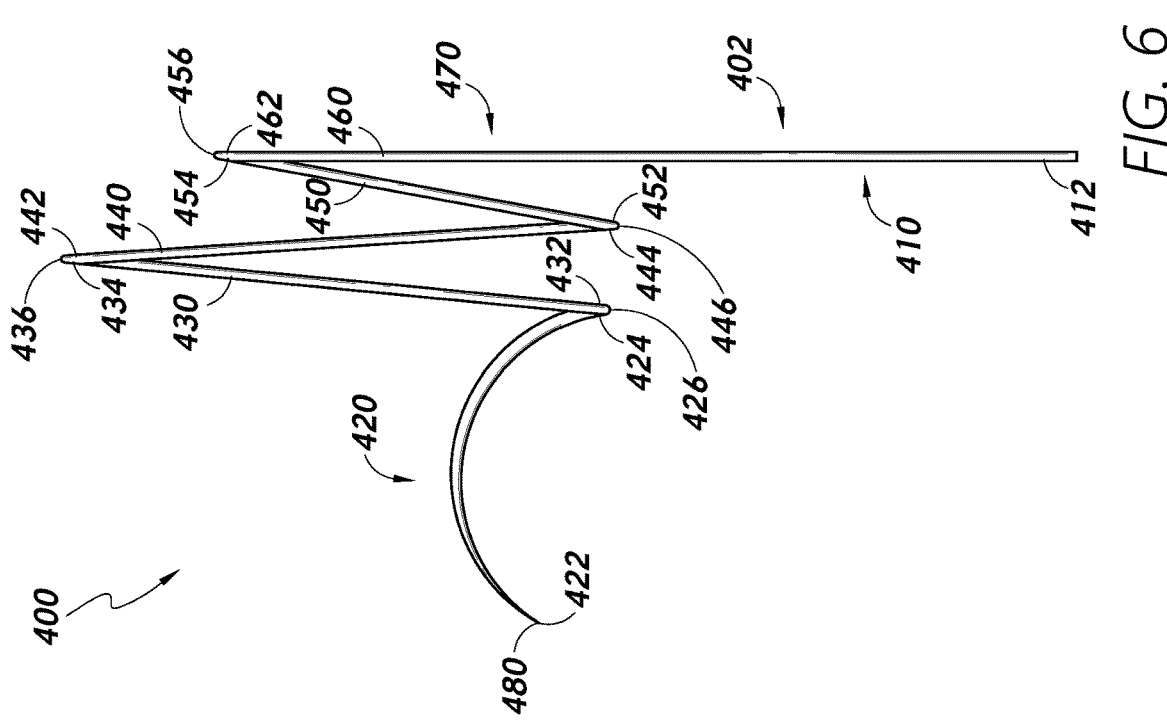
FIG. 6 shows an example of a puncture needle comprising an anchor portion which includes a first anchor portion, a second anchor portion, a third anchor portion and a fourth anchor portion, in accordance with one or more embodiments.

FIG. 6 shows an example of a puncture needle 400 comprising an anchor portion 470 which includes a first anchor portion 430, a second anchor portion 440, a third anchor portion 450 and a fourth anchor portion 460. A distal portion 402 of the puncture needle 400, such as a distal portion 412 of an elongate portion 410 of the puncture needle 400, can comprise the anchor portion 470. The anchor portion 470 can be coupled to a curved puncture portion 420. The curved puncture portion 420 can meet the first anchor portion 430 at a first bend 426. For example, a first end 432 of the first anchor portion 430 can be coupled to a second end 424 of the curved puncture portion 420 at the first bend 426. The first bend 426 can be oriented distally or substantially distally. The first anchor portion 430 can meet the second anchor portion 440 at a second bend 436. A second end 434 of the first anchor portion 430 can be coupled to a first end 442 of the second anchor portion 440 at the second bend 436. The second bend 436 can be oriented proximally or substantially proximally. The second anchor portion 440 can meet the third anchor portion 450 at a third bend 446. For example, a second end 444 of the second curved anchor portion 440 can be coupled to a first and 452 of the third curved anchor portion 450 at the third bend 446. The third bend 446 can be oriented distally or substantially distally. The third anchor portion 450 can meet the fourth anchor portion 460 at a fourth bend 456. A second and 454 of the third curved anchor portion 450 can be coupled to a first end 462 of the third curved anchor portion for 460 at the fourth bend 456. In some embodiments, the fourth bend 456 can be oriented proximally or substantially proximally. The fourth anchor portion 460 can extend proximally from the fourth bend 456.

In some embodiments, each of the first bend 426, the second bend 436, the third bend 446 and the fourth bend 456 can each comprise an acute angle. In some embodiments, adjacent bends can have opposing or substantially opposing orientations. For example, the first bend 426 can comprise an acute angle oriented distally or substantially distally. The second bend 436 can comprise an acute angle oriented proximally or substantially proximally. The third bend 446 can comprise an acute angle oriented distally or substantially distally. The fourth bend 456 can comprise an acute angle oriented proximally or substantially proximally. In some embodiments, each of the first anchor portion 430, the second anchor portion 440, the third anchor portion 450, and the fourth anchor portion for 460 can comprise a linear or substantially linear portion. For example, each of the first anchor portion 430, the second anchor portion 440, the third anchor portion 450, and the fourth anchor portion 460 can be linear or substantially linear such that the anchor portion 470 comprises a zig-zag shape. In some embodiments, the first anchor portion 430, the second anchor portion 440, the third anchor portion 450, and the fourth anchor portion 460 can be flexible such that anchor portions 430, 440, 450, 460 can assume a curved configuration to conform to a curvature of a vessel, channel, chamber and/or organ into which the anchor portion 470 is positioned. Alternatively, in some embodiments, each of the anchor portions 430, 440, 450, 460 can comprise a pre-formed curvature to conform to the curvature of the vessel, channel, chamber and/or organ. In some embodiments, the anchor portions 430, 440, 450, 460 can assume a curved configuration and/or have a pre-formed curvature to facilitate advancement of the puncture needle 400 through tortuous anatomical pathways.

A portion of the anchor portion 470 can be distal of the curved puncture portion 420. For example, at least a portion of each of the first anchor portion 430, the second anchor portion 440, the third anchor portion 450, and the fourth anchor portion 460, can be distal of the curved puncture portion 420. The second bend 436 and the fourth bend 456 can be distal of the curved puncture portion 420. The portion of the anchor portion 470 distal of the curved puncture portion 420 can engage with the delivery catheter lumen wall distal of a side outlet opening. In some embodiments, both the curved puncture portion 420 and the anchor portion 470 can engage with corresponding portions of the delivery catheter lumen wall to prevent or reduce axial rotation of the curved puncture portion 420.

FIG. 6 shows the second bend 436 distal of the fourth bend 456. In some embodiments, the second bend 436 can be proximal of the fourth bend 456. In some embodiments, having one of the second bend 436 or the fourth bend 456 distal of the other can facilitate improved engagement with the delivery catheter lumen wall distal of the side outlet opening, while maintaining a reduced distal profile for the puncture needle 400. In some embodiments, the second bend 436 and the third fourth 456 can be at a similar or same distal position.

The curved puncture portion 420 can comprise one or more features of the curved puncture portion 120 described with reference to FIG. 3. The curved puncture portion 420 can comprise a first end 422 associated with a puncture tip 480. The second end 424 can coupled to the anchor portion 470. In some embodiments, the curved puncture portion 420 can comprise a segment of a circle, for example comprising a semi-circle. The curved puncture portion 420 can be oriented proximally or substantially proximally. In some embodiments the puncture tip 480 can point proximally. In some embodiments the puncture tip 480 can point laterally. In some embodiments, the curved puncture portion 420 and the anchor portion 470 can be integrally formed, for example being a part of a single elongate portion.

Figure 7:
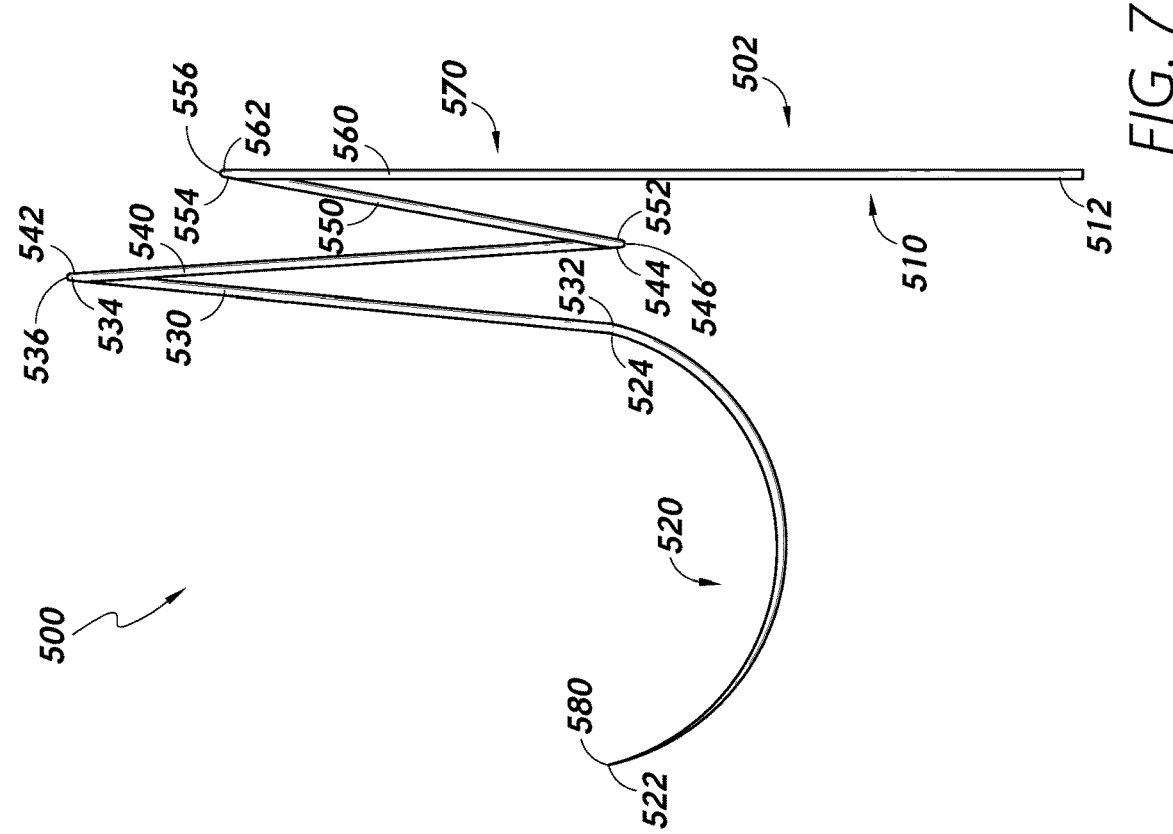
FIG. 7 shows an example of a puncture needle comprising an anchor portion which includes a first anchor portion, a second anchor portion, a third anchor portion and a fourth anchor portion, in accordance with one or more embodiments.

FIG. 7 shows an example of a puncture needle 500 comprising a distally or substantially distally oriented curved puncture portion 520. A distal portion 502 of the puncture needle 500 can comprise the curved puncture portion 520 and an anchor portion 570. The anchor portion 570 can be coupled to the curved puncture portion 520. For example, a distal portion 512 of an elongate portion 510 of the puncture needle 500 can comprise the anchor portion 570 and the curved puncture portion 520. The concave portion of the curved puncture portion 520 can comprise at least a portion which is oriented distally or substantially distally. In some embodiments the puncture tip 580 can point distally. In some embodiments the puncture tip 580 can point laterally. The curved puncture portion 520 can comprise one or more other features of the curved puncture portion 120 described with reference to FIG. 3. For example, the curved puncture portion 520 can comprise a first end 522 associated with a puncture tip 580, and a second end 524 coupled to the anchor portion 570. In some embodiments, the curved puncture portion 520 can comprise a segment of a circle, for example comprising a semi-circle.

The puncture needle 500 can comprise one or more other features of the puncture needle 400 described with reference to FIG. 6. In some embodiments, the puncture needle 500 can comprise the other features of the puncture needle 400. For example, the anchor portion 570 can comprise a first anchor portion 530, a second anchor portion 540, a third anchor portion 550 and a fourth anchor portion 560. A first end 532 of the first anchor portion 530 can be coupled to the second end 524 of the curved puncture portion 520. A second end 534 of the first anchor portion 530 can be coupled to a first end 542 of the second anchor portion 540 at a first bend 536. The first bend 536 can be oriented proximally or substantially proximally. A second end 544 of the second curved anchor portion 540 can be coupled to a first end 552 of the third curved anchor portion 550 at a second bend 546. The second bend 546 can be oriented distally or substantially distally. A second end 554 of the third curved anchor portion 550 can be coupled to a first end 562 of the third curved anchor portion for 560 at a third bend 556. The third bend 556 can be oriented proximally or substantially proximally. The fourth anchor portion 560 can extend proximally from the third bend 556.

In some embodiments, each of the first bend 536, the second bend 546 and the third bend 556 can comprise an acute angle. The first bend 536 can comprise an acute angle oriented proximally or substantially proximally. The second bend 546 can comprise an acute angle oriented distally or substantially distally. The third bend 556 can comprise an acute angle oriented proximally or substantially proximally. The first bend 536 can be distal, proximal, or at a same or similar distal position, as the third bend 556. In some embodiments, each of the first anchor portion 530, the second anchor portion 540, the third anchor portion 550, and the fourth anchor portion 560 can comprise a linear or substantially linear portion. For example, each of the first anchor portion 530, the second anchor portion 540, the third anchor portion 550, and the fourth anchor portion 560 can be linear or substantially linear such that the anchor portion 570 comprises a zig-zag shape. In some embodiments, the anchor portions 530, 540, 550, 560 can be flexible such that the anchor portions 530, 540, 550, 560 can assume a curved configuration to follow a curvature of a vessel, channel, chamber and/or organ into which the anchor portion 570 is positioned. Alternatively, in some embodiments, each of the anchor portions 530, 540, 550, 560 can comprise a pre-formed curvature to conform to the curvature of the vessel, channel, chamber and/or organ. In some embodiments, the anchor portions 530, 540, 550, 560 can assume a curved configuration and/or have a pre-formed curvature to facilitate advancement of the puncture needle 500 through tortuous anatomical pathways.

The puncture needles 400, 500 described with reference to FIGS. 6 and 7 can have one or more other features of the puncture needle 100 described with reference to FIG. 3. For example, the curved puncture portions 420, 520 and the anchor portions 470, 570 of the puncture needles 400, 500 described with reference to FIGS. 6 and 7 can be in the same plane and/or parallel planes, for example extending along lines which are in the same plane and/or parallel planes. In some embodiments, the curved puncture portion 520, the anchor portion 570, and the puncture tip 580 can all be in the same plane. The curved puncture portions 420, 520 and the anchor portions 470, 570 can comprise respective portions in the same plane. The respective portions of the curved puncture portions 420, 520 and the anchor portions 470, 570 can extend along lines contained in the same plane, such that the curved puncture portions 420, 520 and the anchor portions 470, 570 each comprise portions which extend along lines contained in parallel planes. In some embodiments, the curved puncture portion 520 and the anchor portion 570 can be integrally formed, for example being a part of a single elongate portion.

A lateral cross section of the puncture needles 400, 500 described with reference to FIGS. 6 and 7 can each comprise a rounded (e.g., a circular shape), or alternatively, non-circular, such as a polygonal shape. For example, each of the curved puncture portions 420, 520 and anchor portions 470, 570 can comprise a lateral cross section comprising a rounded shape, including a circular shape. Alternatively, the lateral cross section can comprise a rectangular shape. A lateral cross section of the curved puncture portions 420, 520 can be taken along a plane perpendicular or substantially perpendicular to a respective concavity of the curved puncture portions 420, 520. A lateral cross section of the anchor portions 470, 570 can be taken along a plane perpendicular or substantially perpendicular to a longitudinal axis of the respective puncture needles 400, 500 and/or the respective anchor portion.

Although the puncture needles 400, 500 described with reference to FIGS. 6 and 7 each comprise anchor portions 470, 570 which include four distinct portions, it will be understood that an anchor portion can comprise more distinct portions. For example, an anchor portion can comprise six distinct anchor portions. In some embodiments, an increased number of distinct anchor portions can further decouple the orientation of a curved puncture portion from any rotation of the proximal portion of the puncture needle. In some embodiments, the number of distinct anchor portions can be selected to provide a desired stabilization in the axial orientation of the curved puncture portion while providing a low profile puncture needle.

Figure 8A:
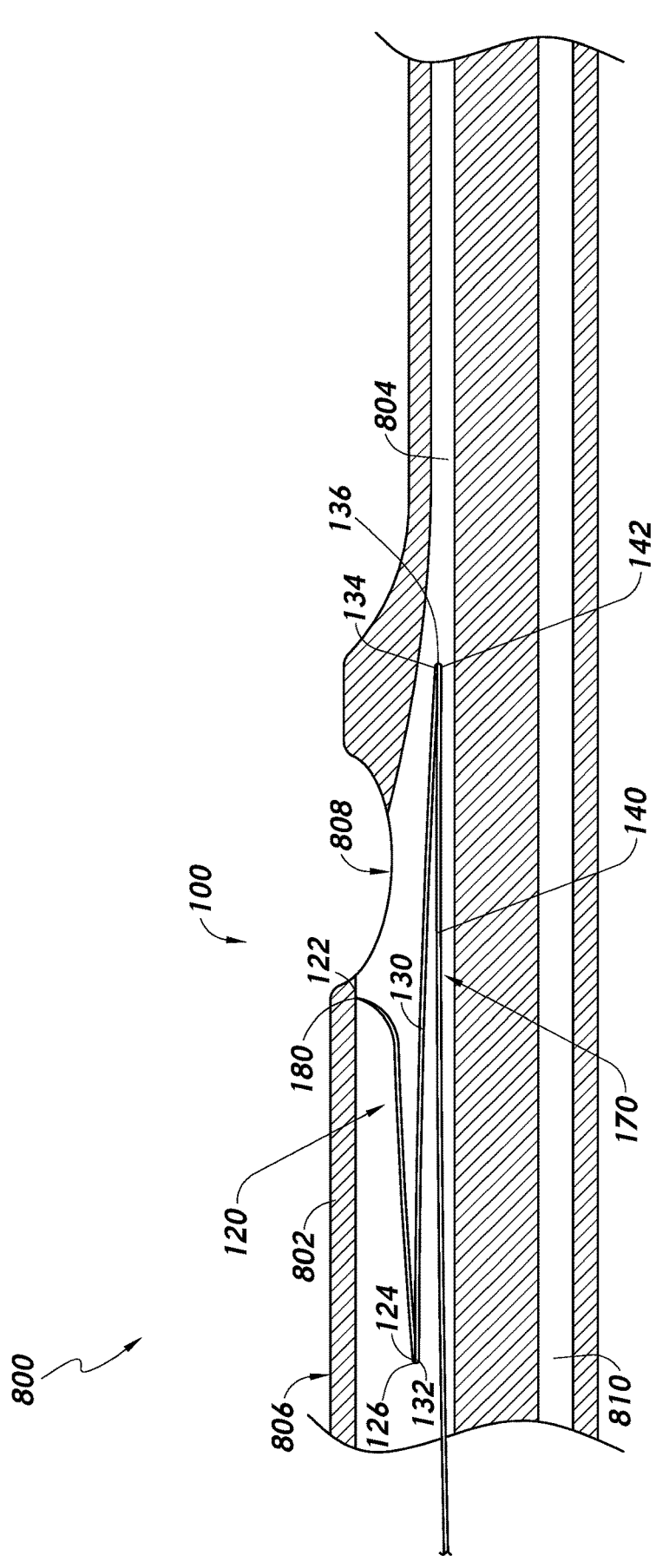
FIGS. 8A and 8B show a puncture needle system comprising the puncture needle of FIG. 3 in a retracted state and a deployed state, respectively, in accordance with one or more embodiments.
Figure 8B:
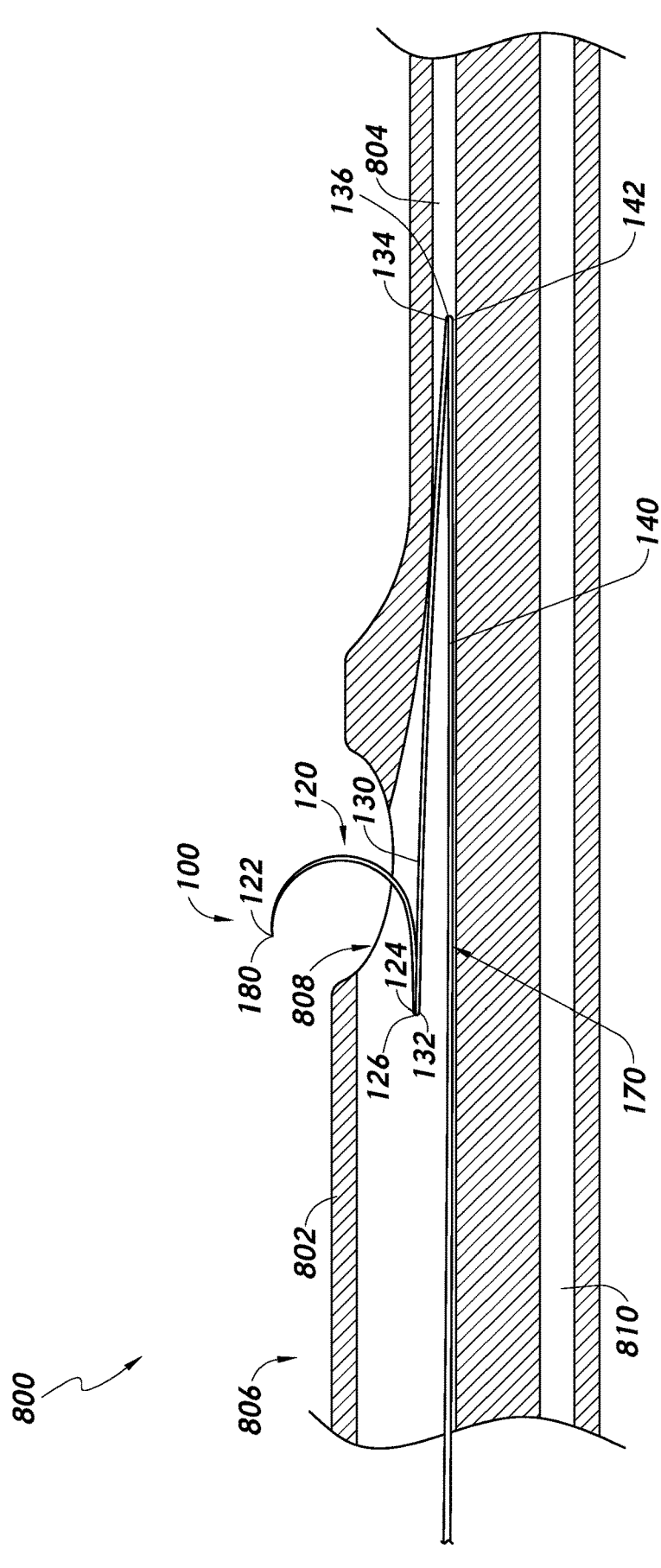

FIGS. 8A and 8B show a puncture needle system 800. The puncture needle system 800 can comprise the puncture needle 100 described with reference to FIG. 3, and a delivery catheter 802 configured to receive the puncture needle 100. Side cross-sectional views along a longitudinal axis of the delivery catheter 802 are shown in FIGS. 8A and 8B. The puncture needle 100 can be pre-loaded into the delivery catheter 802. For example, the puncture needle 100 can be positioned within the delivery catheter 802 prior to positioning the puncture needle system 800 at a target location to access the target tissue site, such as prior to inserting the puncture needle system 800 into the patient. FIG. 8A shows the puncture needle 100 pre-loaded in the delivery catheter 802 and in a retracted state. FIG. 8B shows the puncture needle 100 in a deployed state. Referring to FIG. 8A, the delivery catheter 802 can comprise a puncture needle lumen 804 configured to receive the puncture needle 100. A distal portion 806 of the delivery catheter 802 can comprise a side outlet opening 808 configured to allow extension therethrough of the puncture needle 100 to access the target tissue site. In some embodiments, the delivery catheter 802 can comprise a guide wire lumen 810 configured to receive a guide wire (not shown). The delivery catheter 802 can be advanced along the guide wire so as to position the delivery catheter 802 at a desired location to access the target tissue site.

Insertion of a puncture needle through one or more bends of tortuous anatomical pathways can result in undesired axial rotation of the puncture needle. Undesired rotation of a puncture needle positioned within a delivery catheter can cause misalignment of the puncture needle relative to the side outlet opening, thereby impeding desired deployment of the puncture needle from the delivery catheter, and/or use of the puncture needle to pierce tissue at the target tissue site. In some embodiments, misalignment of the puncture needle can hinder effective puncture of the tissue.

The anchor portion 170 can comprise a portion positioned within a portion of the puncture needle lumen 804 distal of the side outlet opening 808. In the retracted state, the second bend 136 of the puncture needle 100 can be distal of the side outlet opening 808. For example, a portion of the first anchor portion 130 and a portion of the second anchor portion 140 can be received within the portion of the puncture needle lumen 804 distal of the side outlet opening 808. In some embodiments, positioning a portion of the anchor portion
170 distal of the side outlet opening 808 can facilitate
maintaining the desired axial orientation of the curved
puncture portion 120 within the puncture needle lumen 804.
The anchor portion 170 can engage with the wall of the
portion of the puncture needle lumen 804 distal of the side
outlet opening 808 to reduce or eliminate undesired rotation
of the curved puncture portion 120 around a longitudinal
axis of the puncture needle 100.

In the retracted state, the first bend 126 of the puncture
needle 100 can be proximal of the side outlet opening 808.
FIG. 8A shows the puncture tip 180 proximal of the side
outlet opening 808. In some embodiments, the entirety or
substantially entirety of the curved puncture portion 120 can
be proximal of the side outlet opening 808. For example, the
puncture tip 180 and the curved puncture portion 120 can be
proximal of the side outlet opening 808 and can be received
within the puncture needle lumen 804. The first bend 126
can be proximal of the side outlet opening 808. The anchor
portion 170 can extend along the puncture needle lumen 804
past the side outlet opening 808. For example, the anchor
portion 170 can extend along a portion of the puncture
needle lumen 804 proximal of the side outlet opening 808,
through a portion of the lumen 804 at the side outlet opening
808, and along a portion of the puncture needle lumen 804
distal of the side outlet opening 808.

In some embodiments, portions of the curved puncture
portion 120 and/or the anchor portion 170 can engage with
a portion of the wall of the puncture needle lumen 804
proximal of the side outlet opening 808. The distal portion
102 of the puncture needle 100 comprising the bends 126,
136 can tend to exert radial force upon the curved puncture
portion 120 and the anchor portion 170 so as to provide a
spring-loaded effect. The tendency to extend radially can
increase contact between the puncture needle 100 and the
lumen wall of the delivery catheter 802, thereby facilitating
fixation of the position and/or orientation of the curved
puncture portion 120. In some embodiments, the tendency of
the anchor portion 170 and curved puncture portion 120 to
extend radially can facilitate extension of the curved punc-
ture portion 120 through the side outlet opening 808 when
deploying the puncture needle 100. For example, when the
curved puncture portion 120 is aligned with the side outlet
opening 808, the tendency to extend radially can facilitate
extension of the curved puncture portion 120 beyond the
opening 808 to assume its desired curved shape.

Referring to FIG. 8B, while the puncture needle 100 is in
the deployed state, at least a portion of the curved puncture
portion 120 can be extended through the side outlet opening
808. In some embodiments, as shown in FIG. 8B, only a
portion of the curved puncture portion 120 can be extended
through the side outlet opening 808 in the deployed state.
For example, the first bend 126 can be within the puncture
needle lumen 804 proximal of the side outlet opening 808.
In some embodiments, the entire or substantially the entire
curved puncture portion 120 can be extended beyond the
side outlet opening 808. For example, the first bend 126 can
be released from the puncture needle lumen 804. In some
embodiments, the first bend 126 can be extended beyond the
side outlet opening 808 in the deployed state. In some
embodiments, the first bend 126 can be aligned with the side
outlet opening 808.

The puncture needle 100 can be distally translated relative
to the delivery catheter 802 to release at least a portion of the
curved puncture portion 120 through the side outlet opening
808. The puncture needle 100 can be pushed to align the
curved puncture portion 120 with the side outlet opening 808 such that the puncture tip 180 and at least a portion of
the curved puncture portion 120 can be extended through the
side outlet opening 808. The curved puncture portion 120
can comprise a shape memory material such that once the
curved puncture portion 120 is freed from the constraints of
the delivery catheter 802, the curved puncture portion 120
can assume its desired curved configuration.

After the opening at the target tissue location is formed,
the puncture needle 100 can be translated proximally to
retract the curved puncture portion 120 back into the punc-
ture needle lumen 804 through the side outlet opening 808.
For example, the puncture needle 100 can be pulled relative
to the delivery catheter 802 to retract the curved puncture
portion 120 back into the lumen 804.

Alternatively, in some embodiments, while the puncture
needle 100 is in the retracted state, at least a portion of the
curved puncture portion 120 can be positioned within the
portion of the puncture needle lumen 804 distal of the side
outlet opening 808. In some embodiments, in the retracted
state, the curved puncture portion 120 can be entirely or
substantially entirely distal of the side outlet opening 808.
The puncture needle 100 can be translated proximally rela-
tive to the delivery catheter 802 to release at least a portion
of the curved puncture portion 120 through the side outlet
opening 808. The puncture needle 100 can be pulled to align
the curved puncture portion 120 with the side outlet opening
808 to extend the puncture tip 180 and at least a portion of
the curved puncture portion 120 through the side outlet
opening 808.

Figure 9:
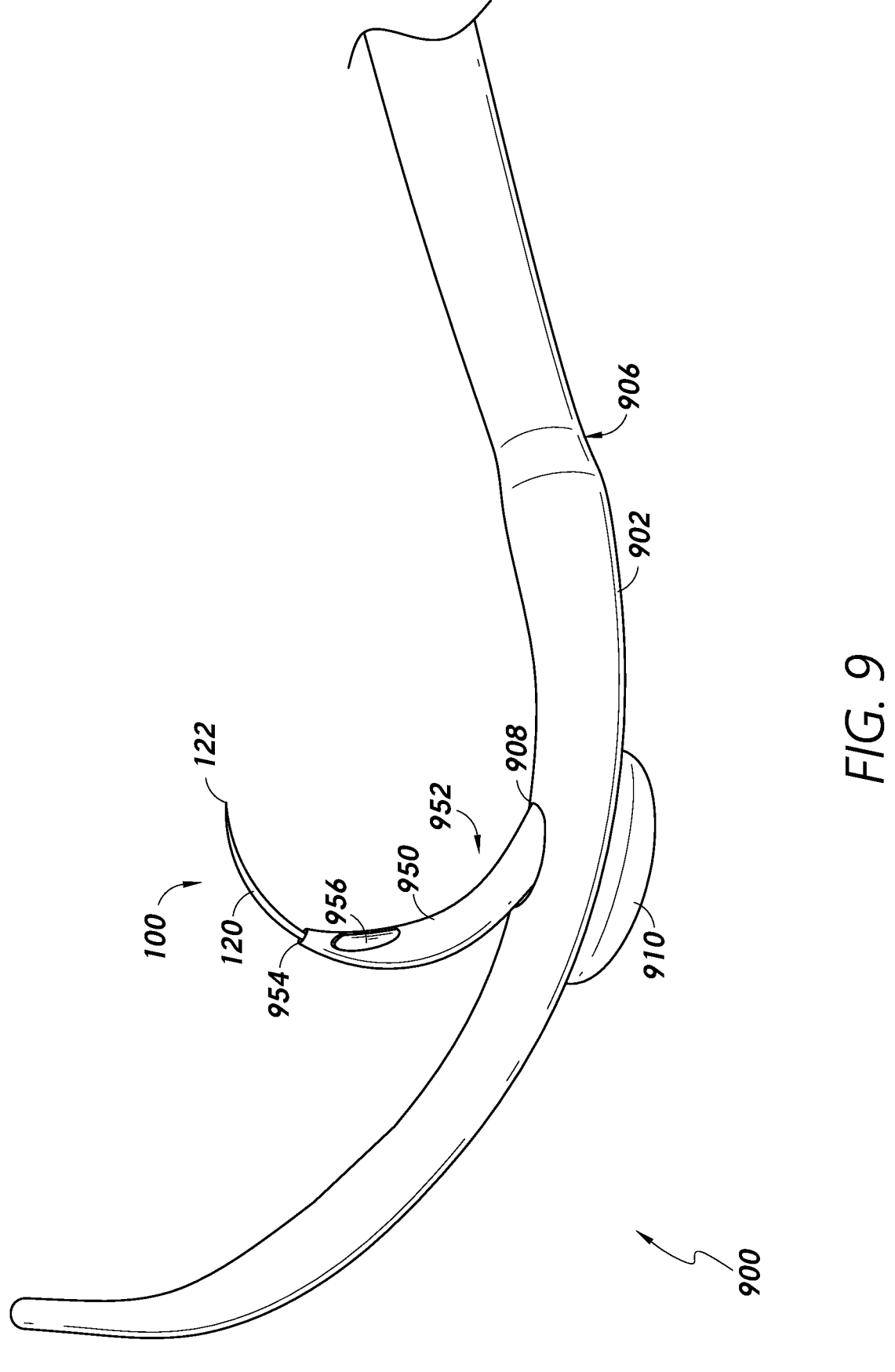
FIG. 9 shows a puncture needle system comprising a medical implant guide wire sheath, in accordance with one or more embodiments.

FIG. 9 shows a puncture needle system 900 comprising a
delivery catheter 902 and the puncture needle 100 received
within the delivery catheter 902. The delivery catheter 902
can comprise a puncture needle lumen configured to receive
the puncture needle 100. A distal portion 906 of the delivery
catheter 902 can comprise a side outlet opening 908 con-
figured to allow extension therethrough of the puncture
needle 100. The distal portion 906 can comprise a curved
portion, such as to facilitate positioning of the distal portion
906 into a target vessel, channel, chamber and/or organ. In
some embodiments, an expandable anchor 910 can be asso-
ciated with the distal portion 906 of the delivery catheter
902. The expandable anchor 910 can assume an expanded
state to facilitate stably positioning the distal portion 906 at
a desired location within the target vessel, channel, chamber
and/or organ. For example, the 910 can be associated with
the curved portion of the distal portion 906. In some
embodiments, the delivery catheter 902 can comprise a
guide wire lumen extending therethrough and configured to
receive a delivery catheter guide wire. The delivery catheter
902 can be advanced along the delivery catheter guide wire
so as to position the delivery catheter 902 at a desired
location to access the target tissue site.

The puncture needle system 900 can comprise a medical
implant guide wire sheath 950 configured to receive a
medical implant guide wire (not shown). The medical
implant guide wire sheath 950 can comprise a distal portion
952 configured to be coupled to the curved puncture portion
120 of the puncture needle 100. In some embodiments, the
distal portion 952 can be fixedly coupled to the curved
puncture portion 120 such that the distal portion 952 can be
translated proximally and/or distally along with the curved
puncture portion 120. The distal portion 952 of the medical
implant guide wire sheath 950 can be extended and/or
retracted through the side outlet opening 908 along with the
curved puncture portion 120 of the puncture needle 100. In
some embodiments, the medical implant guide wire sheath
950 can be coupled to a portion of the curved puncture portion 120. In some embodiments, the medical implant guide wire sheath 950 can be coupled to the entirety or substantially the entirety of the curved puncture portion 120. The medical implant guide wire sheath 950 can extend proximally from the curved puncture portion 120, for example being received in the puncture needle lumen of the delivery catheter 902.

The medical implant guide wire sheath 950 can comprise a distal end 954 coupled to the curved puncture portion 120. The distal end 954 can be proximal of the first end 122 of the curved puncture portion 120. For example, the distal end 954 can be proximal of the puncture tip 180. In some embodiments, the distal end 954 can be at the first end 122, for example adjacent to the puncture tip 180. The medical implant guide wire sheath 950 can comprise a distal outlet opening 956 through which the medical implant guide wire can be extended. The distal outlet opening 956 can be at or proximate to the distal end 954.

After the opening is formed at the target tissue site, the medical implant guide wire can be advanced through the medical implant guide wire sheath 950. A distal portion of the medical implant guide wire can be extended through the distal outlet opening 956, and into the opening formed at the target tissue site. The puncture needle system 900, including the medical implant guide wire sheath 950, can be retracted after the medical implant guide wire is positioned through the opening formed at the target tissue site, leaving the medical implant guide wire in place. A medical implant device can subsequently be advanced along the medical implant guide wire to the target tissue site. For example, a shunt device can be advanced along the medical implant guide wire to an opening formed on the left atrial wall to shunt blood flow from the left atrium into the coronary sinus.

Figures 10, 11:
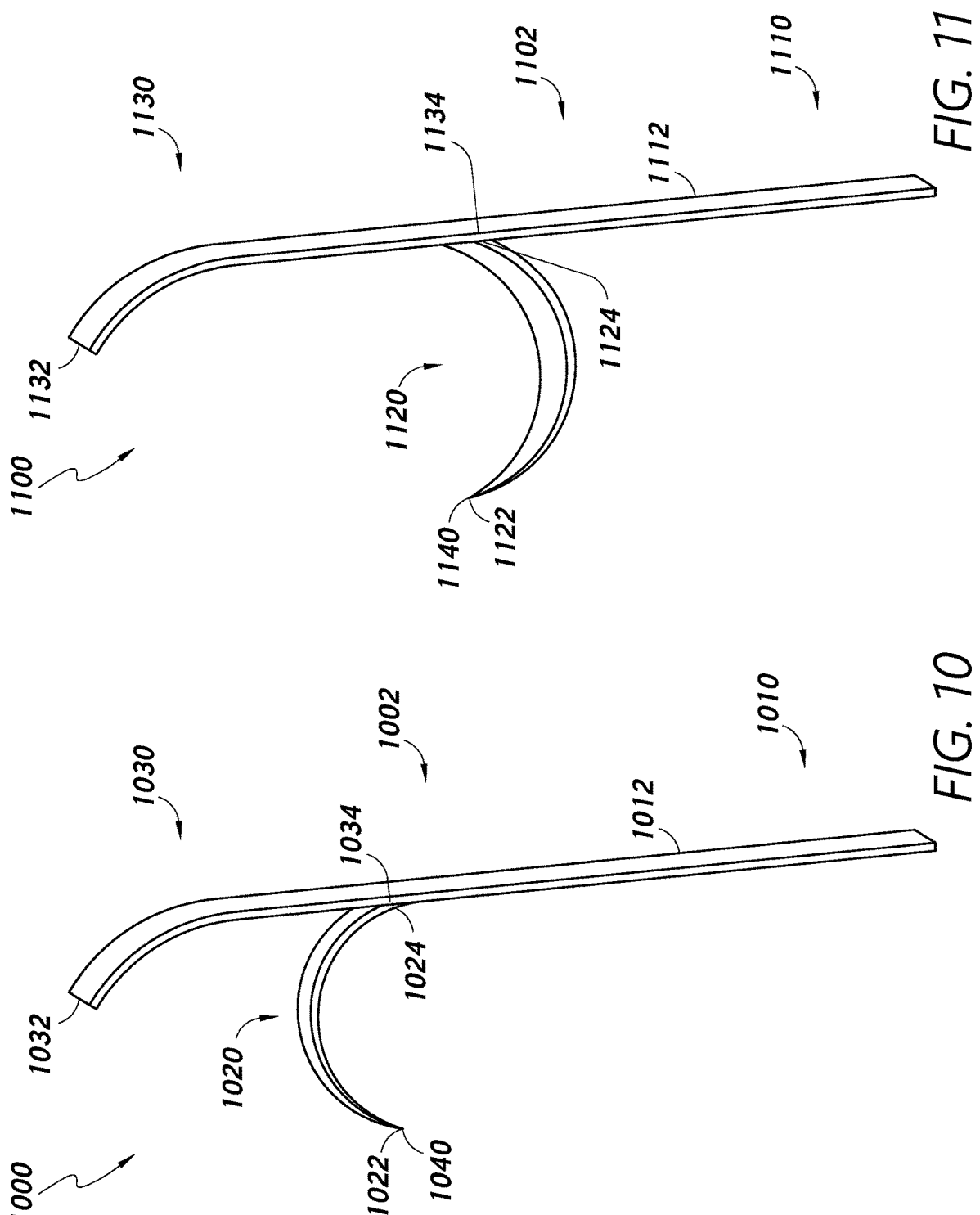
FIG. 10 shows an example of a puncture needle comprising a curved anchor portion and a proximally oriented curved puncture portion, in accordance with one or more embodiments.
FIG. 11 shows an example of a puncture needle comprising a curved anchor portion and a distally oriented curved puncture portion, in accordance with one or more embodiments.

FIG. 10 shows an example of a puncture needle 1000 comprising a curved anchor portion 1030 and a proximally or substantially proximally oriented curved puncture portion 1020. A distal portion 1002 of the puncture needle 1000 can comprise the curved puncture portion 1020 and the curved anchor portion 1030. For example, the curved anchor portion 1030 can comprise a pre-formed curvature. The puncture needle 1000 can comprise an elongate portion 1010 and a distal portion 1012 of the elongate portion 1010 can comprise the curved puncture portion 1020 and the curved anchor portion 1030. The curved anchor portion 1030 can comprise a portion extending distally of the curved puncture portion 1020. For example, a distal end 1032 of the curved anchor portion 1030 can be distal of the curved puncture portion 1020. The curved anchor portion 1030 can comprise a second end 1034 coupled to the curved puncture portion 1020. The curved puncture portion 1020 can comprise a first end 1022 associated with a puncture tip 1040 and a second end 1024 coupled to the second end 1034 of the curved anchor portion 1030. The curved puncture portion 1020 can comprise one or more features of the curved puncture portion 120 described with reference to FIG. 3. For example, the curved puncture portion 1020 can comprise a segment of a circle, such as a semi-circle. In some embodiments, the curved puncture portion 1020 can be oriented proximally. In some embodiments, the puncture tip 1040 can point proximally. In some embodiments, the puncture tip 1040 can point laterally.

The puncture needle 1000 can be received within a delivery catheter. A distal portion of the delivery catheter can comprise a side outlet opening through which the puncture needle 1000 can extend, such as the curved puncture portion 1020. The portion of the curved anchor portion 1030 extending distally of the curved puncture portion 1020 can be configured to engage with a portion of the delivery catheter lumen distal of the side outlet opening to reduce or eliminate axial rotation of the curved puncture portion 1020.

A curvature of the curved puncture portion 1020 and a curvature of the curved anchor portion 1030 can have the same orientation. As shown in FIG. 10, both the curved puncture portion 1020 and the curved anchor portion 1030 can be proximally oriented. For example, an inner edge of the curvature of the curved anchor portion 1030 can comprise at least a portion which is proximally oriented.

In some embodiments, in a relaxed state, the curved puncture portion 1020 can have a radius of curvature smaller than that the curved anchor portion 1030. For example, the degree of curvature of the curved puncture portion 1020 can be greater than that of the curved anchor portion 1030. The radius of curvature of the curved anchor portion 1030 can be selected based on a curvature of the anatomical pathway adjacent to or proximate to the target tissue site. For example, as described herein, the puncture needle 1000 can be configured to be inserted into the coronary sinus to pierced tissue on a portion of the left atrial wall accessible from within the coronary sinus. The radius of curvature of the curved anchor portion 1030 can be selected based on the radius of curvature of the coronary sinus into which the curved anchor portion 1030 is advanced. For example, the curved anchor portion 1030 can be shaped to follow a length of the curvature of the coronary sinus.

In some embodiments, the curved puncture portion 1020 and the curved anchor portion 1030 can be in the same plane and/or parallel planes. For example, the curved puncture portion 1020 and the curved anchor portion 1030 can extend along lines which are in the same plane and/or parallel planes. The curved puncture portion 1020 and the curved anchor portion 1030 can comprise respective portions in the same plane. The respective portions of the curved puncture portion 1020 and the curved anchor portion 1030 can extend along lines contained in the same plane, such that the curved puncture portion 1020 and the curved anchor portion 1030 each comprise portions which extend along lines contained in parallel planes.

A lateral cross section of the curved puncture portion 1020 and the curved anchor portion 1030 can comprise a non-circular shape, such as a polygonal shape, including a rectangular shape. Alternatively, the lateral cross section can comprise a rounded shape, including a circular shape. A lateral cross section of the curved puncture portion 1020 and the curved anchor portion 1030 can be taken along a plane perpendicular or substantially perpendicular to a respective concavity of the curved puncture portion 1020 and curved anchor portion 1030.

In some embodiments, the curved puncture portion 1020 and the curved anchor portion 1030 can be integrally formed. For example, the distal portion 1012 of the elongate portion 1010 can comprise a curved distal elongate portion and the curved puncture portion 1020 extending from the curved distal elongate portion. The curved distal elongate portion can be the curved anchor portion 1030. The curved puncture portion 1020 can extend from the second end 1034 of the curved distal elongate portion, and can extend to the puncture tip 1040.

FIG. 11 shows an example of a puncture needle 1100 comprising a curved anchor portion 1130 and a distally or substantially distally oriented curved puncture portion 1120. The curved anchor portion 1120 can comprise a pre-formed curvature. An inner edge of a curvature of the curved puncture portion 1120 can comprise at least a portion oriented distally. For example, the concave portion of the curved puncture portion 1120 can comprise at least a portion which is oriented distally. The curved puncture portion 1120 can comprise one or more features of the curved puncture portion 520 described with reference to FIG. 7. The curved puncture portion 1120 can comprise a first end 1122 associated with a puncture tip 1140 and a second end 1124 coupled to the curved anchor portion 1130. The curved anchor portion 1130 can comprise a second end 1134 coupled to the curved puncture portion 1120. In some embodiments, the curved puncture portion 1120 can comprise a segment of a circle, such as a semi-circle. In some embodiments, the puncture tip 1140 can point distally. In some embodiments, the puncture tip 1140 can point laterally.

The puncture needle 1100 can comprise one or more other features of the puncture needle 1000 described with reference to FIG. 10. For example, a distal portion 1102 of the puncture needle 1100 can comprise the curved puncture portion 1120 and the curved anchor portion 1130. The puncture needle 1100 can comprise an elongate portion 1110 and a distal portion 1112 of the elongate portion 1010 can comprise the curved puncture portion 1120 and the curved anchor portion 1130. The curved anchor portion 1130 can comprise a portion extending distally of the curved puncture portion 1120, including a distal end 1132 of the curved anchor portion 1130. The curved anchor portion 1130 can be proximally oriented. In some embodiments, a curved puncture portion 1120 can have a radius of curvature smaller than that the curved anchor portion 1130.

In some embodiments, the curved puncture portion 1120 and the anchor portion 1130 can comprise at least some portions in the same plane and/or parallel planes. For example, the curved puncture portion 1120 and the curved anchor portion 1130 can extend along lines which are in the same plane and/or parallel planes. The curved puncture portion 1120 and the curved anchor portion 1130 can comprise respective portions in the same plane. The respective portions of the curved puncture portion 1120 and the curved anchor portion 1130 can extend along lines contained in the same plane, such that the curved puncture portion 1120 and the curved anchor portion 1130 each comprise portions which extend along lines contained in parallel planes. In some embodiments, a lateral cross section of the curved puncture portion 1120 and the curved anchor portion 1130 can comprise a non-circular shape, such as a polygonal shape, including a rectangular shape. Alternatively, the lateral cross section can comprise a rounded shape, including a circular shape. In some embodiments, the curved puncture portion 1120 and the curved anchor portion 1130 can be integrally formed. For example, the distal portion 1112 of the elongate portion 1110 can comprise a curved distal elongate portion and the curved puncture portion 1120 extending from the curved distal elongate portion. The curved distal elongate portion can be the curved anchor portion 1130.

Figure 12:
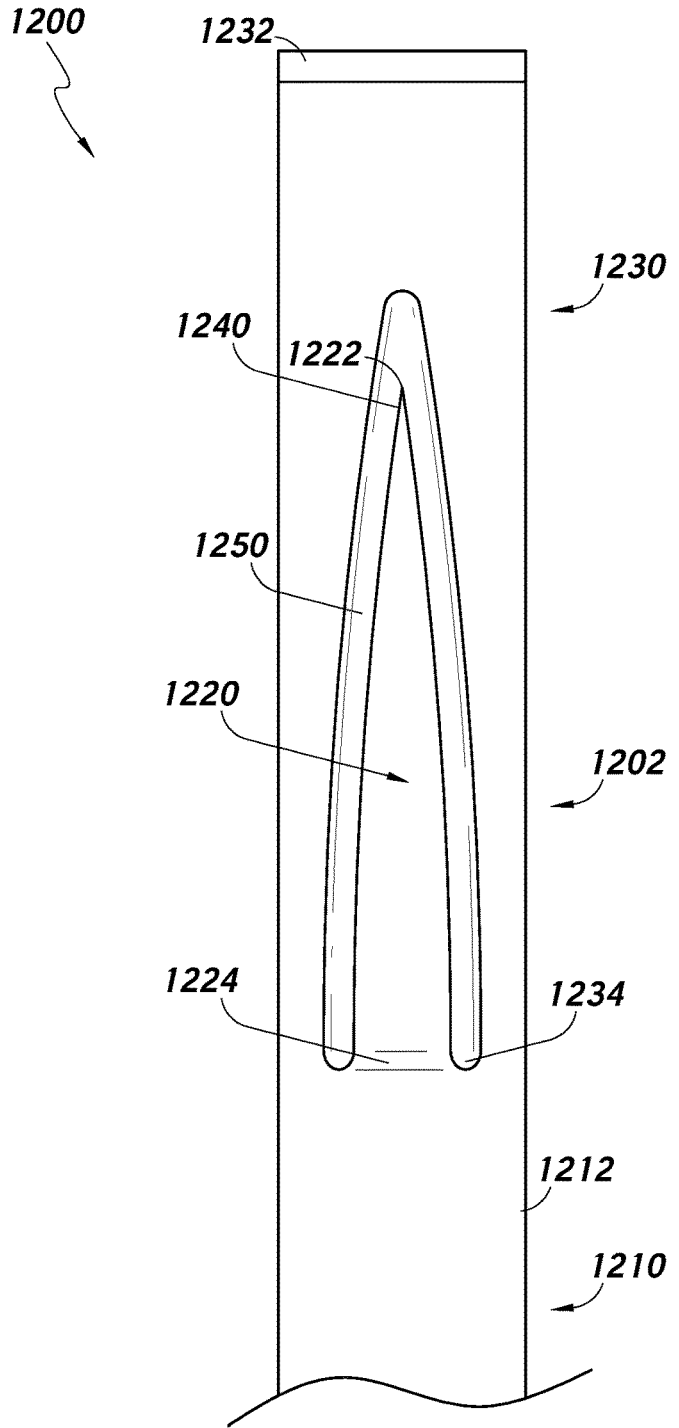
FIG. 12 shows an example of a puncture needle comprising a curved anchor portion and a curved puncture portion, which are integrally formed, in accordance with one or more embodiments.

FIG. 12 shows an example of a puncture needle 1200 comprising a distal portion 1202 which includes an anchor portion 1230 and a curved puncture portion 1220, where the anchor portion 1230 and the curved puncture portion 1220 are integrally formed. FIG. 12 is a plan view of the puncture needle 1200 which shows the curved puncture portion 1220 unfurled in a straight or substantially straight configuration. The curved puncture portion 1220 can comprise a shape memory material such that once the curved puncture portion 1220 is freed from the constraints of a delivery catheter, the curved puncture portion 1220 can assume its desired curved configuration. The curved puncture portion 1220 can comprise a first end 1222 associated with a puncture tip 1240, and a second end 1224 which meets the anchor portion 1230. The curved puncture portion 1220 and the anchor portion 1230 can be formed and/or derived from a single piece of material 1210. A distal portion 1212 of the piece of material 1210 can be split into two portions to provide the anchor portion 1230 and the curved puncture portion 1220. For example, the curved puncture portion 1220 can be cut and/or carved from the distal portion 1212 of the piece of material 1210. The curved puncture portion 1220 can be cut and/or carved from the piece of material 1210 such that the curved puncture portion 1220 can be released from a remaining portion of the piece of material 1210. The remaining portion of the piece of material 1210 can comprise the anchor portion 1230, for example extending from a position 1234 to a distal end 1232 on the distal portion 1212. In some embodiments, the curved puncture portion 1220 can be laser cut from the piece of material 1210. The released curved puncture portion 1220 can extend from the position 1234 on the distal portion 1212 of the piece of material 1210 to the first end 1222 associated with the puncture tip 1240. A surface region 1250 of the material 1210 from which the curved puncture portion 1220 is released is shown in FIG. 12. The surface region 1250 can be on the anchor portion 1230. The anchor portion 1230 can comprise a portion extending distally of the curved puncture portion 1220, including the distal end 1232 of the anchor portion 1230. For example, the portion extending distally of the curved puncture portion 1220 can comprise the surface region 1250 thereon.

The curved puncture portion 1220 and the anchor portion 1230 can comprise one or more features of the curved puncture portions and anchor portions as described herein. In some embodiments, the anchor portion 1230 can be a curved anchor portion. In some embodiments, the anchor portion 1230 can comprise a pre-formed curvature. In some embodiments, both the anchor portion 1230 and the curved puncture portion 1220 can be proximally oriented. In some embodiments, the curved puncture portion 1220 can have a radius of curvature smaller than that of the curved anchor portion. In some embodiments, the anchor portion 1230 can be linear or substantially linear. The linear or substantially linear anchor portion can be flexible so as to conform to one or more curvatures of a vessel, channel, chamber and/or organ into which the puncture needle 1200 is positioned.

In some embodiments, the curved puncture portion 1220 and the anchor portion 1230 can comprise at least some portions in the same plane and/or parallel planes, for example portions extending along lines which are in the same plane and/or parallel planes. In some embodiments, the curved puncture portion 1220 and the anchor portion 1230 can comprise corresponding portions in the same plane. For example, the curved puncture portion 1220 and the anchor portion 1230 can lay flat or substantially flat when laid on a side. Respective portions of the curved puncture portion 1220 and the anchor portion 1230 can extend along lines contained in the same plane, such that the curved puncture portion 1220 and the anchor portion 1230 each comprise respective portions which extend along lines contained in parallel planes.

Figure 13A:
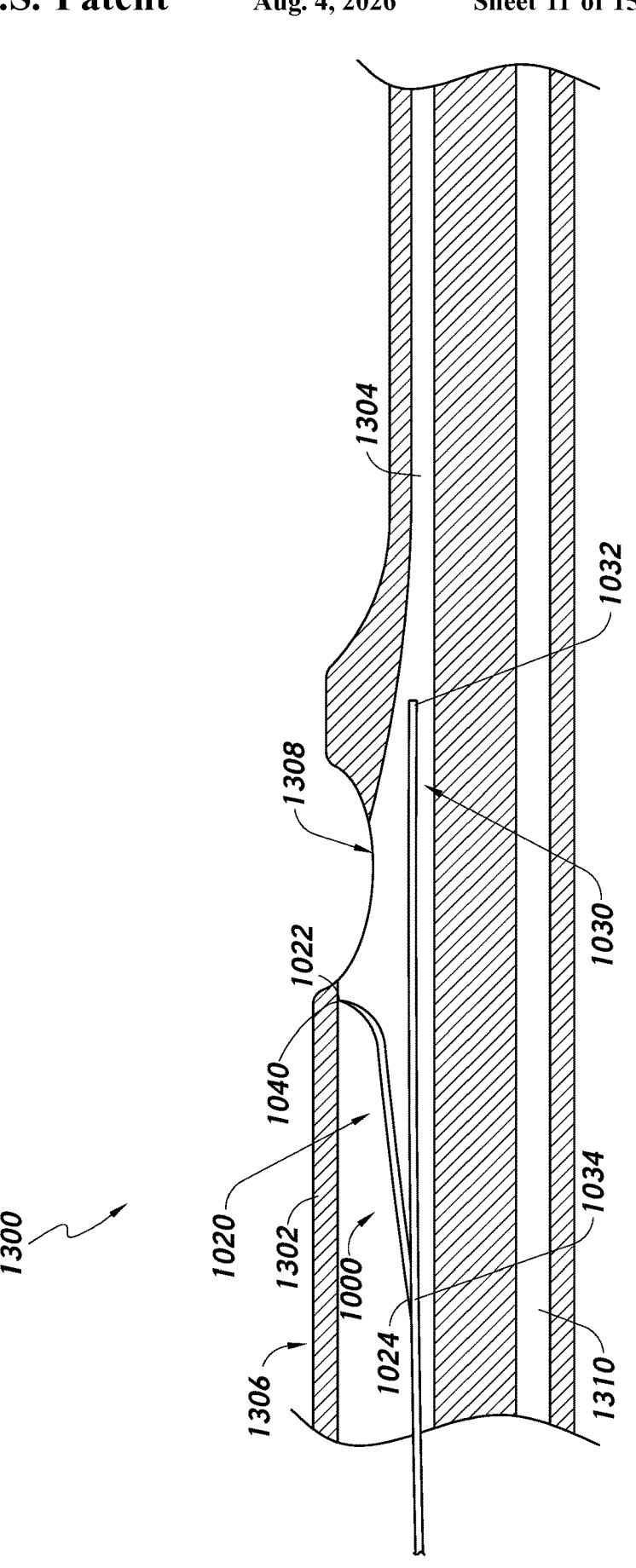
FIGS. 13A and 13B show a puncture needle system comprising the puncture needle described with reference to FIG. 10 in a retracted state and in a deployed state, respectively, in accordance with one or more embodiments.
Figure 13B:
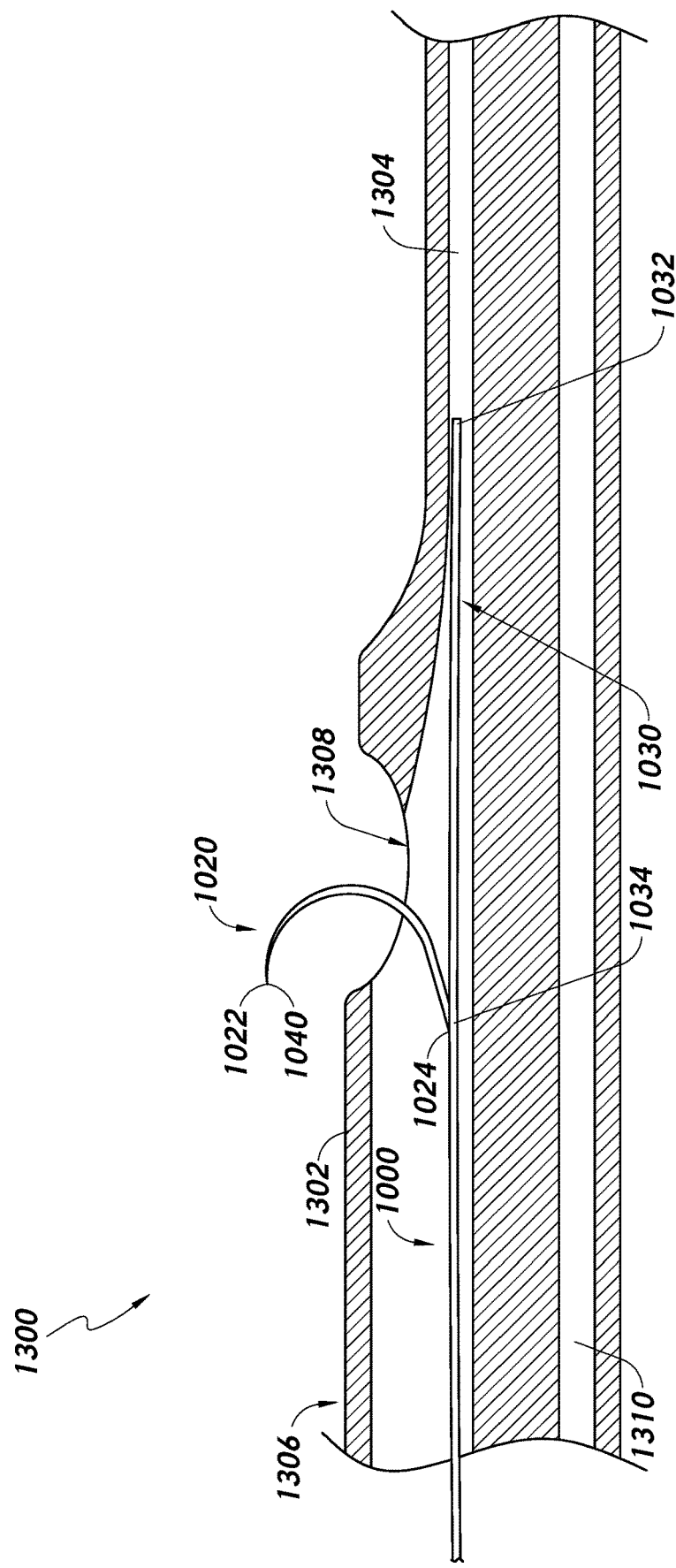

FIGS. 13A and 13B show a puncture needle system 1300. The puncture needle system 1300 can comprise the puncture needle 1000 described with reference to FIG. 10, and a delivery catheter 1302 configured to receive the puncture needle 1000. Side cross-sectional views along a longitudinal axis of the delivery catheter 1302 are shown in FIGS. 13A and 13B. FIG. 13A shows the puncture needle 1000 pre-loaded in the delivery catheter 1302 and in a retracted state.

FIG. 13B shows the puncture needle 1000 in a deployed state. Referring to FIG. 13A, the delivery catheter 1302 can comprise a puncture needle lumen 1304 configured to receive the puncture needle 1000. A distal portion 1306 of the delivery catheter 1302 can comprise a side outlet opening 1308. The puncture needle 1000 can be extended through the side outlet opening 1308 to access the target tissue site.

The delivery catheter 1302 can comprise a guide wire lumen 1310 extending along a length, such as an entire length, of the delivery catheter 1302, and configured to receive a delivery catheter guide wire (not shown). The delivery catheter 1302 can be advanced along the delivery catheter guide wire into a vessel, channel, chamber, and/or organ to position the side outlet opening 1308 at or proximate to the target tissue site. In some embodiments, after the delivery catheter is advanced along the delivery catheter guide wire to the desired location within the vessel, channel, chamber, and/or organ, the delivery catheter guide wire can be retracted, leaving the delivery catheter at the desired location.

The anchor portion 1030 can comprise a portion configured to be positioned within a portion of the puncture needle lumen 1304 distal of the side outlet opening 1308, both in the retracted state and in the deployed state. For example, the distal end 1032 of the anchor portion 1030 can remain in the portion of the puncture needle lumen 1304 distal of the side outlet opening 1308. The portion of the anchor portion 1030 distal of the side outlet opening 1308 can engage with the wall of the portion of the puncture needle lumen 1304 distal of the side outlet opening 1308 to reduce or eliminate undesired rotation of the curved puncture portion 1020 around a longitudinal axis of the puncture needle 1000.

Referring to FIG. 13A, in the retracted state, the curved puncture portion 1020 can remain or substantially remain within the puncture needle lumen 1304. The second end 1024 of the curved puncture portion 1020 can be proximal of the side outlet opening 1308. FIG. 13A shows the puncture tip 1040 proximal of the side outlet opening 1308. In some embodiments, the entirety or substantially entirety of the curved puncture portion 1020 can be proximal of the side outlet opening 1308. For example, the puncture tip 1040 and the curved puncture portion 1020 can be proximal of the side outlet opening 1308 and can be received within the puncture needle lumen 1304. The second end 1024 of the curved puncture portion 1020 and the second end 1034 of the anchor portion 1030 can be proximal of the side outlet opening 1308. The anchor portion 1030 can extend along the puncture needle lumen 1304 past the side outlet opening 1308. For example, the anchor portion 1030 can extend along a portion of the puncture needle lumen 1304 proximal of the side outlet opening 1308, through a portion of the lumen 1304 at the side outlet opening 1308, and along a portion of the puncture needle lumen 1304 distal of the side outlet opening 1308.

In some embodiments, both the curved puncture portion 1020 and the anchor portion 1030 can engage with corresponding portions of the delivery catheter lumen wall to prevent or reduce axial rotation of the curved puncture portion 1020. For example, the curved puncture portion 1020 and the anchor portion 1030 can have a tendency to extend radially. For example, the curved puncture portion 1020 and the anchor portion 1030 can be spring-loaded. The tendency to extend radially can increase contact between the puncture needle 1000 and the lumen wall of the delivery catheter 1302, facilitating fixation of the position and/or orientation of the curved puncture portion 1020. In some embodiments, the tendency of the anchor portion 1030 and curved puncture portion 1020 to extend radially can facilitate extension of the curved puncture portion 1020 through the side outlet opening 1308 when deploying the puncture needle 1000.

Referring to FIG. 13B, in the deployed state, at least a portion of the curved puncture portion 1020 can be extended through the side outlet opening 1308. In some embodiments, only a portion of the curved puncture portion 1020 is extended through the side outlet opening. For example, the second end 1024 can be within the lumen 1304 and proximal of the side outlet opening 1308. Alternatively, the entire or substantially the entire curved puncture portion 1020 can be extended beyond the side outlet opening 1308. For example, the second end 1024 of the curved puncture portion 1020 and the second end 1034 of the anchor portion 1030 can be aligned with the side outlet opening 1308. The entire curved puncture portion 1020 and the puncture tip 1040 can be extended through the side outlet opening 1308.

The puncture needle 1000 can be distally translated relative to the delivery catheter 1302 to release at least a portion of the curved puncture portion 1020 through the side outlet opening 1308, such as releasing the entire or substantially the entire curved puncture portion 1020. The curved puncture portion 1020 can comprise a shape memory material such that as the curved puncture portion 1020 is aligned with the side outlet opening 1308, the curved puncture portion 1020 can extend through the side outlet opening 1308 and assume its desired curved configuration. The puncture needle 1000 can be translated proximally to retract the curved puncture portion 1020 back into the puncture needle lumen 1304 through the side outlet opening 1308, after the opening at the target tissue location is formed. For example, the puncture needle 1000 can be pulled to retract the curved puncture portion 1020 back into the lumen 1304.

Alternatively, in some embodiments, while the puncture needle 1000 is in the retracted state, at least a portion of the curved puncture portion 1020 can be positioned within the portion of the puncture needle lumen 1304 distal of the side outlet opening 1308. For example, the puncture tip 1040 can be distal of the side outlet opening 1308. In some embodiments, in the retracted state, the curved puncture portion 1020 can be entirely or substantially entirely distal of the side outlet opening 1308. The puncture needle 1000 can be translated proximally relative to the delivery catheter 1302 to release at least a portion of the curved puncture portion 1020 through the side outlet opening 1308. The puncture needle 1000 can be pulled to align the curved puncture portion 1020 with the side outlet opening 1308 such that the puncture tip 1040 and at least a portion of the curved puncture portion 1020 can be extended through the side outlet opening 1308.

FIGS. 14A through 14D show an example of a puncture needle system 1400 comprising a delivery catheter 1402 and a puncture needle 1500. The delivery catheter 1402 can comprise a puncture needle lumen 1404 configured to receive the puncture needle 1500. A distal portion 1406 of the delivery catheter 1402 can comprise a side outlet opening 1408 configured to allow extension therethrough of a portion of the puncture needle 1500 for accessing and forming an opening at the target tissue site. The delivery catheter 1402 can comprise a guide wire lumen 1410 configured to receive a delivery catheter guide wire (not shown). For example, the guide wire lumen 1410 can extend along a length, such as an entire length, of the delivery catheter 1402 such that the delivery catheter 1402 can be advanced along the delivery catheter guide wire into the desired vessel, channel, chamber, and/or organ. In some embodiments, the delivery catheter guide wire can be withdrawn after the delivery catheter 1402 is positioned at the target location, leaving the delivery catheter 1402 in place.

Figures 14A, 14B, 14C:
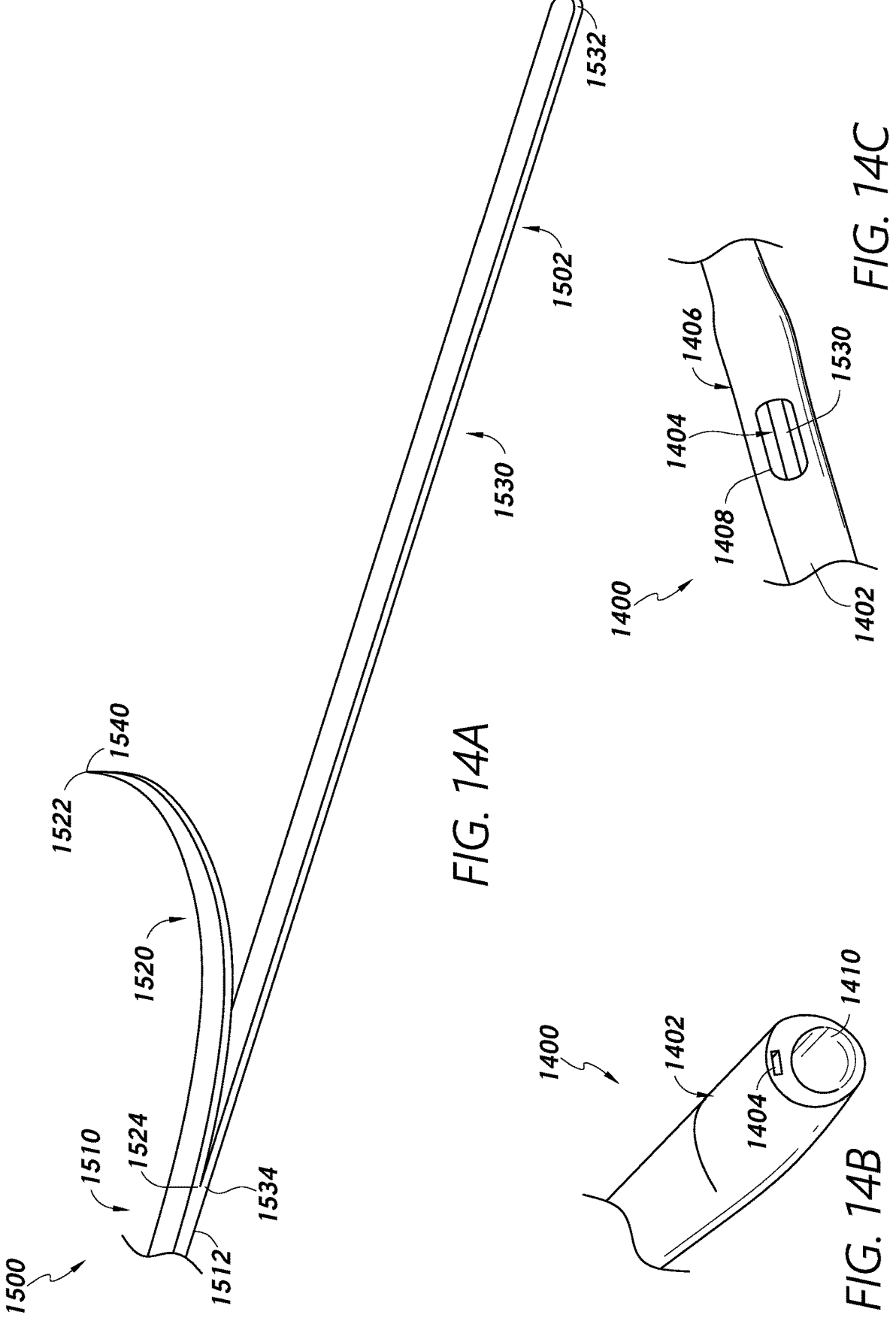
FIGS. 14A, 14B, 14C and 14D show another example of a puncture needle system, in accordance with one or more embodiments.

FIG. 14A shows a distal portion 1502 of the puncture needle 1500. The distal portion 1502 can comprise a curved puncture portion 1520 coupled to an anchor portion 1530. For example, a distal portion 1512 of an elongate portion 1510 of the puncture needle 1500 can comprise the curved puncture portion 1520 extending from the anchor portion 1530. The anchor portion 1530 can comprise a distal end 1532, and a second end 1534 coupled to the curved puncture portion 1520. The curved puncture portion 1520 can comprise a first end 1522 associated with a puncture tip 1540 and a second end 1524 coupled to the second end 1534 of the anchor portion 1530. The anchor portion 1530 can comprise a portion extending distally of the curved puncture portion 1520, including for example the distal end 1532 of the anchor portion 1530.

In some embodiments, the anchor portion 1530 can assume a linear or substantially linear configuration in a relaxed state. The anchor portion 1530 can be flexible. For example, the anchor portion 1530 can bend to assume a curved configuration. The anchor portion 1530 can assume the curved configuration while received within the delivery catheter 1402. For example, the anchor portion 1530 can assume the curved configuration while the delivery catheter 1402 is advanced through a tortuous anatomical pathway to a desired location to access the target tissue site and/or while the delivery catheter 1402 is positioned at or proximate to the desired location. A radius of curvature of the anchor portion 1530 in the curved configuration can be based on a curvature of the anatomical pathway adjacent to or proximate to the target tissue site, such as a length of the coronary sinus adjacent to or proximate to the target tissue site on the left atrial wall. A radius of curvature of the curved puncture portion 1520 can be selected to facilitate effective piercing of the tissue while the puncture needle 1500 is positioned at a desired location to access the target tissue site. For example, the radius of curvature can be predetermined to enable desired insertion of the curved puncture portion 1520 through the target tissue as the puncture needle 1500 is extended from the side outlet opening 1408. In some embodiments, the radius of curvature of the anchor portion 1530 in the curved configuration while positioned at or proximate to the target tissue site is larger than that of the curved puncture portion 1520, the degree of curvature of the curved puncture portion 1520 being larger than that of the anchor portion 1530. The curvature of the curved puncture portion 1520 and that of the anchor portion 1530 in the curved configuration while positioned at or proximate to the target tissue site can have the same orientation, such as being proximally oriented. In some embodiments the puncture tip 1540 can be laterally pointed. In some embodiments, the puncture tip 1540 can be proximally pointed.

As shown in FIG. 14A, a lateral cross section of the anchor portion 1530 can have a non-circular shape, such as a polygonal shape. The lateral cross section can be taken along a plane perpendicular or substantially perpendicular to a longitudinal axis of the puncture needle 1500. In some embodiments, the lateral cross section of the anchor portion 1530 can be rectangular or substantially rectangular. In some embodiments, the lateral cross-sectional shape can be selected to interlock with a lateral cross-sectional shape of the delivery catheter lumen 1404 such that the anchor portion 1530 does not or substantially does not axially rotate within the lumen 1404, thereby reducing or eliminating axial rotation of the curved puncture portion 1520. The anchor portion 1530 can comprise at least a portion which extends distally of the side outlet opening 1408 while the puncture needle 1500 is both a retracted state and a deployed state. For example, the lateral cross-sectional shape of the lumen 1404 distal of the side outlet opening 1408 can be non-circular so as to interlock with the anchor portion 1530.

In some embodiments, a lateral cross section of the curved puncture portion 1520 can be non-circular. The lateral cross section can be taken along a plane perpendicular to the concavity of the curved puncture portion 1520. The lateral cross section can be selected to reduce a profile of the curved puncture portion 1520, thereby facilitating a reduced profile of the puncture needle 1500. In some embodiments, the lateral cross section can comprise a polygonal shape, including a rectangular or substantially rectangular shape. The concavity of the curved puncture portion 1520 can generally be normal to the long flat surface of the rectangular-cross-sectional form thereof, as in FIG. 14A.

In some embodiments, the curved puncture portion 1520 and the anchor portion 1530 can be in the same plane and/or parallel planes, for example extending along lines which are in the same plane and/or parallel planes. In some embodiments, the curved puncture portion 1520 and the anchor portion 1530 can be in the same plane. For example, the curved puncture portion 1520 and the anchor portion 1530 can lay flat or substantially flat when laid on a side. In some embodiments, respective portions of the curved puncture portion 1520, the anchor portion 1530 can extend along lines contained in the same plane, such that the curved puncture portion 1520 and the anchor portion 1530 each comprise portions which extend along lines contained in parallel planes. In some embodiments, the curved puncture portion 1520 and the anchor portion 1530 can be integrally formed, for example being a part of a single elongate portion. For example, the distal portion 1512 of the elongate portion 1510 can comprise the curved puncture portion 1520 and the anchor portion 1530.

FIG. 14B is a lateral cross-sectional view of a portion of the delivery catheter 1402 distal of the side outlet opening 1408. The lateral cross section can be taken along a plane perpendicular or substantially perpendicular to a longitudinal axis of the delivery catheter 1402. The guide wire lumen 1410 and the puncture needle lumen 1404 are shown. The guide wire lumen 1410 can comprise a rounded shape, such as a circular or substantially circular shape. The lateral cross section of the puncture needle lumen 1404 distal of the side outlet opening 1408 can comprise a rectangular or substantially rectangular shape.

FIG. 14C is a perspective view of the portion of the delivery catheter 1402 comprising the side outlet opening 1408. The puncture needle system 1400 is shown with the puncture needle 1500 in a retracted state. The anchor portion 1530 is shown as extending within the puncture needle lumen 1404 past the side outlet opening 1408. The second end 1524 of the curved puncture portion 1520 and the second end 1534 of the anchor portion 1530 can be proximal of the side outlet opening 1408. The anchor portion 1530 can extend along a portion of the puncture needle lumen 1404 proximal of the side outlet opening 1408, through a portion of the lumen 1404 at the side outlet opening 1408, and along a portion of the puncture needle lumen 1404 distal of the side outlet opening 1408. The anchor portion 1530 can extend through a portion of the puncture needle lumen 1404 distal of the side outlet opening 1408. The curved puncture portion 1520 can be entirely or substantially entirely within a portion of the puncture needle lumen 1404 proximal of the side outlet opening 1408. For example, the puncture tip 1540 can be within the lumen 1404 and proximal of the side outlet opening 1408. The puncture needle 1500 can be translated distally, such as pushed, to release the curved puncture portion 1520 through the side outlet opening 1408 so as to deploy the curved puncture portion 1520. In some embodiments, the puncture tip 1540 can be within the lumen 1404 and distal of the side outlet opening 1408. The puncture needle 1500 can be translated proximally, such as pulled, to release the curved puncture portion 1520 through the side outlet opening 1408. The curved puncture portion 1520 can comprise a shape memory material such that once the curved puncture portion 1520 is freed from the constraints of the delivery catheter 1402, the curved puncture portion 1520 can assume its desired curved configuration.

Figure 14D:
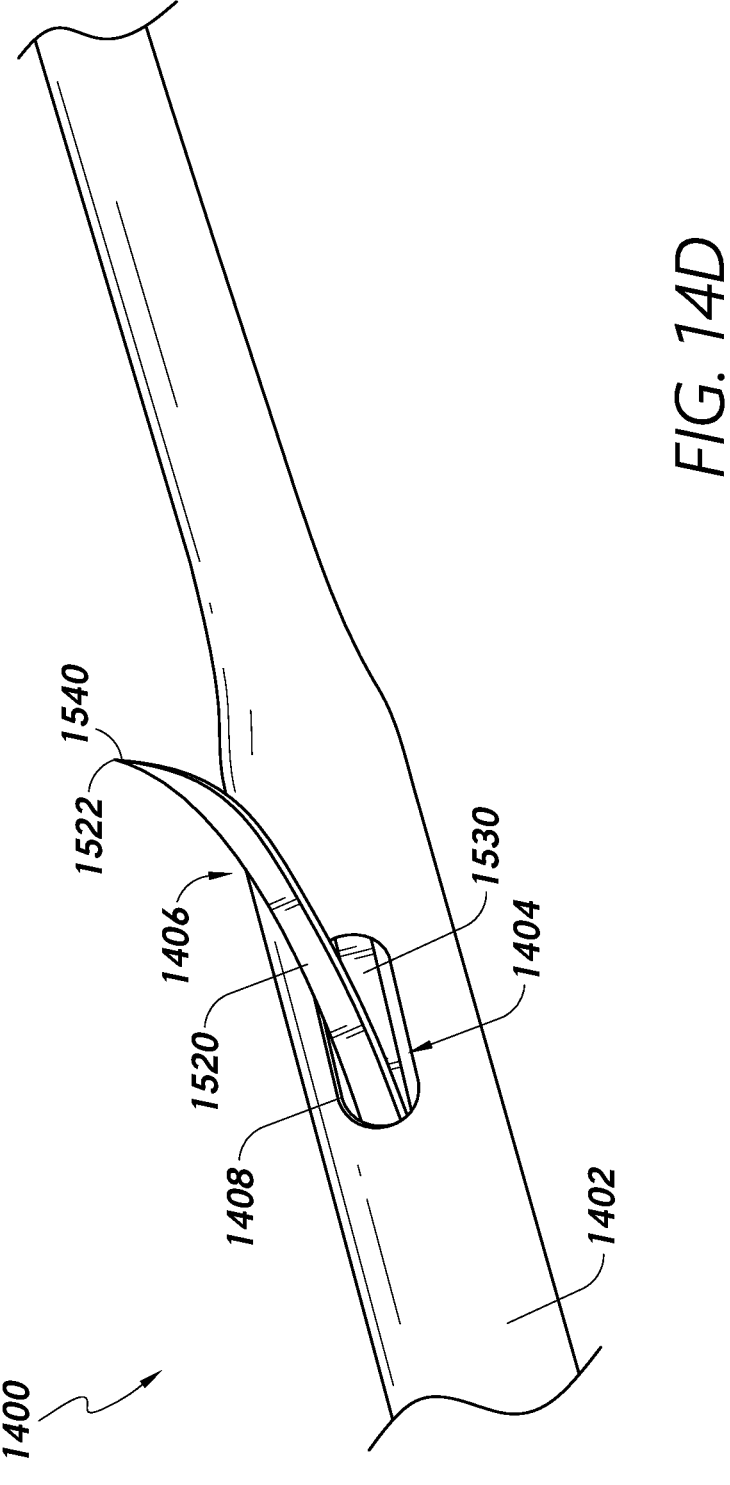

FIG. 14D shows the puncture needle system 1400 in a deployed state. The curved puncture portion 1520 is shown as being extended through the side outlet opening 1408. In some embodiments, the curved puncture portion 1520 can be partially extended through the side outlet opening 1408. For example, the second end 1524 of the curved puncture portion 1520 and the second end 1534 of the anchor portion 1530 can be proximal of the side outlet opening 1408. As the second end 1534 is within the delivery catheter lumen 1404 and proximal of the side outlet opening 1408, the second end 1534 is not shown in FIG. 14D. In some embodiments, the entire or substantially the entire curved puncture portion 1520 is extended through the side outlet opening. For example, the second end 1524 of the curved puncture portion 1520 and the second end 1534 of the anchor portion 1530 can be aligned with the side outlet opening 1408. As described herein, while the puncture needle 1500 is in the deployed state, the anchor portion 1530 can comprise at least a portion which extends distally of the side outlet opening 1408. In FIG. 14D, the anchor portion 1530 is shown as extending through the lumen 1404 past the side outlet opening 1408.

FIG. 15 is a flow diagram of an example of a process 1600 to deploy a puncture needle system for piercing tissue at a target tissue site. The puncture needle system can comprise features of one or more of the puncture needle systems as described herein. At block 1602, the procedure/process 1600 involves advancing the puncture needle system into a vessel. For example, the vessel can be a coronary sinus. The puncture needle system can be advanced into the coronary sinus via the coronary sinus ostium from the right atrium. A transjugular or trans-subclavian approach can be used to access the right atrium via the superior vena cava. Alternatively, a transfemoral approach can be used to position the puncture needle system into the inferior vena cava, and from the inferior vena cava into the right atrium. The procedure/process 1600 can comprise a minimally invasive transcatheter approach.

In some embodiments, the puncture needle system can be delivered into the coronary sinus to access a left atrial wall from within the coronary sinus. The puncture needle system can be used to access a target tissue site on the left atrial wall. The puncture needle system can be used to form an opening on the left atrial wall for delivery of one or more medical therapies and/or implant devices. For example, the opening can be formed on the left atrial wall for implantation of a shunt device therein, such as to provide an artificial blood flow conduit for alleviating elevated left atrial pressure.

The puncture needle system can comprise a puncture needle. The puncture needle can comprise one or more features of the puncture needles as described herein. For example, the puncture needle can comprise an anchor portion and a curved puncture portion. The puncture portion can comprise a first end associated with a puncture tip and a second end coupled to the anchor portion. The anchor portion can comprise a portion distal of the curved puncture portion. The puncture needle system can comprise a delivery catheter configured to receive the puncture needle. The delivery catheter can comprise a puncture needle lumen, and the puncture needle can be extended slidably through the puncture needle lumen. A side outlet opening can be on a distal portion of the delivery catheter such that at least a portion of the curved puncture portion can be extended therethrough.

As described herein, the puncture needle can be pre-loaded. For example, prior to positioning the delivery catheter at the target tissue site, such as prior to insertion of the delivery catheter into the patient, the puncture needle can be at a desired position within the delivery catheter. For example, a distal portion of the puncture needle can be at or proximate to the side outlet opening while the delivery catheter is advanced to the target tissue site. The puncture needle can be in a retracted state within the delivery catheter as the delivery catheter is advanced to the target tissue site. In some embodiments, while the puncture needle is in the retracted state, at least a portion of the anchor portion is positioned within a portion of the puncture needle lumen distal of the side outlet opening. In some embodiments, interaction between the anchor portion and the portion of the puncture needle lumen wall distal of the side outlet opening can facilitate maintaining an axial orientation of the curved puncture portion relative to the delivery catheter, regardless of any axial rotations of any portions of the puncture needle proximal of the curved puncture portion.

In some embodiments, while the puncture needle is in the retracted state, the curved puncture portion can be positioned proximal of the side outlet opening. In some embodiments, at least a portion of the curved puncture portion can be positioned distal of the side outlet opening while the puncture needle is in the retracted state. For example, a portion of the curved puncture portion and the puncture tip can be within a portion of the puncture needle lumen distal of the side outlet opening. In some embodiments, the puncture tip can be within the side outlet opening and the curved puncture portion can comprise at least a portion positioned within a portion of the puncture needle lumen proximal of the side outlet opening.

At block 1604, the procedure/process 1600 involves one of distally or proximally translating the puncture needle relative to the delivery catheter to release at least a portion of the curved puncture portion through the side outlet opening. The puncture needle can be pushed or pulled to align the curved puncture portion with the side outlet opening such that the puncture tip and at least a portion of the curved puncture portion can be extended through the side outlet opening. For example, a puncture needle comprising a puncture tip distal of the side outlet opening in the retracted state can be translated proximally relative to the delivery catheter to release at least a portion of the curved puncture portion through the side outlet opening. A puncture needle comprising a puncture tip proximal of the side outlet opening in the retracted state can be translated distally relative to the delivery catheter to release at least a portion of the curved puncture portion through the side outlet opening. In some embodiments, the curved puncture portion can comprise a shape memory material such that once at least a portion of the curved puncture portion is freed from the constraints of the delivery catheter, the curved puncture portion can tend to assume its desired curved configuration.

At block 1606, the procedure/process 1600 involves extending at least a portion of the curved puncture portion through the side outlet opening. In a deployed state, the puncture needle can comprise the entirety or substantially the entirety of the curved puncture portion extended beyond the side outlet opening. In some embodiments, only a portion of the curved puncture portion is extended beyond the side outlet opening while the puncture needle is in a deployed state. As described herein, the curved puncture portion can comprise a pre-formed curvature configured to facilitate accessing the target tissue site while the puncture needle system is positioned in the vessel so as to facilitate effective puncture of the target tissue site. For example, the pre-formed curvature of the curved puncture portion can have a radius of curvature to facilitate accessing and/or puncturing the target tissue site on the left atrial wall while the curved puncture portion is extended from the delivery catheter positioned in the coronary sinus.

At block 1608, the procedure/process 1600 involves piercing tissue at the target tissue site to form an opening at the target tissue site using the puncture tip of the puncture needle which has been extended through the side outlet opening.

In some embodiments, the puncture needle system can comprise a medical implant guide wire sheath configured to slidably receive a medical implant guide wire. The medical implant guide wire sheath can comprise a distal portion coupled to at least a portion of the curved puncture portion. The medical implant guide wire can be advanced within the medical implant guide wire sheath to the target tissue site. The medical implant guide wire can be advanced through an opening associated with a distal end of the medical implant guide wire sheath into the opening formed at the target tissue site. After the medical implant guide wire is positioned at its target position, the medical implant guide wire sheath can be retracted, leaving the medical implant guide wire in place. A medical implant device, such as a shunt device, can then be advanced along the medical implant guide wire to a target implantation site. For example, the shunt device can be advanced along the medical implant guide wire into the opening formed on the left atrial wall.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A puncture needle comprising:
a puncture tip configured to pierce tissue; and
an elongate portion, wherein the elongate portion comprises a distal portion comprising:
    a curved puncture portion having a first end associated with the puncture tip, and the curved puncture portion being proximally oriented and the puncture tip pointing proximally;
    a first distal elongate portion, the curved puncture portion extending from the first end to the first distal elongate portion and the first distal elongate portion meeting the curved puncture portion at a distally oriented acute angle; and
    a second distal elongate portion, the first distal elongate portion and the second distal elongate portion meeting at a proximally oriented acute angle, and the second distal elongate portion extending proximally from the proximally oriented acute angle, wherein the proximally oriented acute angle is distal of the curved puncture portion.

2. The puncture needle of claim 1, wherein the first distal elongate portion, the second distal elongate portion and the curved puncture portion are in one plane.

3. The puncture needle of claim 1, wherein the elongate portion is a single wire.

4. The puncture needle of claim 1, wherein the first distal elongate portion comprises a first distal curved portion and the second distal elongate portion comprises a second distal curved portion, the first distal curved portion and the second distal curved portion having a same orientation as the curved puncture portion.

5. The puncture needle of claim 4, wherein a radius of curvature of the curved puncture portion is smaller than that of each of the first distal curved portion and the second distal curved portion.

6. A puncture needle comprising:
a puncture tip configured to pierce tissue; and
a distal portion comprising:
    an anchor portion comprising a first curved anchor portion and a second curved anchor portion; and
    a curved puncture portion comprising a first end associated with the puncture tip and a second end coupled to the anchor portion, the curved puncture portion and the anchor portion meeting at a distally oriented acute angle, wherein the anchor portion comprises a portion distal of the curved puncture portion,
    the first curved anchor portion and second curved anchor portion each comprising a shape configured to conform to a curvature along a length of a coronary sinus.

7. The puncture needle of claim 6, wherein the curved puncture portion is proximally oriented, and wherein the puncture tip points proximally.

8. The puncture needle of claim 6, wherein the curved puncture portion is distally oriented, and wherein the puncture tip points distally.

9. The puncture needle of claim 6, wherein the curved puncture portion comprises a segment of a circle.

10. The puncture needle of claim 9, wherein the curved puncture portion comprises a semi-circle.

11. The puncture needle of claim 6, wherein the distal portion comprises a lateral cross-section having a rectangular shape, the lateral cross-section being taken along a plane perpendicular to a longitudinal axis of the puncture needle.

12. The puncture needle of claim 6, wherein the anchor portion comprises:
    the first curved anchor portion comprising a first end and a second end, wherein the first end of the first curved anchor portion is coupled to the curved puncture portion; and
    the second curved anchor portion comprising a first end coupled to the second end of the first curved anchor portion, and wherein the second curved anchor portion extends proximally from the first end of the second curved anchor portion,
    wherein the first curved anchor portion and the second curved anchor portion meet at a bend, the bend is proximally oriented, and the bend is distal of the curved puncture portion.

13. The puncture needle of claim 12, wherein the bend comprises an acute angle.

14. The puncture needle of claim 6, wherein the curved puncture portion, the first curved anchor portion, and the second curved anchor portion are in one plane.

15. The puncture needle of claim 6, wherein the curved puncture portion, the first curved anchor portion, and the second curved anchor portion comprise a same orientation.

16. The puncture needle of claim 6, wherein a radius of curvature of the curved puncture portion is smaller than that of each of the first curved anchor portion and the second curved anchor portion.

17. The puncture needle of claim 6, wherein the first curved anchor portion meets the curved puncture portion at the distally oriented acute angle, and the second curved anchor portion meets the first curved anchor portion at an opposingly oriented angle.

18. The puncture needle of claim 6, wherein the curved puncture portion and the anchor portion form a zig-zag shape.

19. The puncture needle of claim 6, wherein corresponding concave portions of the first curved anchor portion and the second curved anchor portion comprise a common proximal orientation.

20. The puncture needle of claim 19, wherein a concave portion of the curved puncture portion comprises a common orientation as the corresponding concave portions of the first and second curved anchor portions.

21. A puncture needle system, comprising:
a puncture needle comprising a puncture tip and a distal portion, the distal portion comprising:
    an anchor portion, and
    a curved puncture portion comprising a first end associated with the puncture tip and a second end coupled to the anchor portion, the anchor portion comprising a portion distal of the curved puncture portion; and
a delivery catheter comprising a lumen, the puncture needle extending through the lumen, and a side outlet opening on a distal portion of the delivery catheter configured to allow extension therethrough of at least a portion of the curved puncture portion, wherein the anchor portion extends through a distal portion of the lumen distal of the side outlet opening, wherein while the puncture needle is in a retracted state, the puncture tip is configured to be proximal of the side outlet opening and the anchor portion comprises a portion extending along the lumen past the side outlet opening and through the portion of the lumen distal of the side outlet opening.

22. The system of claim 21, wherein the distal portion of the lumen distal of the side outlet opening comprises a lateral cross section comprising a non-circular shape, the lateral cross section being taken along a plane perpendicular to a longitudinal axis of the delivery catheter.

23. The system of claim 22, wherein the lateral cross-section of the distal portion of the lumen comprises a same shape as a lateral cross section of the anchor portion.

24. The system of claim 21, and further comprising a medical implant guide wire sheath configured to slidably receive a medical implant guide wire, the medical implant guide wire sheath comprising a distal portion coupled to at least a portion of the curved puncture portion.

25. The system of claim 21, wherein the anchor portion is a curved anchor portion, the curved anchor portion comprising the portion distal of the curved puncture portion, and a proximal portion coupled to the second end of the curved puncture portion.

26. The system of claim 21, wherein the anchor portion comprises:
a first anchor portion comprising a first end and a second end, wherein the first end of the first anchor portion is coupled to the curved puncture portion; and
a second anchor portion comprising a first end coupled to the second end of the first anchor portion, and wherein the second anchor portion extends proximally from the first end of the second anchor portion,
wherein the first anchor portion and the second anchor portion meet at a bend, the bend is proximally oriented, and the bend is distal of the curved puncture portion.

27. The system of claim 26, wherein the curved puncture portion, the first anchor portion, and the second anchor portion are in one plane.

28. The system of claim 26, wherein the first anchor portion is a first curved anchor portion and the second anchor portion is a second curved anchor portion, wherein the curved puncture portion, the first curved anchor portion, and the second curved anchor portion comprise a same orientation.

29. The system of claim 26, wherein the first anchor portion and the second anchor portion are each linear portions.

* * * * *